United States Patent
Du et al.

(10) Patent No.: US 10,863,918 B2
(45) Date of Patent: Dec. 15, 2020

(54) SYSTEMS AND METHODS FOR ULTRASHORT ECHO TIME MAGNETIZATION TRANSFER (UTE-MT) IMAGING AND SIGNAL MODELING

(71) Applicant: The Regents of the University of California, Oakland, CA (US)

(72) Inventors: Jiang Du, San Diego, CA (US); Yajun Ma, San Diego, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 97 days.

(21) Appl. No.: 16/300,036

(22) PCT Filed: May 9, 2017

(86) PCT No.: PCT/US2017/031805
§ 371 (c)(1),
(2) Date: Nov. 8, 2018

(87) PCT Pub. No.: WO2017/196878
PCT Pub. Date: Nov. 16, 2017

(65) Prior Publication Data
US 2019/0142297 A1    May 16, 2019

Related U.S. Application Data

(60) Provisional application No. 62/333,757, filed on May 9, 2016.

(51) Int. Cl.
*A61B 5/055* (2006.01)
*G01R 33/48* (2006.01)
(Continued)

(52) U.S. Cl.
CPC ............ *A61B 5/055* (2013.01); *A61B 5/4504* (2013.01); *A61B 5/4514* (2013.01);
(Continued)

(58) Field of Classification Search
CPC ............ G01R 33/4816; G01R 33/4826; G01R 33/4828; G01R 33/5605; A61B 5/055;
(Continued)

(56) References Cited

U.S. PATENT DOCUMENTS 8,369,599 B2 * 2/2013 Yarnykh ............ G01R 33/4608
                                                                382/131
8,686,727 B2 * 4/2014 Reddy ................ G01R 33/5605
                                                                324/307
(Continued)

OTHER PUBLICATIONS

ISA, International Search Report and Written Opinion for International Patent Application No. PCT/US2017/031805. dated Sep. 22, 2017. 10 pages.

*Primary Examiner* — Dixomara Vargas
(74) *Attorney, Agent, or Firm* — Perkins Coie LLP

(57) ABSTRACT

Disclosed are methods and systems for ultrashort echo time magnetization transfer (UTE-MT) imaging and signal modeling to quantify the different proton groups, including free water, bound water and macromolecule protons in short T2 tissues such as the menisci, ligaments, tendons and cortical bone. UTE-MT images with a series of MT frequency offsets and MT power are subject to MT modeling to evaluate T1s, T2s, fractions and exchange rates of bound water, free water and macromolecule protons.

23 Claims, 29 Drawing Sheets

(51) Int. Cl.
  *G01R 33/56* (2006.01)
  *G16H 30/40* (2018.01)
  *A61B 5/00* (2006.01)
(52) U.S. Cl.
  CPC .......... *A61B 5/4523* (2013.01); *A61B 5/4533* (2013.01); *G01R 33/4816* (2013.01); *G01R 33/4826* (2013.01); *G01R 33/4828* (2013.01); *G01R 33/5605* (2013.01); *G16H 30/40* (2018.01); *A61B 2576/00* (2013.01)
(58) Field of Classification Search
  CPC ... A61B 5/4504; A61B 5/4514; A61B 5/4523; A61B 5/4533; G16H 30/40
  See application file for complete search history.

(56) References Cited

U.S. PATENT DOCUMENTS

| | | | | |
|---|---|---|---|---|
| 9,157,976 | B2* | 10/2015 | Reddy | G01R 33/5605 |
| 10,302,722 | B2* | 5/2019 | Alsop | A61B 5/055 |
| 2007/0255129 | A1 | 11/2007 | Du et al. | |
| 2010/0142784 | A1* | 6/2010 | Yarnykh | G01R 33/56366 |
| | | | | 382/131 |
| 2010/0315084 | A1 | 12/2010 | Sacolick et al. | |
| 2012/0019245 | A1* | 1/2012 | Reddy | G01R 33/5605 |
| | | | | 324/309 |
| 2012/0289818 | A1* | 11/2012 | van Zijl | G01R 33/5601 |
| | | | | 600/414 |
| 2013/0069649 | A1 | 3/2013 | Mangia et al. | |
| 2013/0190601 | A1* | 7/2013 | Alsop | G01R 33/5605 |
| | | | | 600/410 |
| 2013/0278255 | A1* | 10/2013 | Khalighi | G01R 33/5659 |
| | | | | 324/309 |
| 2014/0213887 | A1* | 7/2014 | Reddy | G01R 33/5605 |
| | | | | 600/414 |
| 2014/0361776 | A1* | 12/2014 | Miyazaki | G01R 33/50 |
| | | | | 324/322 |
| 2016/0041246 | A1* | 2/2016 | Alsop | A61B 5/055 |
| | | | | 324/309 |
| 2018/0089863 | A1* | 3/2018 | Marschner | G06T 5/10 |
| 2018/0292495 | A1* | 10/2018 | Sun | G01R 33/5605 |
| 2019/0033412 | A1* | 1/2019 | Alsop | G01R 33/5605 |
| 2019/0265321 | A1* | 8/2019 | Alsop | G01R 33/5659 |

* cited by examiner

200 ⤵

```
Generate a set of magnetization transfer (MT) parameters associated with
substances of a tissue having different proton groups using an MT model to
produce an ultrashort echo time (UTE) MR imaging procedure of the tissue
210
```

↓

```
Acquire magnetic resonance (MR) data by applying the ultrashort time echo
(UTE) MR imaging procedure based on the generated MT parameters
220
```

↓

```
Produce a data set including quantitative values and/or images that
characterizes at least one biomarker of the tissue
230
```

```
Apply a first series of off-resonance radio frequency (RF) pulses at a first power
setting at two or more frequencies, and detect signal data from the tissue based
on the applied first series of off-resonance RF pulses
221
```

↓

```
Apply a second series of off-resonance RF pulses at a second power setting
different than that of the first series and at the two or more frequencies that are
the same as the first series, and detect signal data from the tissue based on the
applied second series of off-resonance RF pulses
223
```

┌─────────────────────────────────────────────────────────────┐
│ Fit the acquired MR data to a steady-state magnetization equation for the │
│ groups of different protons, in which the acquired MR data includes measured │
│ values from the applied first and second series of off-resonance RF pulses │
│ applied at least two saturation powers and at the two or more frequencies │
│ 231 │
└─────────────────────────────────────────────────────────────┘
┌─────────────────────────────────────────────────────────────┐
│ Apply Super-Lorentzian lineshapes and/or Gaussian lineshapes to the fitted │
│ MR data to produce the quantitative values indicative of protons of the different │
│ groups of protons (including macromolecular protons associated with the one or │
│ more substances of the tissue) │
│ 233 │
└─────────────────────────────────────────────────────────────┘

FIG. 2C

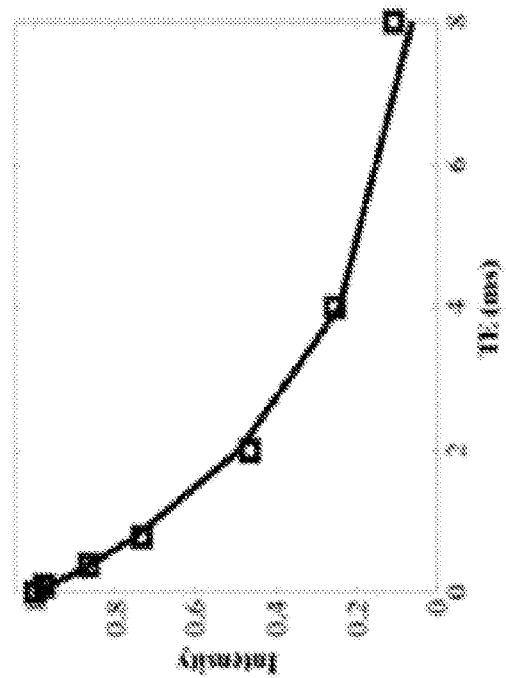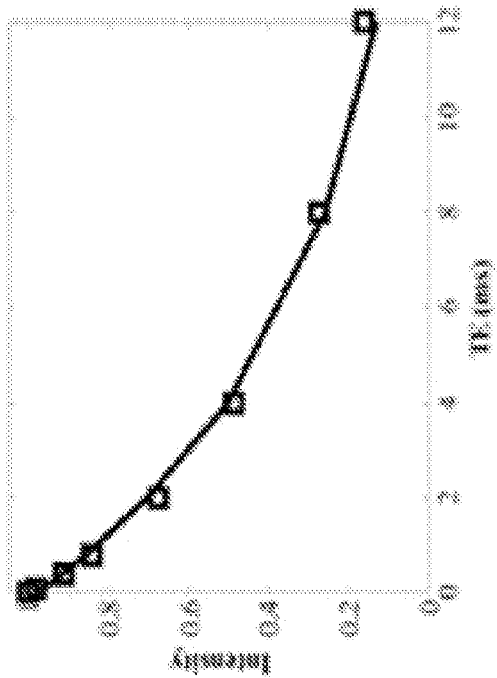
FIG. 4A
FIG. 4B
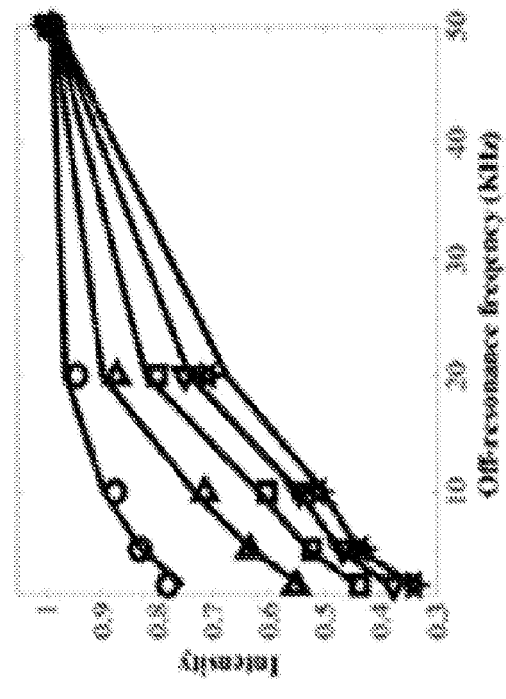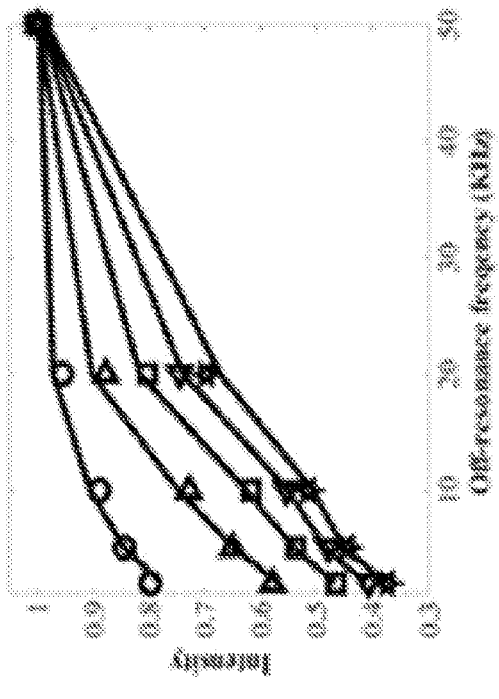

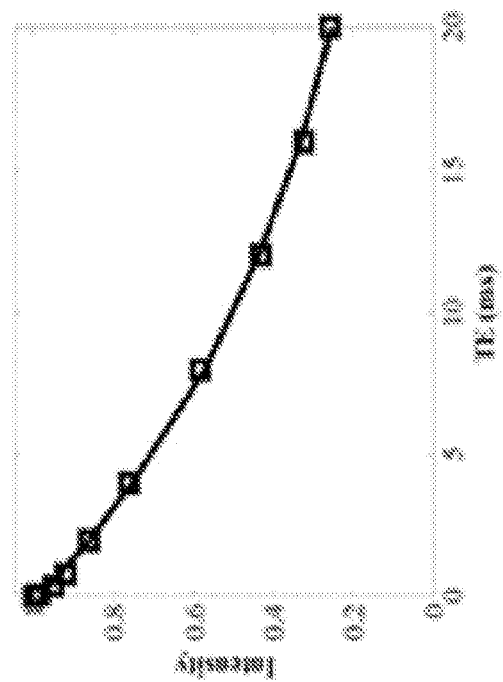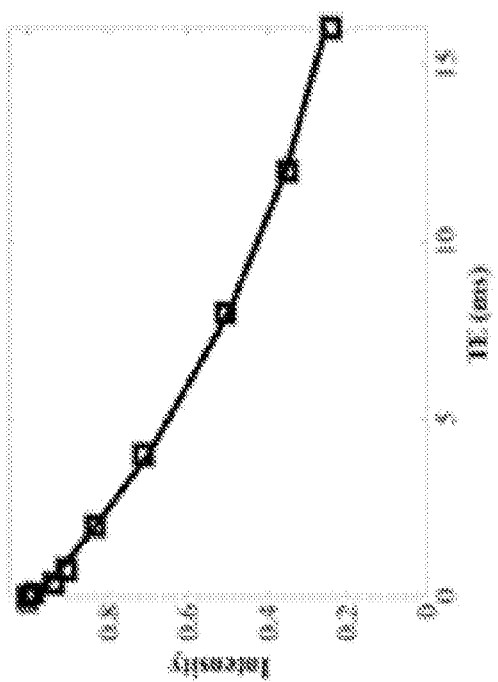
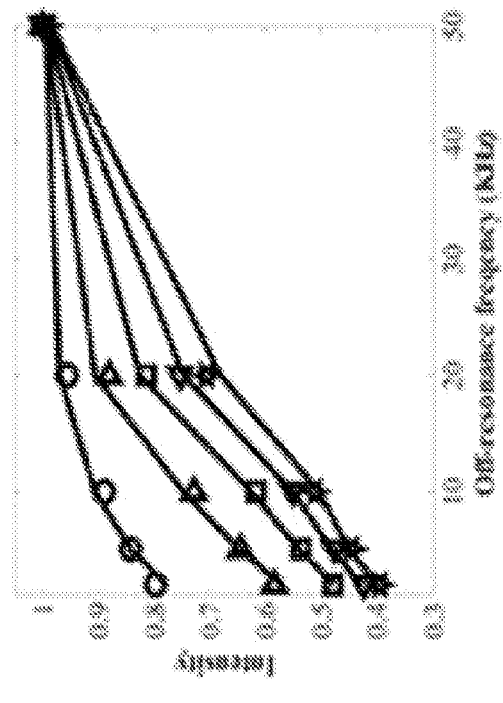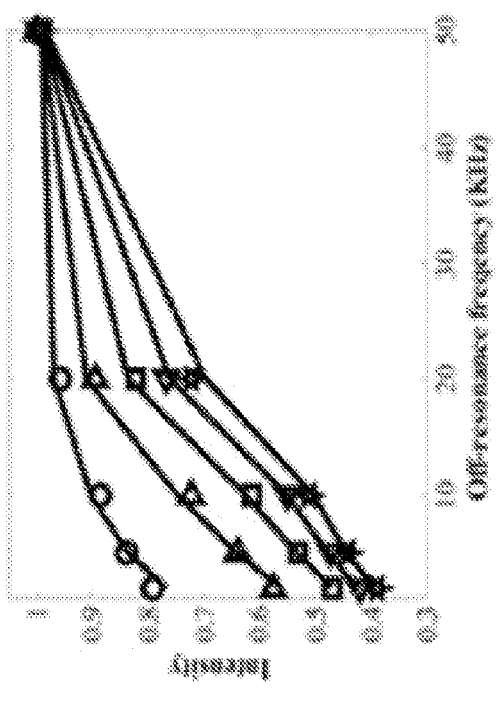
FIG. 4C
FIG. 4D

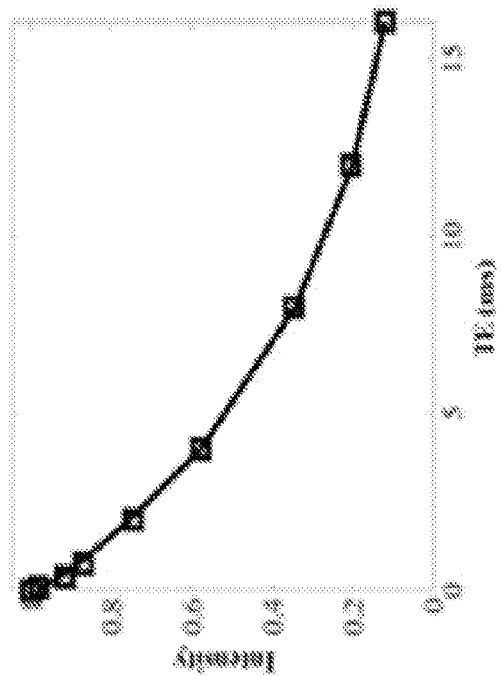
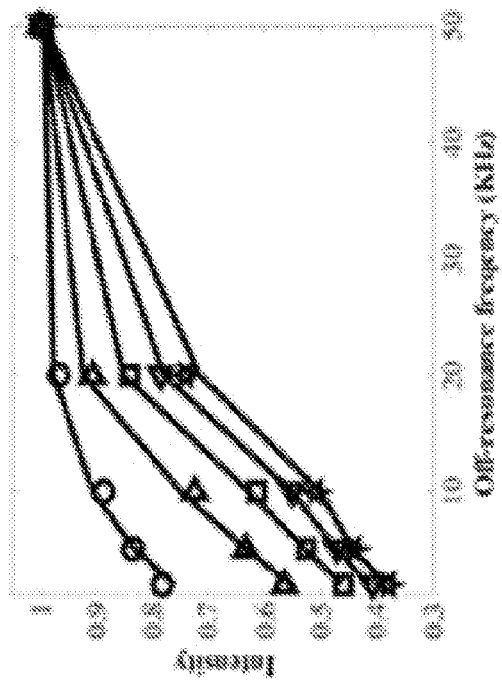
FIG. 4E
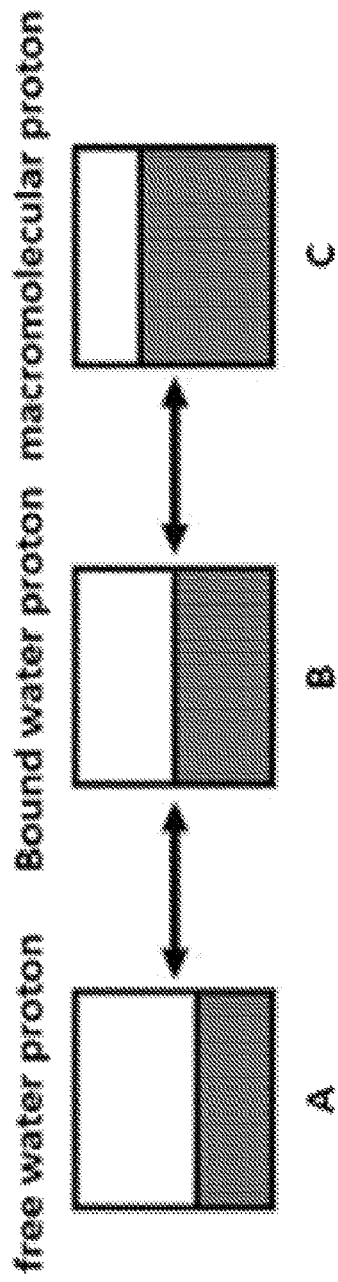
FIG. 8

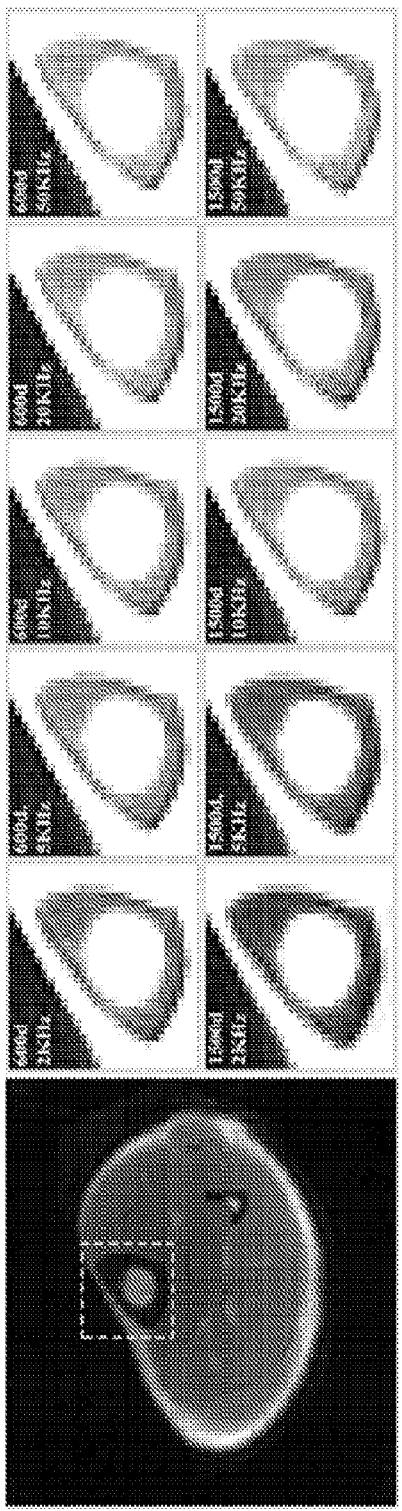
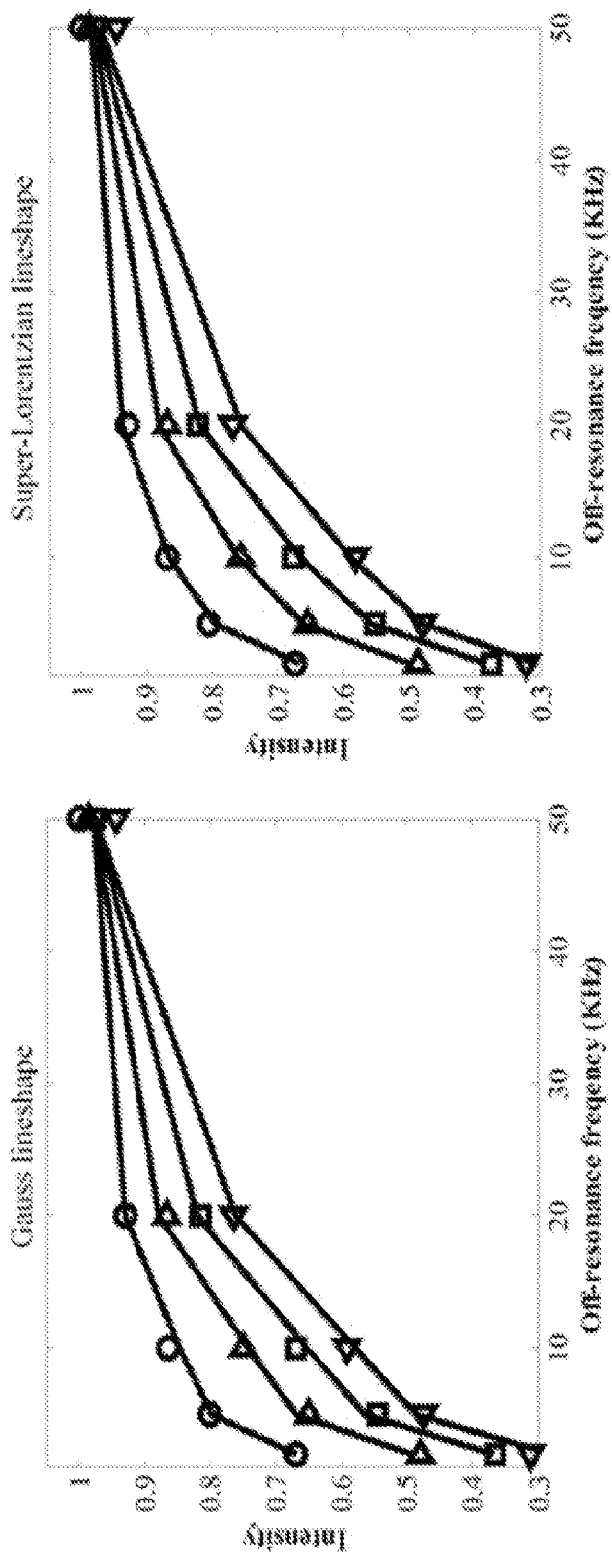
FIG. 6A
FIG. 6B
FIG. 6C

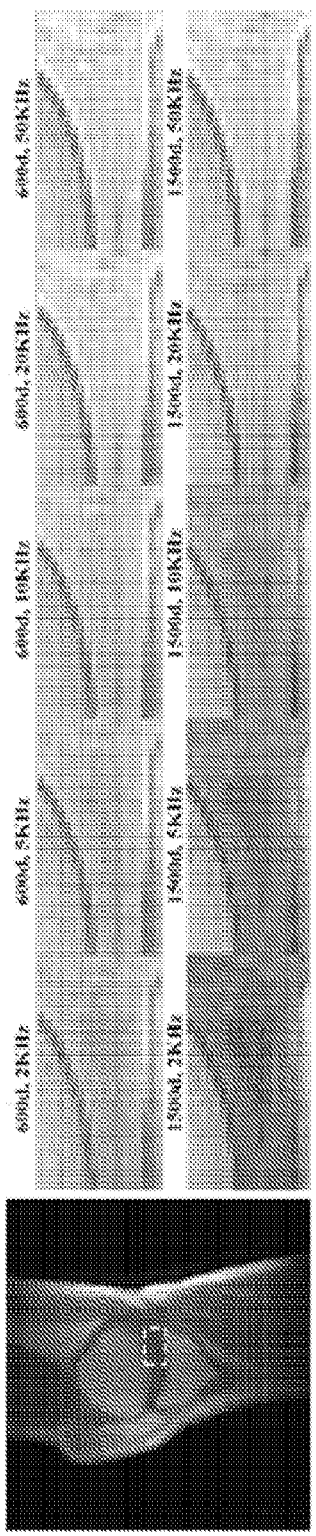
FIG 7A
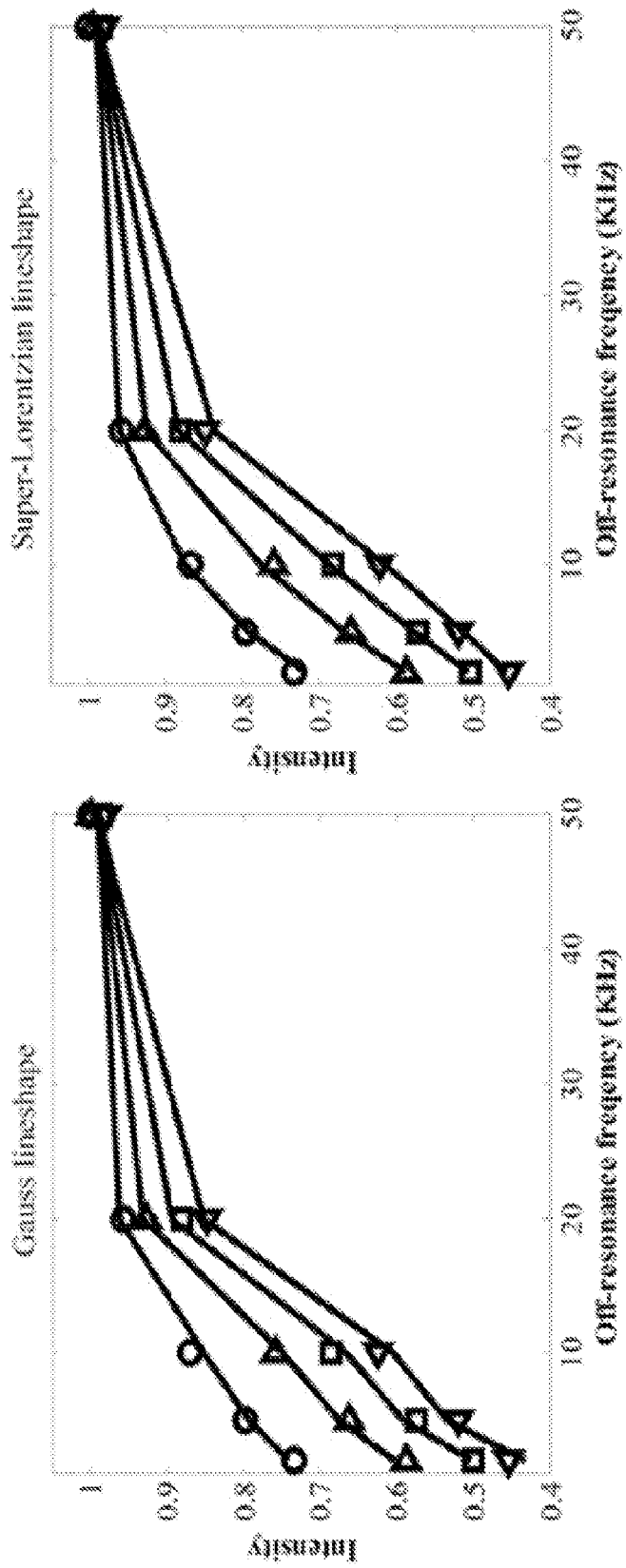
FIG. 7B
FIG. 7C

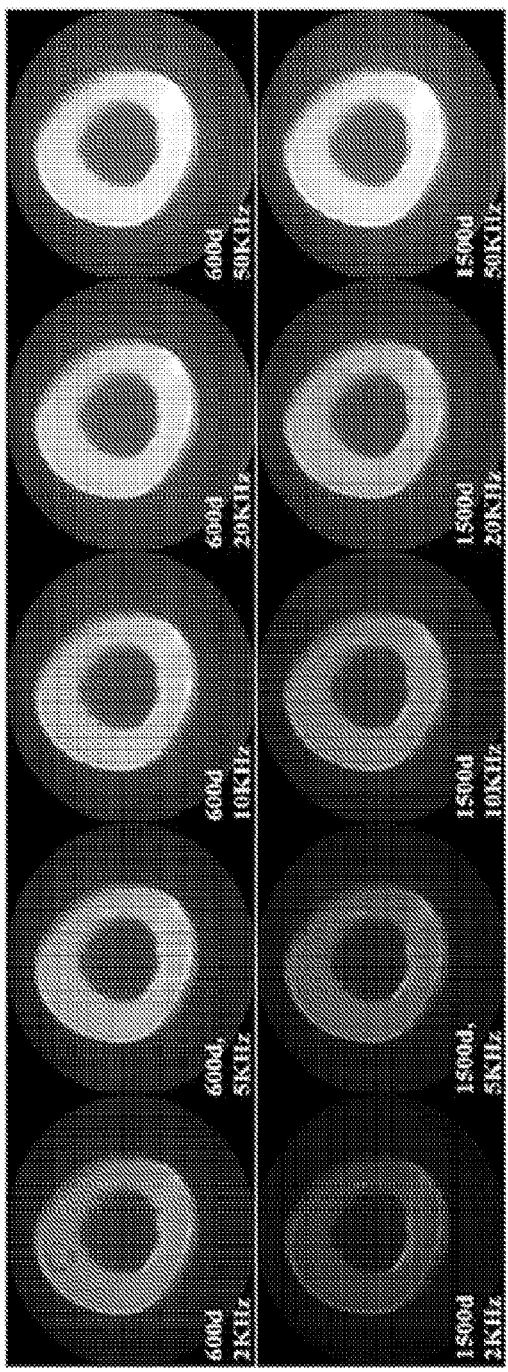
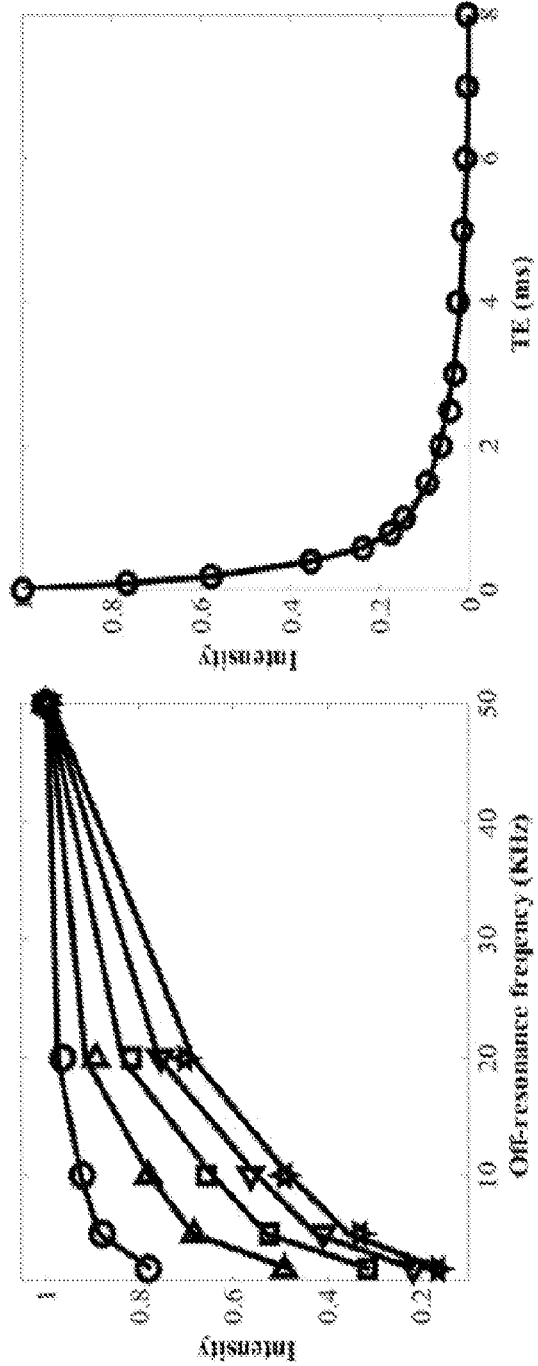
FIG. 9A
FIG. 9B
FIG. 9C

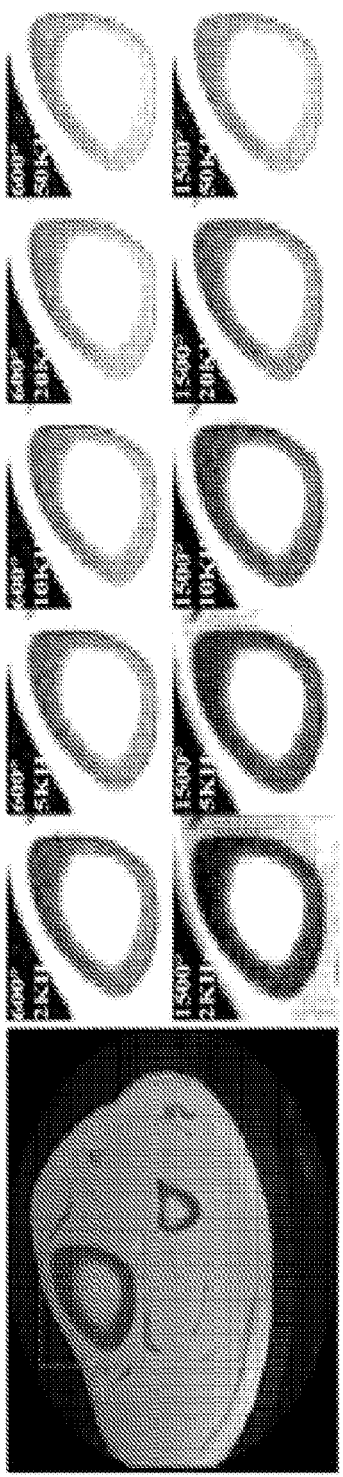
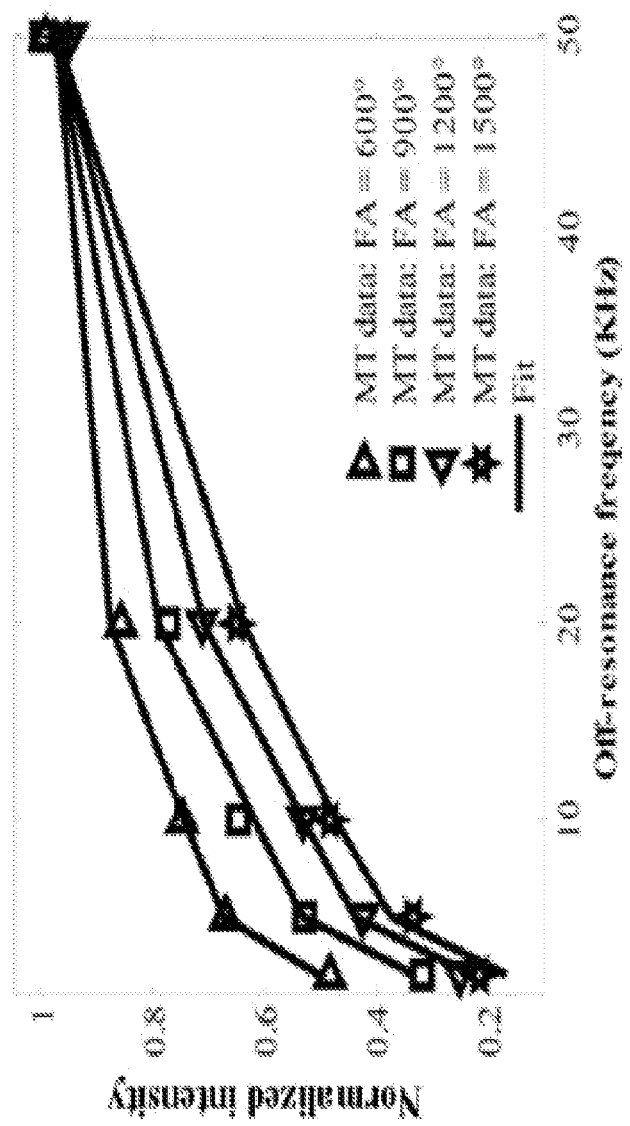
FIG. 16A
FIG. 16B

SYSTEMS AND METHODS FOR ULTRASHORT ECHO TIME MAGNETIZATION TRANSFER (UTE-MT) IMAGING AND SIGNAL MODELING

CROSS-REFERENCE TO RELATED APPLICATIONS

This patent document is a 371 National Phase Application of PCT Application No. PCT/US2017/031805 entitled "SYSTEMS AND METHODS FOR ULTRASHORT ECHO TIME MAGNETIZATION TRANSFER (UTE-MT) IMAGING AND SIGNAL MODELING" filed on May 9, 2017, which claims priority to and benefits of U.S. Provisional Patent Application No. 62/333,757 entitled "ULTRASHORT ECHO TIME MAGNETIZATION TRANSFER (UTE-MT) IMAGING AND SIGNAL MODELING" filed on May 9, 2016. The entire contents of the aforementioned patent applications are incorporated by reference as part of the disclosure of this patent document.

TECHNICAL FIELD

This patent document relates to systems, devices, and processes that use magnetic resonance imaging (MRI) technologies.

BACKGROUND

MRI is a medical imaging technique based on the magnetization properties of atomic nuclei. During an MRI imaging procedure, a magnetic field and a pulse of radio frequency (RF) energy are applied to a target such as a living subject or tissue specimen to produce an image used for imaging internal biological structures. The applied magnetic field aligns the protons that are normally randomly oriented within the water nuclei of the target being examined. This alignment is then perturbed by the applied RF pulse energy, such that the nuclei return to their resting orientations through various relaxation processes, and thereby emit RF energy which is measurable. For example, the emitted RF energy is measured according to certain time periods following the applied RF pulse. Temporal parameters, including repetition time (TR) and echo time (TE), associated with the temporal sequence of RF pulses applied and the collection of echo signal following an initial excitation pulse can be varied to create different types of MR images. Repetition time is the amount of time between successive RF pulse sequences applied to the same region of the target (e.g., same volume slice), and echo time is the time between the RF pulse delivery and the receipt of the echo signal. The measured data is processed using signal processing techniques to produce the MR images, e.g., including Fourier transformation to convert the frequency information contained in the measured signals from each location in the imaged plane to corresponding intensity levels, which are then displayed as shades of gray in a matrix arrangement of pixels.

MRI is based on the property of nuclear magnetic resonance (NMR). NMR is a physical property in which the nuclei of atoms absorb and re-emit electromagnetic energy at a specific resonance frequency in the presence of a magnetic field. The absorption and reemission of energy can be dependent on the strength of the magnetic field and the magnetic property of the atoms (e.g., atoms whose nuclei possesses magnetic spin).

SUMMARY

Techniques, systems, and devices are disclosed for ultrashort echo time magnetization transfer (UTE-MT) imaging and signal modeling to quantify the different proton groups, such as free water, bound water and macromolecule protons in short T2 tissues. Some examples of short T2 tissues or tissue components include deep radial and calcified cartilage, subchondral bone, menisci, ligaments, tendons and cortical bone. In implementations of the disclosed systems and methods, UTE-MT images with a series of MT frequency offsets and MT powers are subject to MT modeling to evaluate T1s, T2s, fractions and/or exchange rates of bound water, free water and macromolecule protons, including 2D or 3D UTE-MT MRI sequences with two-pool or three-pool modeling capable of accounting for the magic angle effect for magic angle-independent assessment of tissue properties.

In some aspects, a magnetic resonance imaging (MRI) method for characterizing a tissue includes generating a set of magnetization transfer (MT) parameters associated with one or more substances of the tissue having different proton groups using an MT model to produce an ultrashort echo time (UTE) MR imaging procedure of the tissue; acquiring magnetic resonance (MR) data from the tissue using an MRI acquisition system by applying the UTE MR data acquisition procedure based on the generated MT parameters, in which the UTE MR data acquisition procedure includes: applying a first series of off-resonance radio frequency (RF) pulses at a first power setting at two or more frequencies, detecting signal data from the tissue based on the applied first series of off-resonance RF pulses, applying a second series of off-resonance RF pulses at a second power setting different than that of the first series and at the two or more frequencies that are the same as the first series, and detecting signal data from the tissue based on the applied second series of off-resonance RF pulses; and producing a data set including one or both of quantitative values and MR images indicative of at least one biomarker of the tissue.

In some aspects, a magnetic resonance imaging (MRI) system for characterizing a tissue includes an MRI acquisition system including a magnet to generate a principal magnetic field ($B_0$), a radio frequency (RF) subsystem to apply a plurality of radio frequency pulses to the tissue and to detect an echo signal, and a gradient subsystem to apply a plurality of gradient fields to the tissue; and a data processing device in communication with the MRI acquisition system and including a processor and memory, the data processing device configured to produce an ultrashort echo time (UTE) MR imaging procedure of the tissue based on a set of magnetization transfer (MT) parameters to control the MRI acquisition system in acquiring magnetic resonance (MR) data from the tissue, and to process acquired MR data to produce a data set including one or both of quantitative values and MR images indicative of at least one biomarker of the tissue, in which the UTE MR imaging procedure produced by the data processing device includes instructions to: apply a first series of off-resonance radio frequency (RF) pulses at a first power setting at two or more frequencies, detect signal data from the tissue based on the applied first series of off-resonance RF pulses, apply a second series of off-resonance RF pulses at a second power setting different than that of the first series and at the two or more frequencies that are the same as the first series, and detect signal data from the tissue based on the applied second series of off-resonance RF pulses, in which the MT parameters are associated with one or more substances of the tissue having different proton groups.

In some aspects, a method includes using ultrashort echo time magnetization transfer (UTE-MT) imaging and signal modeling to quantify different proton groups in a short transverse relaxation time (T2) tissue including: evaluating longitudinal relaxation times, transverse relaxation times, fractions and exchange rates of the different proton groups by subjecting UTE-MT images with a series of MT frequency offsets and MT power to MT modeling; and using magic angle insensitive biomarkers to detect early structural and biochemical alterations in a tissue.

BRIEF DESCRIPTION OF THE DRAWINGS

FIG. 2A shows a diagram of an example method for quantifying different proton groups of a tissue, such as free water, bound water and macromolecule protons, using UTE-MT imaging and signal modeling in accordance with the present technology.

FIGS. 2B and 2C show diagrams of example processes of the method of FIG. 2A.

FIGS. 4A-4E show diagrams of fitted plots of example MT modeled data and multiple-TE data.

FIGS. 6A-6C show example MT modeling results of in vivo cortical bone.

FIGS. 7A-7C show example MT modeling results of in vivo meniscus.

FIG. 8 shows an example three-pool MT model, in which pool A is the free proton pool, pool B is the bound water proton pool, and pool C is macromolecular proton pool.

FIGS. 9A-9C show example 3-pool MT modeling results of bovine cortical bone.

FIG. 16A shows example UTE-MT images from in vivo human cortical bone.

FIG. 16B shows fitting curves for cortical bone signal intensity versus off-resonance frequency for multiple MT flip angles.

DETAILED DESCRIPTION

Figure 1:
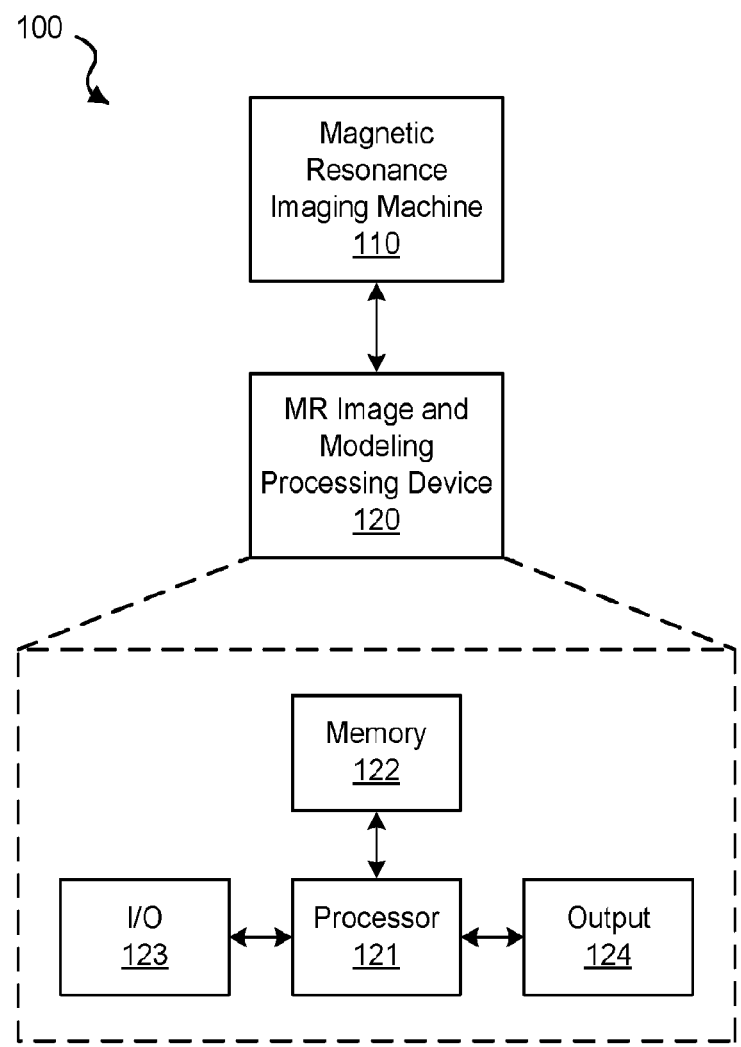
FIG. 1 shows an example embodiment of an MR ultrashort echo time magnetization transfer (UTE-MT) imaging and signal modeling system in accordance with the present technology.

Over the past several decades, extensive research has been performed on the use of magnetic resonance (MR) imaging biomarkers for the evaluation of tissues. Tissue can be characterized by different relaxation times, referred to as longitudinal relaxation time (T1) and transverse relaxation time (T2). T1 is a time constant that determines the rate at which excited protons return to equilibrium. For example, T1 is a measure of time for spinning protons to realign with the external magnetic field applied to the tissue. T2 is a time constant that determines the rate at which excited protons reach equilibrium or go out of phase with each other. For example, T2 is a measure of the time taken for spinning protons to lose phase coherence among the nuclei spinning perpendicular to the main field.

MR imaging of biomarkers has been quite effective in studying musculoskeletal tissue integrity, including research focused on early osteoarthritis and osteoporosis. T2, T2* and $T1_{rho}$ are among the most widely studied parameters with respect to musculoskeletal biomarkers, and both have been linked to alterations in the macromolecular structure of cartilage. For example, many studies show that T2 is sensitive to collagen matrix degradation, while $T1_{rho}$ is sensitive to proteoglycan (PG) depletion. Although nearly all commercial MRI systems currently have standard packages that include measurements of transverse relaxation times, their routine clinical use remains limited. This is largely due to the uncertainty in the interpretation of values generated with these quantitative techniques, and a principal confounding factor is the so-called magic angle effect.

The magic angle effect is caused by changes in dipole-dipole interactions, which are minimized when tissue fiber orientation approaches 54.7° relative to the main magnetic field. The large orientational dependence of $T_2$ relaxation time in anisotropic, collagen-rich tissues has been known for more than half a century. With regards to hyaline articular cartilage, the magic angle effect is most pronounced in the regions of greatest anisotropy, such as the middle layer, with significantly reduced magic angle effect in the superficial layers. For instance, studies have shown that both the $T_2$ and $T_2^*$ values of the superficial layer of femoral condyle cartilage obtained on clinical systems can vary by nearly 10 ms depending on the sampled location in young, asymptomatic adult volunteers. Considering that the values in these studies for the superficial layer ranged from ~45-55 ms for $T_2$ and ~20-50 ms for $T_2^*$, these spatial variations account for a significant proportion of the total measurement. Furthermore, when the amount of variability in these reference values are compared with those obtained from histologically evaluated cartilage specimens, where mean differences in $T_2$ and $T_2^*$ of normal versus degenerated cartilage specimens also ranges from ~5-10 ms, it is clear that the magic angle effects rival the expected relaxation changes related to biochemical alteration and tissue compromise. In fact, previous authors have estimated that approximately 60% of the depth-wise variation of $T_2$ in human cartilage is accounted for by changes in collagen anisotropy. Studies that have investigated $T_{1rho}$ using traditional, continuous wave spin-lock pulses in cartilage have found similar results, whereby dipolar interaction is the dominant relaxation mechanism and therefore measurements are exquisitely sensitive to the magic angle effect. For example, much greater increase (e.g., up to 2-folds) in T2, T2* and $T1_{rho}$ have been observed for the middle and deep layers of articular cartilage when the sample fibers are oriented from 0° to 54.7° relative to the main magnetic field. The magic angle induced increase in T2, T2* and $T1_{rho}$ is far more than the typical increase of 10-30% due to degeneration.

In recent years, ultrashort echo time (UTE) sequences have been used to study tissues or tissue components with short transverse relaxation times, which result in little or no signal when imaged using conventional MR sequences. Tendon is one example of such tissue, where the highly anisotropic structure of collagen and relatively low hydration results in short mean transverse relaxation time. The magic angle effect has a proportionally larger impact on these highly anisotropic tissues, and authors have shown a 37-fold increase in $T_2$, 10-fold increase in UTE-$T_2^*$, and 7-fold increase in UTE-$T_{1rho}$ with tendon specimen orientation from 0° to 55° relative to the main magnetic field. Use of the UTE sequence shows promise in that it allows for signal detection and quantification of otherwise "invisible" tendon when imaged using clinical MR sequences. However, the need for the development and validation of less magic angle dependent MR biomarkers is clear.

Magnetization transfer (MT) is a MRI technique that generates contrast based on the exchange of magnetization (including chemical exchange or cross-relaxation) between groups of spins characterized by different molecular environments. In biological tissues, two or more molecular environments of protons can be identified, e.g., those in water (referred to as water, pool) and those in large molecules (referred to as semisolid or macromolecular, pool). In a simplified two-pool model, for example, only water protons and macromolecular protons are considered. In a more complicated three-pool model, for example, the water protons are divided into two pools, including free water with slower relaxation or longer relaxation time, and water bound to macromolecules with fast relaxation or shorter relaxation time. MT provides quantifiable information about the very short T2 components of tissues, including their water component (e.g., both free water and bound water may be "invisible" with conventional clinical MR sequences) and macromolecular component (e.g., macromolecular protons have extremely short T2 and are "invisible" with all current MRI sequences including UTE sequences, and can only be evaluated indirectly via UTE-MT imaging and signal modeling).

MT effects in tissues are typically reported in terms of MT ratio (MTR), by selective saturation of the semisolid pool with an off-resonance RF pulse, which provide maps of the percent decrease in the MRI signal. For example, investigations have shown that the MTR values in tissues are changed with many diseases in central nervous system (CNS) and musculoskeletal system, such as multiple sclerosis and Charcot-Marie-Tooth. However, the MTR measurements are inherently semi-quantitative, which reflects a complex combination of biological and experimental parameters.

Disclosed are methods and systems for ultrashort echo time magnetization transfer (UTE-MT) imaging and signal modeling to quantify the different proton groups, such as free water, bound water and macromolecule protons in short $T_2$ tissues, e.g., including but not limited to the deep radial and calcified cartilage, subchondral bone, menisci, ligaments, tendons and cortical bone. UTE-MT images with a series of MT frequency offsets and MT power are subject to MT modeling to evaluate $T_1$s, $T_2$s, fractions and exchange rates of bound water, free water and macromolecule protons. Example implementations of the disclosed systems and methods include studies that investigate the use of the two-dimensional (2D) and three-dimensional (3D) ultrashort echo time magnetization transfer (2D and/or 3D UTE-MT) sequences with two-pool and/or three-pool modeling for the potential magic angle independent assessment of tissue properties.

Fractions and exchange rates of bound water, free water and macromolecule protons are insensitive to the magic angle effect, which is the major confounding factor using current biomarkers (such as $T_2$, $T_2^*$ and $T_{1rho}$) to evaluate tissue degeneration. For example, $T_2$, $T_2^*$ and $T_{1rho}$ can be increased by more than 100% when the collagen fibers are oriented 54° relative to the external magnetic ($B_0$) field than when parallel to the $B_0$ field. Meanwhile, degeneration leads to a few percent to several tens of percent increase in $T_2$, $T_2^*$ and $T_{1rho}$.

For example, the magic angle insensitive biomarkers, such as fractions and exchange rates of bound water, free water and macromolecule protons, can be used to detect early structural and biochemical alterations in musculoskeketal tissues, and may have a major impact on the diagnosis and monitoring of osteoarthritis (OA), osteoporosis (OP), tendon diseases, muscle diseases, and many other diseases.

FIG. 1 shows an example embodiment of an MR ultrashort echo time magnetization transfer (UTE-MT) imaging and signal modeling system 100 for providing a quantitative, noninvasive measure and evaluation of different proton groups associated with target biomarkers in imaged tissue, e.g., in a living patient subject or tissue sample. FIG. 1 shows one aspect of the example system 100 that includes a magnetic resonance imaging (MRI) machine 110 in communication with an MR image and modeling processing device 120, e.g., which can be used to control the MRI machine and analyze obtained data to affect the image data collecting protocol to produce quantitative data of the target biomarkers.

The MRI machine 110 can be used in the system 100 to implement a MRI-based characterization process under the control of the example MR image and modeling processing device 120. MRI machine 110 can include various types of MRI systems, which can perform at least one of a multitude of MRI scans that can include, but are not limited to, T1-weighted MRI scans, T1ρ MRI scans, T2-weighted MRI scans, T2*-weighted MRI scans, spin (proton ($^1$H)) density weighted MRI scans, diffusion tensor (DT) and diffusion weighted imaging (DWI) MRI scans, magnetization transfer (MT) MRI scans, real-time MRI, functional MRI (fMRI) and related techniques such as arterial spin labeling (ASL), among other MRI techniques.

The MR image and modeling processing device 120 can include a processor 121 that can be in communication with a memory unit 122, an input/output (I/O) unit 123, and/or an output unit 124. The MR image and modeling processing device 120 can be implemented as one of various data processing systems, such as a personal computer (PC), laptop, and mobile computing device such as a smartphone, tablet and/or wearable computing device. In some implementations, the MR image and modeling processing device 120 is embodied on one or more computing devices in a computer system or communication network accessible via the Internet (referred to as "the cloud"), e.g., including servers and/or databases in the cloud.

The processor 121 is configured to process data, and the memory unit 122 is in communication with the processor 121 to store and/or buffer the data. To support various functions of the MR image and modeling processing device 120, the processor 121 can be included to interface with and control operations of other components of the MR image and modeling processing device 120, such as the I/O unit 123 and/or the output unit 124. The processor 121 can include one or more processors, e.g., including but not limited to microprocessors such as a central processing unit (CPU), microcontrollers, or the like.

The memory unit 122 can include and store processor-executable code, which when executed by the processor, configures the MR image and modeling processing device 120 to perform various operations, e.g., such as receiving information, commands, and/or data, processing information and data, and transmitting or providing information/data to another device. The memory unit 122 can store other information and data, such as instructions, software, values, images, and other data processed or referenced by processor 121. For example, various types of Random Access Memory (RAM) devices, Read Only Memory (ROM) devices, Flash Memory devices, and other suitable storage media can be used to implement storage functions of memory unit 122. The memory unit 122 can store MRI data and information, which can include subject MRI image data including spatial and spectral data, MRI machine system parameters, data processing parameters, and processed parameters and data that can be used in the implementation of UTE-MT imaging and signal modeling techniques in accordance with the disclosed technology. The memory unit 122 can store data and information that can be used to implement a MRI-based UTE-MT imaging and signal modeling characterization method, and store data and information that can be generated from a MRI-based UTE-MT characterization algorithm and model.

In some implementations, the MR image and modeling processing device 120 includes an input/output unit (I/O) 123 to interface the processor 121 and/or memory unit 122 to other modules, units or devices associated with the system 100, and/or external devices. The I/O unit 123 can connect to an external interface, source of data storage, or display device. Various types of wired or wireless interfaces compatible with typical data communication standards, such as Universal Serial Bus (USB), IEEE 1394 (FireWire), Bluetooth, Bluetooth low energy (BLE), ZigBee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces, can be used to implement I/O unit 123. In some implementations, for example, the MR image and modeling processing device 120 includes a wireless communications unit, e.g., such as a transmitter (Tx) or a transmitter/receiver (Tx/Rx) unit. The I/O unit 123 can interface the processor 121 and memory unit 122 with the wireless communications unit to utilize various types of wireless interfaces, such as the examples described above. The I/O unit 123 can interface with other external interfaces, sources of data storage, and/or visual or audio display devices, etc. to retrieve and transfer data and information that can be processed by the processor 121, stored in the memory unit 122, or exhibited on an output unit of a user device (e.g., display screen of a computing device) or an external device.

To support various functions of the MR image and modeling processing device 120, the output unit 124 can be used to exhibit data implemented by the example device 120. The output unit 124 can include various types of display, speaker, or printing interfaces to implement output functionalities the system 100. In some embodiments, for example, the output unit 124 can include cathode ray tube (CRT), light emitting diode (LED), or liquid crystal display (LCD) monitor or screen as a visual display. In some examples, the output unit 124 can include toner, liquid inkjet, solid ink, dye sublimation, inkless (such as thermal or UV) printing apparatuses to implement some output modalities of the output unit 124. In some examples, the output unit 124 can include various types of audio signal transducer apparatuses. The output unit 124 can exhibit data and information, such as patient diagnostic data, MRI machine system information, partially processed MRI-based UTE-MT characterization processing information, and/or fully-processed MRI-based UTE-MT characterization processing information.

FIG. 2A shows a diagram of an example method for quantifying different proton groups, such as free water, bound water and macromolecule protons using ultrashort echo time magnetization transfer (UTE-MT) imaging and signal modeling to characterize a tissue from acquired MR data. Exemplary methods to quantify proton groups and their properties and characterize the target tissue using the disclosed UTE-MT MRI techniques can be performed using the system 100 shown in FIG. 1. Examples of the tissue include short T2 tissues such as musculoskeletal tissue including but not limited to cortical bone, ligaments, tendons, menisci, etc.

The method 200 includes a process 210 to generate a set of MT parameters associated with one or more substances having different proton groups using an MT model. The generated MT parameters can be used to produce a UTE-MT MR imaging protocol of a target tissue, e.g., of a patient subject or tissue sample. In some implementations of the process 210, for example, the MT model is used to map T1s, T2s, exchange rates and/or fractions of bound water, total water and macromolecules, e.g., based on contrast or identifiable differences in the exchange of magnetization between groups of spins characterized by different proton groups found in substances (e.g., free water, bound water and macromolecules). In some implementations, the generated MT parameters can be used as intermediary parameters to determine setting parameters of the UTE-MR imaging protocol and/or used in calculations performed in subsequent data processing of acquired MR data from the target tissue.

In some implementations of the process 210 for a two-pool quantitative MT model, the generated MT parameters include:

fraction of water (f);

$T_2$ of macromolecule protons ($T_{2m}$);

exchange rate parameter $RM_{0m}$, where R is the first-order magnetization exchange rate constant, and $M_{0w}$ is the fully relaxed magnetization of water;

recovery rate of longitudinal magnetization of water ($R_w$); and

Residual (%).

In some implementations, for example, the MT model includes a three-pool MT model. For example, in the three-pool models, three pools include a free water pool composed of protons in water which can freely move; a bound water pool composed of protons in water bound to macromolecules with reduced mobility; and a semisolid pool that includes backbone macromolecular protons. The example parameters include denotations A, B, and C that correspond to the three pools: (A) free water pool; (B) bound water pool; and (C) semisolid pool.

In some implementations of the process 210 for a three-pool quantitative MT model, the generated MT parameters include physical parameters including $M_0^A$, $T_2^{A,B,C}$, $k_{AC}$, $k_{BC}$, $k_{AC}$, $R_{A,B,C}$, f, g, such as twelve example parameters below:

$T_2$ of free water ($T_{2A}$);

$T_2$ of bound water ($T_{2B}$);

$T_2$ of macromolecule protons ($T_{2C}$);

fraction of free water ($f_A$);

fraction of bound water ($f_B$);

fraction of macromolecule protons ($f_C$);

exchange rate from free water to bound water ($R_{AB}$);

exchange rate from bound water to macromolecule ($R_{BC}$);

recovery rate of longitudinal magnetization of free water ($R_A$);

recovery rate of longitudinal magnetization of bound water ($R_B$);

recovery rate of longitudinal magnetization of macromolecule protons ($R_C$); and Residual (%).

In some implementations of a two-pool MT model, the MT pulse are treated as a rectangular continuous wave signal with the same mean saturating power as the experimentally used shaped pulse in each repetition time to approximate a continuous wave power equivalent (CWPE), in which the ($w_{CWPE}$) angular frequency of precession induced by the off-resonance MT pulse ($w_{CWPE}$) is a measure of the amplitude of the $B_1$ field, represented by Equation [A1]

$$w_{CWPE} = \frac{\theta_{sat}\pi}{p_1 180°}\sqrt{\frac{p_2}{\tau_{sat}TR}}, \quad [A1]$$

where $\theta_{sat}$ is the flip-angle of MT pulse; $p_1$ is the ratio of the area of the MT pulse to a rectangular pulse of the same duration and peak amplitude and $p_2$ is the ratio of the square of the MT pulse area to the square of the area of the same rectangular pulse; $\tau_{sat}$ is the duration of the MT pulse; and TR is the time interval between adjacent two MT pulses. The $w_{CWPE}$ value can be used in calculations performed in subsequent data processing after experimental MR data has been acquired from the target tissue (e.g., subject or sample).

The method 200 includes a process 220 to apply the ultrashort echo time (UTE) MR imaging procedure to acquire MR signal data from a desired target based on the generated MT parameters, in which the applied UTE-MT MR imaging procedure includes a series of off-resonance RF pulses at varying frequencies (referred to as MT frequency offsets). In some embodiments of the method 200, the process 220 includes repeating the acquiring of MR data by applying at least a second UTE-MT MR imaging procedure using a series of off-resonance RF pulses at the set of MT frequency offsets at a different MT power than that of a first series of off-resonance RF pulses.

FIG. 2B shows a diagram of an example embodiment of an UTE-MT MR imaging procedure applied at the process 220. For example, the process 220 can include a process 221 to apply a first series of off-resonance radio frequency (RF) pulses at a first power setting at two or more frequencies, and to detect signal data from the tissue based on the applied first series of off-resonance RF pulses. The process 220 can include a process 223 to apply a second series of off-resonance RF pulses at a second power setting different than that of the first series and at the two or more frequencies that are the same as the first series, and to detect signal data from the tissue based on the applied second series of off-resonance RF pulses.

In some example implementations, the process 220 can be repeated multiple times, e.g., five times. In one example, the MT frequency offsets of the off-resonance RF pulses includes and two or more saturation powers in a range of 300° to 1500° (e.g., two or more saturation powers among 300°, 600°, 900°, 1200° and 1500°), applied at two or more MT frequency offsets from a range of 2 kHz to 50 kHz (e.g., two or more frequencies among 2, 5, 10, 20 and 50 kHz), such that the process 220 acquires a total of at least 4 different MT datasets. For example, the MT frequency offsets of the off-resonance RF pulses can includes two saturation powers of 300° and 900° applied at two frequencies 2 kHz and 20 kHz, or at three frequencies 2 kHz, 5 kHz and 20 kHz. In some implementations, the process 220 is performed at multiple orientations of the target.

In another example, the MT frequency offsets of the off-resonance RF pulses includes five MT frequency offsets (e.g., 2, 5, 10, 20 and 50 kHz) and five saturation powers (e.g., 300°, 600°, 900°, 1200° and 1500°), such that the process 220 acquires a total of 25 different MT datasets. For example, the process 220 can be performed at multiple orientations of the target (e.g., 0°, 30°, 55°, 70° and 90° relative to the $B_0$ field).

Generally for an MR imaging procedure, a magnetic field ($B_0$ field) is applied at the target tissue, which causes protons of different substances (e.g., free water, bound water and macromolecules) to align with the applied $B_0$ field. In general, it is understood that the stronger the $B_0$ field, the more protons will align, and thereby a stronger potential MR signal is detectable. Following the applied $B_0$ field, an RF pulse is applied after which a gradient pulse or series of gradient pulses is applied, to immediately follow the RF pulse, to excite and generate a spatial encoding. For example, UTE MR imaging, the gradient pulse or pulses can be 30 μs to 60 μs after the RF pulse. In some implementations, the UTE pulses can be less than 30 μs, such as 16 μs. By applying the UTE MR data acquisition procedure in the process 220, MR signal data from fast relaxation tissue like bone, ligaments, tendons, etc. can be obtained and processed to characterize the target tissue.

In some implementations, the process 220 can include acquiring MR data by applying a 2D or 3D UTE-MT sequence on the target volume using an MRI system such as MRI machine 110 (e.g., a clinical 3T Signa TwinSpeed scanner, GE Healthcare Technologies) configured to apply the magnetic and RF fields in accordance with the UTE-MT sequence. The MR signals are collected on a MR coil, and received and processed at a data processing system such as the MR image processing device 120. In some implementations, the UTE-MT sequence includes a short non-selective hard pulse (e.g., duration=32 µs) excitation followed by 2D radial ramp sampling with a minimal nominal TE, e.g., of 8 µs. The applied UTE-MT sequence, e.g., in accordance with the MT preparation, can include a Fermi shaped RF pulse (e.g., duration of 8 ms) followed by a gradient crusher.

In some examples, the UTE-MT imaging protocol can include applying a sequence of off-resonance RF pulses based on the following parameters in accordance with the generated MT parameters from the process 210. For example, TR=50 ms, TE=8 µs, Flip angle=5°, FOV=5×5 cm², matrix=256×256; five MT powers (e.g., 300°, 600°, 900°, 1200° and 1500°) and five MT frequency offsets (e.g., 2, 5, 10, 20 and 50 kHz), with a total of 25 different MT datasets. The same UTE-MT protocol can be applied to the target a certain multiple of times (e.g., five times), including at the target at varying orientations (e.g., the sample oriented 0°, 30°, 55°, 70° and 90° relative to the $B_0$ field). Multiple TE data can also be acquired with these five angle orientations for mono-exponential fitting to determine $T_2^*$ value of the water component. The example protocol for multiple-TE data acquisition can be identical with the UTE-MT protocol, except that a non-MT pulse can be used (e.g., with TEs were 0.008, 2, 4, 8, 12, 16, 20 ms).

The method 200 includes a process 230 to produce a data set including quantitative values and/or images that characterizes one or more biomarkers of the target tissue. The process 230 includes fitting the acquired MR data with a variety of saturation powers and off-resonance frequencies Δf, including characterizing the protons in the macromolecular pool by applying Super-Lorentzian lineshapes, to produce the data set including final parameters that provide information about the biomarkers in the target tissue. In some implementations, the final parameters include:

proton fraction parameters, e.g., f, the macromolecular proton fraction, where $$f = \frac{M_{0m}}{M_{0m} + M_{0w}}$$

($M_{0m}$ and $M_{0w}$ are the fully relaxed magnetization of macromolecular pool and water pool, respectively.);

relaxation time parameters, e.g., $T_{2m}$; and exchange rate parameters, e.g., $RM_{0m}$, where R is the first-order magnetization exchange rate constant between the two pools, and $M_{0m}$ and $M_{0w}$ are the fully relaxed magnetization of macromolecular pool and water pool, respectively.

For example, in some implementations, the acquired data with a variety of saturation powers and off-resonance frequencies Δf were fitted based at least in part on Equation [A2], where the signal intensity S is given by:

$$S = gM_{0w} \frac{R_{1m}\left[\frac{RM_{0w}f}{R_{1w}(1-f)}\right] + R_{RFm} + R_{1m} + RM_{0w}}{\left[\frac{RM_{0w}f}{R_{1w}(1-f)}\right](R_{1m} + R_{RFm}) + \left(1 + \left[\frac{w_{CWPE}}{2\pi\Delta f}\right]^2 \left[\frac{1}{R_{1w}T_{2w}}\right]\right)(R_{RFm} + R_{1m} + RM_{0w})} \quad [A2]$$

where g is a amplitude scaling factor of the acquired data; f is the macromolecular proton fraction, i.e.

$$f = \frac{M_{0m}}{M_{0m} + M_{0w}};$$

$M_{0m}$ and $M_{0w}$ fully relaxed magnetization of macromolecular pool and water pool respectively; $R_{1m}$ and $R_{1w}$ are the longitudinal rate constants, respectively; R is the first-order magnetization exchange rate constant between the two pools; $R_{RFm}$ is the loss rate of longitudinal magnetization of macromolecular pool due to the RF saturation of the MT pulse. $R_{RFm}$ is related to the absorption lineshape $G(2\pi\Delta f)$ of the spins in the macromolecular pool, which is given by Equation [A3]:

$$R_{RFm} = \pi w_{CWPE}^2 G(2\pi\Delta f) \quad [A3]$$

The super-Lorentzian expression can be expressed by Equation [A4]:

$$G(2\pi\Delta f) = \int_0^{\pi/2} d\theta \sin\theta \sqrt{\frac{2}{\pi}} \frac{T_{2m}}{|3\cos^2\theta - 1|} \exp\left(-2\left[\frac{2\pi\Delta f T_{2m}}{|3\cos^2\theta - 1|}\right]^2\right) \quad [A4]$$

where θ is the angle orientation between the axis of molecular orientation and the $B_0$.

In some implementations, independent variables of Equation [A2] are $gM_{0w}$, $RM_{0w}$, $f/[R_{1w}(1-f)]$, $1/(R_{1w}T_{2w})$, $T_{2m}$, in which these variables are used to obtain the final parameters associated with the biomarkers based on the fitting of the acquired MR data. In some implementations, the residual parameter can be determined based on the following, e.g., residual of fitting represented by $$\text{Residual} = \sqrt{\frac{\sum_i (S_{i,fit} - S_i)^2}{\sum_i S_i^2}},$$

where $S_i$, $S_{i,fit}$ (i=1, . . . , N, N is the total number of data points in one MT datasets) are the experimental and fitted data points. In some implementations, for example, if the apparent longitudinal relaxation rate $R_{1obs}$ (=1/$T_1$), which can be measured by a conventional $T_1$ measurement sequence such as multiple-TR UTE protocol mentioned above, is known, $R_{1w}$ is determined by:

$$R_{1w} = \frac{R_{1obs}}{1 + \frac{\frac{RM_{0w}f}{R_{1w}(1-f)}(R_{1m} - R_{1obs})}{(R_{1m} - R_{1obs}) + RM_{0w}}} \quad [A5]$$

FIG. 2C shows a diagram of an example embodiment the process 230. In some implementations, the process 230 includes a process 231 to fit the acquired MR data to a steady-state magnetization equation for the groups of different protons, e.g., in which the acquired MR data includes measured values from the detected signals associated with the applied first and second series of off-resonance RF pulses applied at the first and second power settings and at the two or more frequencies. The process 230 includes a process 233 to apply at least one of Super-Lorentzian lineshapes or Gaussian lineshapes to the fitted MR data to produce the quantitative values indicative of protons of the different proton groups including macromolecular protons associated with the one or more substances of the tissue. For example, the produced data set includes final parameters that provide information about the one or more biomarkers of the tissue. In some implementations, for example, the final parameters include a macromolecular proton fraction, a relaxation time parameter, and an exchange rate parameters ($RM_{0m}$), where R is a first-order magnetization exchange rate constant between at least two pools, and $M_{0m}$ and $M_{0w}$ are fully relaxed magnetization of a macromolecular pool and a water pool, respectively.

In some implementations, the steady-state magnetization equation includes a steady-state longitudinal magnetization of two pools of proton groups (pool A and pool B, e.g., water and macromolecular proton pools), such as:

$$S = M_z^A e^{-TE/T2A} + M_z^B e^{-TE/T2B}$$

where $T2^A$ and $T2^B$ are the T2 value of pools A and B; and TE is the echo time. It is noted that the steady-state magnetization can be written in many forms, e.g., as in other examples described herein. In some implementations, the steady-state magnetization equation includes a steady-state longitudinal magnetization of three pools of proton groups (e.g., a free pool A, composed of mobile protons; a bound water pool B, composed of water protons bound to macromolecules, and a semisolid pool C, which includes macromolecular protons).

The example method 200 can implement the processes 210, 220, and 230 in the order shown in FIG. 2A, or in other orders not expressly shown in the exemplary figure in accordance with other embodiments of the methods described herein.

Example Implementations

Example implementations of the method 200 are described.

UTE imaging can be used to image tissues with short T2 relaxation time. The present technology includes applying UTE imaging with and without off-resonance saturation (UTE-OSC). For example, the subtraction of UTE images without and with off-resonance saturation pulse can provide high contrast images of short T2 tissues or tissue components. The UTE-OSC technique also allows assessment of magnetization transfer ratio (MTR) in short T2 tissues. This is an advantage over conventional MT sequences, which can only provide MTR for long T2 tissues.

MT modeling has been used in conventional MT imaging sequences, which allows for quantitative assessment of T1s, T2s, exchange rates and fractions of water and macromolecule protons in long T2 tissues such as white matter, muscle and superficial articular cartilage. UTE sequences can detect signal from short T2 tissues or tissue components such as cortical bone, menisci, ligaments, tendons, myelin in white matter, etc. The disclosed systems and methods include UTE-MT imaging and modeling techniques to map T1s, T2s, exchange rates and fractions of bound water, total water and macromolecules in short T2 tissues or tissue components.

In some implementations, UTE-MT modeling can be utilized on UTE-MT images acquired with a series of MT power and off-resonance frequency offsets. Example two-pool and three-pool UTE-MT modeling techniques can be used, for example, on cortical bone, meniscus, ligaments and tendons, which provide excellent results. Moreover, the disclosed UTE-MT techniques were implemented to investigate the magic angle behavior of UTE-MT modeling, which found that parameters such as macromolecule proton fraction and exchange rates are magic angle insensitive, while T2 and T2* are very sensitive to the magic angle effect. This example result suggests that disclosed UTE-MT imaging and modeling techniques can provide magic angle insensitive biomarkers to evaluate tissue degeneration, e.g., such as loss of macromolecules, thus a reduction in macromolecule proton fraction. These biomarkers can have applications in osteoarthritis, osteoporosis, multiple sclerosis, tendon diseases, etc.

In some implementations, the disclosed UTE-MT imaging and modeling techniques can be implemented in cortical bone, meniscus and tendons in vitro and in vivo. Example 2D UTE-MT and 3D UTE-MT, together with MT modeling, were utilized, in which all techniques showed consistent and robust results. The disclosed 2D and 3D UTE-MT imaging and modeling techniques can reliably measure water and macromolecule protons, as well as their T1s, T2s and exchange rates in vitro and in vivo.

Example 1: 2-Pool MT Modeling

In some implementations, for example, the method 200 includes using a two-pool MT modeling process to map T1s, T2s, exchange rates and fractions of water and macromolecules of short T2 tissues.

Equations [1]-[6], referred to as Henkelman's equations, describe modified Bloch equations incorporated into the mathematical description of the MT phenomenon by the application of non-Lorentzian lineshapes for a semisolid pool:

$$\frac{dM_z^A}{dt} = R_A(M_0^A - M_z^A) - RM_0^B M_z^A + RM_0^A M_z^B + w_1 M_y^A \quad [1]$$

$$\frac{dM_z^B}{dt} = R_B(M_0^B - M_z^B) - RM_0^A M_z^B + RM_0^B M_z^A + w_1 M_y^B \quad [2]$$

$$\frac{dM_x^{A,B}}{dt} = -\frac{M_x^{A,B}}{T_2^{A,B}} - 2\pi \Delta f M_y^{A,B} \quad [3, 4]$$

$$\frac{dM_y^{A,B}}{dt} = -\frac{M_y^{A,B}}{T_2^{A,B}} 2\pi \Delta f M_x^{A,B} - w_1 M_z^{A,B} \quad [5, 6]$$

In Equations [1]-[6], $M_0^{A,B}$ are the fully relaxed values of magnetization of pools A and B, respectively; $M_{x,y,z}^{A,B}$ are the x, y and z components of the magnetization of pools A and B, respectively; $w_1$ is the angular frequency of precession induced by the off-resonance MT pulse and is a measure of the amplitude of the $B_1$ field; $\Delta f$ is the frequency offset of the MT pulse in Hz; $R_{A,B}$ are the longitudinal rate constants; and $T2^{A,B}$ are the transverse relaxation times for pools A and B, respectively.

Due to scan time limitations and specific absorption rate (SAR) concerns, however, the long CW pulse can be replaced in in vivo MT applications by short, shaped (e.g., Gaussian or Fermi) off-resonance pulses that are distributed throughout the imaging sequence. In this case, Henkelman's equations must be modified to allow for the short duration of the saturation pulses relative to $T_1$. For example, the so-called CW power equivalent (CWPE) approximation method can be employed by treating the MT pulse as a rectangular CW signal with the same mean saturating power as the experimentally used shaped pulse in each repetition time. The CWPE amplitude $w_{CWPE}$ is given by Equation [7]:

$$w_{CWPE} = \frac{\theta_{sat}\pi}{p_1 180°}\sqrt{\frac{p_2}{\tau_{sat} TR}}, \quad [7]$$

where: $\theta_{sat}$ is the off-resonance flip-angle; $p_1$ is the ratio of the area of the MT pulse to a rectangular pulse of the same duration and peak amplitude and $p_2$ is the ratio of the square of the MT pulse area to the square of the area of the same rectangular pulse; $\tau_{sat}$ is the duration of the MT pulse; and TR is the time between MT pulses. Also, for example, a parameter f to define the bound proton fraction is given in Equation [8]:

$$f = \frac{M_0^B}{M_0^A + M_0^B} \quad [8]$$

The longitudinal magnetization of the free pool in a steady-state can be expressed as follows in Equation [9]:

$$M_z^A = gM_0^A \frac{R_B\left[\frac{RM_0^A f}{R_A(1-f)}\right] + R_{RFB} + R_B + RM_0^A}{\left[\frac{RM_0^A f}{R_A(1-f)}\right](R_B + R_{RFB}) + \left(1 + \left[\frac{w_1}{2\pi\Delta f}\right]^2 \left[\frac{1}{R_A T_2^A}\right]\right)(R_{RFB} + R_B + RM_0^A)} \quad [9]$$

where: g is a amplitude scaling factor of the acquired data; $R_{RFB}$ is the rate of loss of longitudinal magnetization of pool B due to the direct saturation of the MT pulse; $R_{RFB}$ is related to the absorption lineshape $G(\lambda\pi\Delta f)$ of the spins in the pool B and is given by Equation [10]:

$$R_{RFB} = \pi w_1^2 G(2\pi\Delta f). \quad [10]$$

Since the protons in the semisolid pool do not experience the motional narrowing as the protons in the free pool, they cannot be characterized by the Lorentzian lineshape function that results from the Bloch formalism. Gaussian and super-Lorentzian lineshapes have been reported to be good representations for the semisolid pool. The Gaussian and super-Lorentzian lineshapes are expressed as $G_G(2\pi\Delta f)$ and $G_{sL}(2\pi\Delta f)$ in Equations [11] and [12], respectively:

$$G_G(2\pi\Delta f) = \frac{T_2^B}{\sqrt{2\pi}}\exp\left(-\frac{[2\pi\Delta f T_2^B]^2}{2}\right), \quad [11]$$

$$G_{sL}(2\pi\Delta f) = \int_0^{\pi/2} d\theta \sin\theta \sqrt{\frac{2}{\pi}}\frac{T_2^B}{|3\cos^2\theta - 1|}\exp\left(-2\left[\frac{2\pi\Delta f T_2^B}{|3\cos^2\theta - 1|}\right]^2\right), \quad [12]$$

where: $\theta$ is the angle between the $B_0$ and the axis of molecular orientation.

Since the qMT experiments are largely insensitive to $R_B$ (i.e., the relaxation rate of the bound pool), $R_B$ has been fixed arbitrarily to be 1 l/s. Thus, as can be seen from Eq. [9], there are total five independent variables, which are: $gM_0^A$, $RM_0^A$, $$f/[R_A(1-f)], \frac{1}{R_A T_2^A},$$

and $T_2^B$ (via $R_{RFB}$). Values of these intermediary parameters can be obtained by fitting acquired data to the Eq. [9]. Then, if the apparent longitudinal relaxation rate $$R_{1obs}\left(=\frac{1}{T_1}\right)$$

of the imaging object, which can be estimated by a conventional $T_1$ measured sequence, is known, $R_A$ is determined by:

$$R_A = \frac{R_{1obs}}{1 + \frac{RM_0^A f}{R_A(1-f)}\frac{(R_B - R_{1obs})}{(R_B - R_{1obs}) + RM_0^A}} \quad [13]$$

As such, final MT parameters of the example embodiment of the process 210 are obtained, which are f, $T_2^A$, $T_2^B$, $RM_0^A$, and $1/(R_A T_2^A)$.

Example 2: 2D UTE 2-Pool MT Imaging of Achilles Tendon

In some implementations, for example, the method 200 includes using a two dimensional (2D) UTE two-pool MT imaging sequence to map T1s, T2s, exchange rates and fractions of water and macromolecules of short T2 tissues with different angle orientations between fiber direction and main field $B_0$ for the target tissue, such as a musculoskeletal tissue, e.g., Achilles tendon.

The example 2D UTE-MT imaging protocol included the following parameters, TR=50 ms, TE=10 μs, non-selective hard pulse with a flip angle=5°, FOV=5*5 cm², matrix=256*256; five MT powers (e.g., 300°, 600°, 900°, 1200° and 1500°) and five MT frequency offsets (e.g., 2, 5, 10, 20 and 50 kHz) for the saturation MT pulse (e.g., 8 ms Fermi shaped pulse), with a total of 25 different MT datasets. The same example protocol was applied to each tendon sample fifth with five angle orientations (e.g., 0°, 30°, 55°, 70°, 90°) between fiber direction $\vec{F}$ and $\vec{B_0}$.

Figure 3:
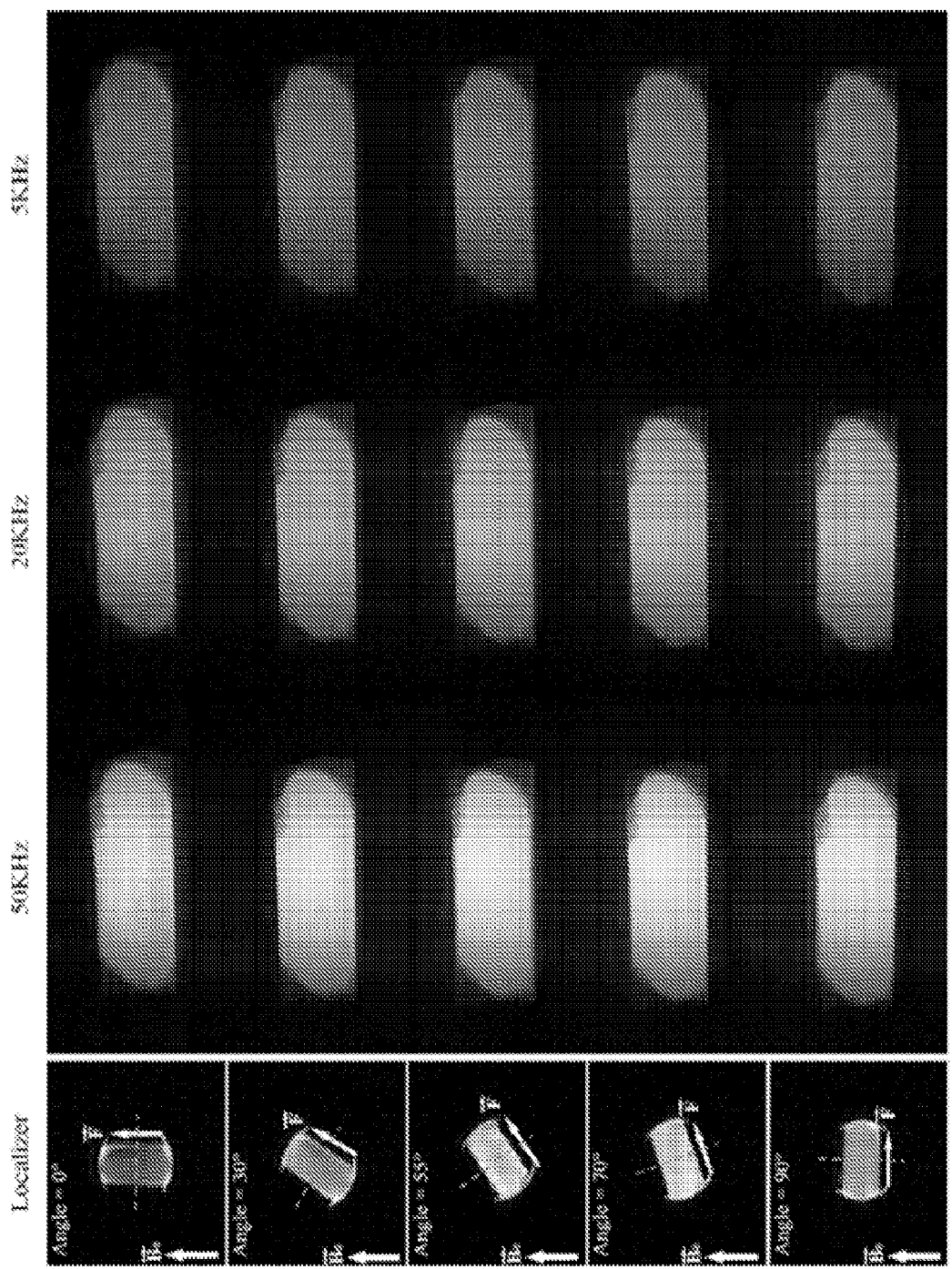
FIG. 3 shows a diagram of MR images obtained using an example embodiment of a 2D UTE-MT method in accordance with the present technology.

FIG. 3 shows a diagram of MR images obtained using an example embodiment of a 2D UTE-MT method in accordance with the present technology. The diagram depicts localizers and MT images of five angle orientations (i.e. 0°, 30°, 55°, 70°, 90°) between fiber direction $\vec{F}$ and $\vec{B_0}$. The first columns are the localizers and the direction of both $\vec{F}$ and $\vec{B_0}$ are represented by white arrows. The dashed lines are the imaging planes. The second to fourth columns are the corresponding MT images with different off-resonance frequencies of 50, 20 and 5 KHz of the saturation pulse with flip angle 1500°, respectively. The five example groups of MT images with different angle orientations are normalized, respectively.

FIGS. 4A-4E show graphs of fitted plots of example MT modeled data and multiple-TE data. The graphs depict fitting results of both MT modeling (first column) and multiple-TE data (second column). The example results of five angle orientations (e.g., 0°, 30°, 55°, 70°, 90°) between fiber direction $\vec{F}$ and $\vec{F}$ are shown in the first to fifth columns, respectively. For MT modeling, experimental data were acquired with five off-resonance frequencies (e.g., 2, 5, 10, 20, 50 KHz) and five different pulse powers (e.g., 300° (circles), 600° (right-pointing triangles), 900° (squares), 1200° (left-pointing triangles), 1500° (pentagram)) for the saturation pulse. The corresponding fitting results are shown by lines. For the fitting of multiple-TE data, the experimental data and fitting results are shown by squares and lines, respectively.

Figure 5:
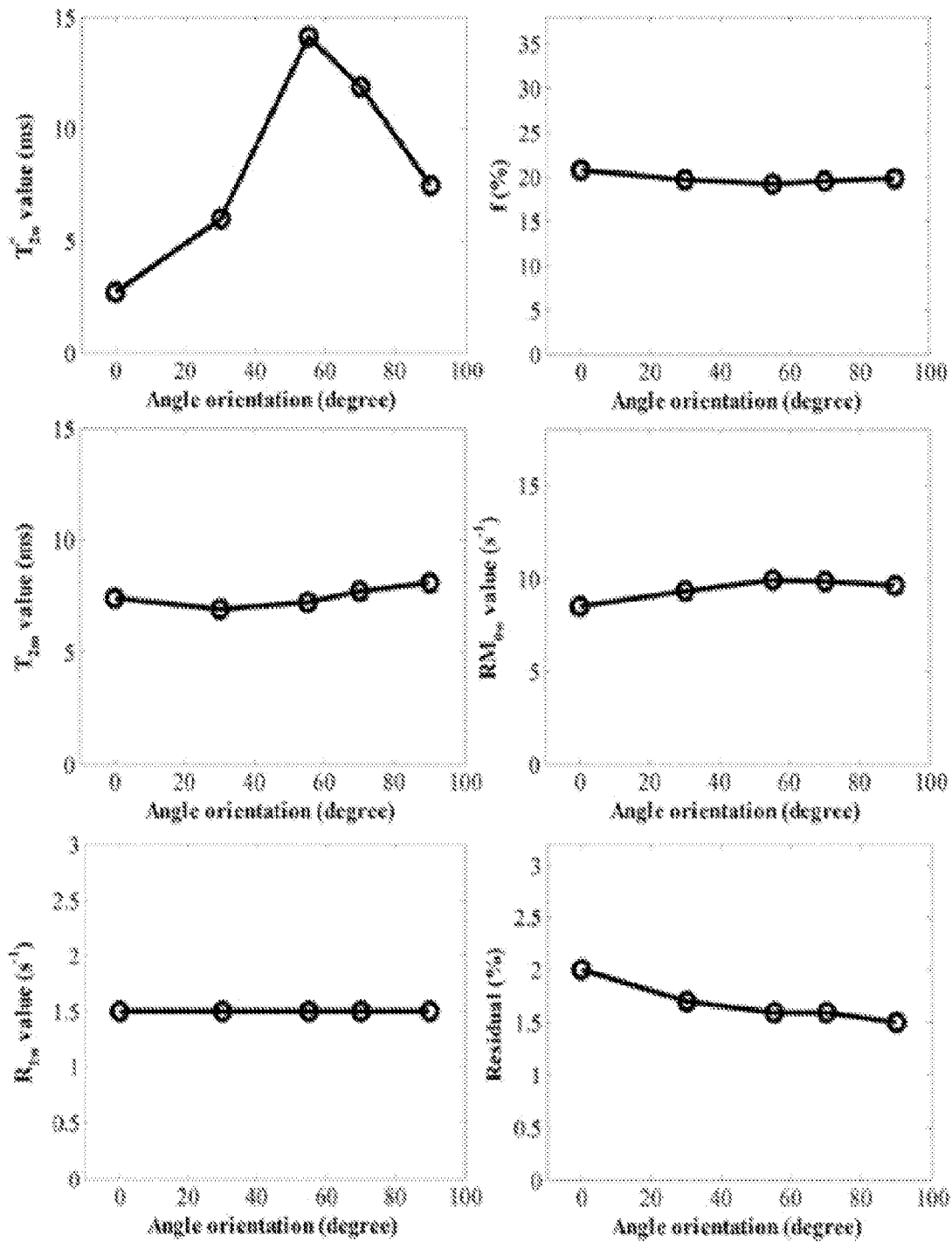
FIG. 5 shows graphs of fitted plots of example MT modeled data with five angular orientations.

FIG. 5 shows graphs of fitted plots of example MT modeled data with five angle orientations. The graphs show: $T_{2w}^*$ values derived by fitting multiple-TE data and macromolecular proton fractions (f) (top row); $T_2$ value of macromolecular proton ($T_2m$) (middle row, left column); exchange rate from macromolecular proton to water proton ($RM_{0w}$) (middle row, right column); longitudinal relaxation rate of water proton ($R_{1w}$) (bottom row, left column); and fitting residuals (%)(bottom row, right column) derived from MT modeling with five angle orientations (i.e. 0°, 30°, 55°, 70°, 90°) between fiber direction $\vec{F}$ and $\vec{B_0}$.

Example 3: 3D Cones 2-Pool MT Imaging of Cortical Bone

In some implementations, for example, the method 200 includes using a three dimensional (3D) cones two-pool MT imaging sequence to map T1s, T2s, exchange rates and fractions of water and macromolecules of short T2 tissues in vivo, such as a musculoskeletal tissue, e.g., cortical bone.

The example 3D Cones UTE-MT imaging protocol included the following parameters: TR=120 ms, TE=32 μs, flip angle=5°, FOV=15*15*10 cm3, matrix=128*128*10, five spokes per-TR; four MT powers (e.g., 600°, 900°, 1200° and 1500°) and five MT frequency offsets (e.g., 2, 5, 10, 20 and 50 kHz) for the saturation MT pulse (e.g., 8 ms Fermi shaped pulse), with a total of 20 different MT datasets.

FIGS. 6A-6C show example MT modeling results of in vivo cortical bone. FIG. 6A shows images of two sets of MT powers (e.g., 600° and 1500°) for MT modeling. Signals within the red ellipse are used for MT modeling. FIGS. 6B and 6C show graphs of fitting results of MT modeling with both Gauss (FIG. 6B) and Super-Lorentzian (FIG. 6C) lineshapes of the macromolecular pool. Experimental data were acquired with five off-resonance frequencies (e.g., 2, 5, 10, 20, 50 KHz) and four different pulse powers (e.g., 600° (circles), 900° (right-pointing triangles), 1200° (squares), 1500° (left-pointing triangles)) for the saturation pulse. The corresponding fitting results are shown by lines.

Table 1 shows example Cones-MT modeling results of in vivo cortical bone.

TABLE 1

| | f (%) | $T_{2m}$ (us) | $RM_{0w}$ (s$^{-1}$) | $R_w$ (s$^{-1}$) | Residual (%) |
|---|---|---|---|---|---|
| Gauss | 36.4 | 13.8 | 20.2 | 6.6 | 2.0 |
| Super-Lorentzian | 46.8 | 5.2 | 19.8 | 7.9 | 1.3 |

Example 4: 3D Cones 2-Pool MT Imaging of Meniscus

In some implementations, for example, the method 200 includes using a three dimensional (3D) cones two-pool MT imaging sequence to map T1s, T2s, exchange rates and fractions of water and macromolecules of short T2 tissues in vivo, such as a musculoskeletal tissue, e.g., meniscus.

The example 3D Cones UTE-MT imaging protocol included the following parameters: TR=100 ms, TE=32 μs, flip angle=7°, FOV=15*15*10 cm$^3$, matrix=128*128*10, Eight spokes per-TR; four MT powers (i.e. 600°, 900°, 1200° and 1500°) and five MT frequency offsets (i.e. 2, 5, 10, 20 and 50 kHz) for the saturation MT pulse (i.e. 8 ms Fermi shaped pulse), with a total of 20 different MT datasets.

FIGS. 7A-7C show example MT modeling results of in vivo meniscus. FIG. 7A shows images of two sets of MT powers (i.e. 600° and 1500°) for MT modeling. Signals within the red triangle were used for MT modeling. FIGS. 7B and 7C shows graphs of fitting results of MT modeling with both Gauss (FIG. 7B) and Super-Lorentzian (FIG. 7C) lineshapes of the macromolecular pool. Experimental data were acquired with five off-resonance frequencies (e.g., 2, 5, 10, 20, 50 KHz) and four different pulse powers (e.g., 600° (circles), 900° (right-pointing triangles), 1200° (squares), 1500° (left-pointing triangles)) for the saturation pulse. The corresponding fitting results are shown by lines.

Table 2 shows example Cones-MT modeling results of in vivo meniscus.

TABLE 2

| | f (%) | $T_{2m}$ (us) | $RM_{0w}$ (s$^{-1}$) | $R_w$ (s$^{-1}$) | Residual (%) |
|---|---|---|---|---|---|
| Gauss | 8.1 | 17.6 | 20.2 | 16.6 | 1.6 |
| Super-Lorentzian | 9.4 | 7.6 | 19.8 | 19.8 | 1.0 |

Example 5: 3D UTE 3-Pool MT Imaging

In some implementations, for example, the method 200 includes using a three dimensional (3D) UTE three-pool MT imaging sequence to map T1s, T2s, exchange rates and fractions of water and macromolecules of short T2 tissues in vivo, such as a musculoskeletal tissue.

The example implementations included three-pool models, which divides the spins within a biological tissue into three pools: (1) a free pool (A) composed of liquid protons; (2) a bound water pool (B) composed of bounded water protons in macromolecules; and (3) a semisolid pool (C) that includes macromolecular protons.

FIG. 8 shows an example three-pool MT model, in which pool A is the free proton pool, pool B is the bound water proton pool, and pool C is macromolecular proton pool.

Each example pool has its own set of intrinsic longitudinal and transverse relaxation times. For example, similar to two-pool model, the magnetization exchanges between the three pools are modeled by the first-order relaxation approximation. The effects of transverse magnetization exchanges have not been included. The inclusion of transverse magnetization exchanges leads to only small corrections to the steady-state signal intensity.

The modified Bloch equations without transverse magnetization exchanges are given by Equations [14]-[22]:

$$\frac{dM_z^A}{dt} = R_A(M_0^A - M_z^A) - k_{AB}M_z^A + k_{BA}M_z^B - k_{AC}M_z^A + k_{CA}M_z^C + w_1 M_y^A \quad [14]$$

$$\frac{dM_z^B}{dt} = R_B(M_0^B - M_z^B) - k_{BA}M_z^B + k_{AB}M_z^A - k_{BC}M_z^B + k_{CB}M_z^C + w_1 M_y^B \quad [15]$$

$$\frac{dM_z^C}{dt} = R_C(M_0^C - M_z^C) - k_{CB}M_z^C + k_{BC}M_z^B - k_{CA}M_z^C + k_{AC}M_z^A + w_1 M_y^C \quad [16]$$

$$\frac{dM_x^{A,B,C}}{dt} = -\frac{M_x^{A,B,C}}{T_2^{A,B,C}} - 2\pi\Delta f M_y^{A,B,C} \quad [17-19]$$

$$\frac{dM_y^{A,B,C}}{dt} = -\frac{M_y^{A,B,C}}{T_2^{A,B,C}} + 2\pi\Delta f M_x^{A,B,C} - w_1 M_z^{A,B,C} \quad [20-22]$$

where: $M_0^{A,B,C}$ are the fully relaxed values of magnetization of pools A, B and C, respectively; $M_{x,y,z}^{A,B,C}$ are the x, y and z components of the magnetization of pools A, B and C, respectively; $w_1$ is the angular frequency of precession induced by the off-resonance MT pulse and is a measure of the amplitude of the $B_1$ field; $\Delta f$ is the frequency offset of the MT pulse in Hz; $R_{A,B,C}$ are the longitudinal rate constants and $T_2^{A,B,C}$ are the transverse relaxation times for pools A, B and C, respectively; $k_{AB}$, $k_{BA}$, $k_{BC}$, $k_{CB}$, $k_{AC}$ and $k_{CA}$ are the cross-relaxation constants for magnetization transfer from A to B, B to A, B to C, C to B, A to C and C to A.

Their relativities because of the first-order relaxation approximation are expressed in Equation [23] as:

$$k_{AB}M_0^A = k_{BA}M_0^B, k_{BC}M_0^B = k_{CB}M_0^C, k_{AC}M_0^A = k_{CA}M_0^C. \quad [23]$$

Similar to the two-pool model, the Bloch equations from Eq. [14] to [23] for a three-pool model are solved within a steady-state, and the longitudinal magnetizations of pools A and B are expressed below:

$$M_z^A = M_0^A \frac{\alpha_{1A} + \alpha_{2A}}{R^A R^B R^C fg - f k_{AC}^2 R^B - f^2 R^A k_{BC}^2 - k_{AB}^2 g R^C - 2 f k_{AB} k_{BC} k_{AC}} \quad [24]$$

$$M_z^B = M_0^A \frac{\alpha_{1B} + \alpha_{2B}}{R^A R^B R^C fg - f k_{AC}^2 R^B - f^2 R^A k_{BC}^2 - k_{AB}^2 g R^C - 2 f k_{AB} k_{BC} k_{AC}} \quad \text{where:} \quad [25]$$

$$f = M_z^B / M_z^A, \quad g = M_z^C / M_z^A \text{ and where:} \quad [26]$$

$$|\alpha_{1A} = -f^2 R_A k_{BC}^2 + fg R_A R^B R^C + fg k_{AC} R_C R^B \quad [27]$$

$$\alpha_{2A} = f^2 R_B k_{AC} k_{BC} + fg R^C k_{AB} R_B + fg k_{AB} k_{BC} R_C \quad [28]$$

$$\alpha_{1B} = -f^2 R_B k_{AC}^2 + fg R_A k_{AB} R^C + fg k_{AB} k_{AB} R_C \quad [29]$$

$$\alpha_{2B} = f^2 g R_B R^A R^C + f^2 k_{BC} k_{AC} R_A + f^2 g R^A k_{BC} R_C \text{ and} \quad [30]$$

where:

$$R^A = k_{AB} + k_{AC} + R_A + R_{RFA} \quad [31]$$

$$R^B = k_{AB}/f + k_{BC} + R_B + R_{RFB} \quad [32]$$

$$R^C = k_{AC}/g + k_{BC} f/g + R_C + R_{RFC} \quad [33]$$

$R_{RFi}$ (1=A, B and C) are related to the absorption lineshape $G(2\pi\Delta f)$ of the spins in the pools A, B and C, which are given by:

$$R_{RFi} = \pi w_1^2 G(2\pi\Delta f) \quad [34]$$

Both of the absorption lineshapes of the pools A and B are Lorentzian lineshape due to the motion narrowing character of their spins. The Lorentzian lineshape $G_L(2\pi\Delta f)$ is expressed as follows:

$$G_L(2\pi\Delta f) = \frac{T_2^{A,B}}{\pi\left[1 + (2\pi\Delta f T_2^{A,B})^2\right]} \quad [35]$$

Similar to the two-pool model, Gaussian and super-Lorentzian lineshapes can be used for pool C. For example, the CWPE approximation for the magnetization saturation by MT pulse can be employed to this three-pool modeling.

If ultrashort echo time (UTE) imaging is used, the signals of both pools A and B can be obtained, which is shown as follows:

$$S = M_z^A e^{-TE/T_{2A}} + M_z^B e^{-TE/T_{2B}} \quad [36]$$

where TE is the echo time.

As can be seen from Eq. [14] to [36], there are total 12 physical parameters (e.g., $M_0^A$, $T_2^{A,B,C}$, $k_{AC}$, $k_{BC}$, $k_{AC}$, $R_{A,B,C}$, f, g) in the three-pool model. These parameters can be determined by fitting the acquired MT data to Eq. [36].

Example 6: 2D UTE 3-Pool MT Imaging of Bovine Cortical Bone

In some implementations, for example, the method 200 includes using a two dimensional (2D) UTE-MT imaging sequence by 3-pool modeling to map T1s, T2s, exchange rates and fractions of water and macromolecules of short T2 tissues, such as a musculoskeletal tissue, e.g., bovine cortical bone.

FIGS. 9A-9C show example 3-pool MT modeling results of bovine cortical bone. FIG. 9A shows images of MR imaging results of bovine cortical bone, in which the first two rows show the images of two sets of MT powers (e.g., 600° and 1500°) for MT modeling. Signals within the red circle are used for MT modeling. MT data (e.g., left image in the bottom row) and multi-TE data (e.g., right image in the bottom row) are combined for 3-pool modeling. FIGS. 7B and 7C show example MT data that were acquired with five off-resonance frequencies (e.g., 2, 5, 10, 20, 50 KHz) and five different pulse powers (e.g., 300° (circles), 600° (right-pointing triangles), 900° (squares), 1200° (left-pointing triangles), 1500° (pentagram)) for the saturation pulse. Multi-TE data were acquired with sixteen TEs (e.g., 0.01, 0.1, 0.2, 0.4, 0.6, 0.8, 1.0, 1.5, 2, 2.5, 3, 4, 5, 6, 7, 8 ms). The corresponding fitting results of MT modeling are shown by lines.

Table 3 shows example parameters derived from the three-pool modeling of UTE-MT data of a bovine cortical bone sample. $T_2$ of free water ($T_{2A}$), $T_2$ of bound water ($T_{2B}$), $T_2$ of macromolecule protons ($T_{2C}$), fraction of free water ($f_A$), fraction of bound water ($f_B$), fraction of macromolecule protons ($f_C$), exchange rate from free water to bound water ($R_{AB}$), exchange rate from bound water to macromolecule ($R_{BC}$), recovery rate of longitudinal magnetization of free water ($R_A$), bound water ($R_B$) and macromolecule protons ($R_C$) derived from the three-pool modeling of UTE-MT data of a bovine cortical bone sample.

TABLE 3

| $T_{2A}$ (ms) | $T_{2B}$ (ms) | $T_{2C}$ (us) | $f_A$ (%) | $f_B$ (%) | $f_C$ (%) |
|---|---|---|---|---|---|
| 1.63 | 0.27 | 14.5 | 13.2 | 44.2 | 42.6 |
| $R_{AB}$ (s$^{-1}$) | $R_{BC}$ (s$^{-1}$) | $R_A$ (s$^{-1}$) | $R_B$ (s$^{-1}$) | $R_C$ (s$^{-1}$) | Residual (%) |
| 44.4 | 7.2 | 15.2 | 0.33 | 2.0 | 0.15 |

Example 7: 2D UTE 2-Pool MT Imaging for Investigating Magic Angle Effect

In some implementations, for example, the method 200 includes using a two dimensional (2D) UTE two-pool MT imaging sequence to map T1s, T2s, exchange rates and fractions of water and macromolecules of short T2 tissues with different angle orientations, including the magic angle, between fiber direction and main field $B_0$ for the target tissue, such as a musculoskeletal tissue, e.g., Achilles tendon.

An example study using the example UTE-MT technique with two-pool modeling was performed and demonstrated promise as a clinically compatible technique that is resistant to the magic angle effect. The example method provides information on the macromolecular proton pool that cannot be directly obtained by other methods, including regular UTE techniques. For example, MRI biomarkers such as $T_2$, $T_2^*$ and $T_{1rho}$ have been widely used, but are confounded by the magic angle effect. The example study investigated the use of 2D UTE-MT sequence for potential magic angle independent MR biomarkers. In the example study, MT was investigated in cadaveric Achilles tendon samples using the UTE-MT sequence at five MT powers and five frequency offsets, e.g., ranging from 2-50 kHz. The protocol was applied at five sample orientations ranging, e.g., from 0-90° relative to the $B_0$ field. The example results were analyzed with a two-pool quantitative MT model. Multiple TE data was also acquired and mono-exponential $T_2^*$ was calculated for each orientation. The example results included macromolecular proton fractions and exchange rates derived from the example UTE-MT modeling procedures, which did not appreciably change between the various orientations whereas the $T_2^*$ relaxation time demonstrated up to a 6-fold increase from 0° to 55°.

In the example study, human Achilles tendon samples dissected from four fresh cadaveric ankle specimens that were harvested. Data were acquired with a 2D UTE-MT sequence on a clinical 3T Signa TwinSpeed scanner (e.g., GE Healthcare Technologies) with a maximum gradient strength of 40 mT/m and a maximum slew rate of 150 mT/m/ms. A home-built birdcage coil (e.g., ~2 cm in diameter) was used for signal excitation and reception. The example UTE-MT MR data acquisition sequence employed a short non-selective hard pulse (e.g., duration=32 µs) excitation followed by 2D radial ramp sampling with a minimal nominal TE of 8 µs. The example MT preparation included a Fermi shaped RF pulse (e.g., duration=8 ms) followed by a gradient crusher. The example UTE-MT MR imaging protocol included the following parameters: TR=50 ms, TE=8 µs, Flip angle=5°, FOV=5×5 cm$^2$, matrix=256×256; five MT powers (e.g., 300°, 600°, 900°, 1200° and 1500°) and five MT frequency offsets (e.g., 2, 5, 10, 20 and 50 kHz), with a total of 25 different MT datasets. The same protocol was applied to each tendon sample five times, with the sample oriented at, for example, 0°, 30°, 55°, 70° and 90° relative to the $B_0$ field. Multiple TE data was also acquired with these five angle orientations for mono-exponential fitting to determine $T_2^*$ value of the water component. The example protocol for multiple-TE data acquisition was identical with the example UTE-MT protocol except that a non-MT pulse was used and TEs were 0.008, 2, 4, 8, 12, 16, 20 ms.

For example, a multiple-TR UTE protocol was employed for $T_1$ measurement, whose sequence parameters were the same with the MT modeling protocol except that a non-MT pulse was used, image flip angle=25°, and TRs were 25, 50, 100, 200, 400, 600 ms. $T_1$ is resistant to the magic angle effect, and therefore the multiple-TR sequence was only performed with angle orientation=55° for each sample.

In the example study, image and data analysis included the following. An example two-pool UTE-MT modeling was performed on the acquired MR data. In the example two-pool MT model, the MT pulse are treated as a rectangular continuous wave signal with the same mean saturating power as the experimentally used shaped pulse in each repetition time to approximate a continuous wave power equivalent (CWPE), in which the ($w_{CWPE}$) angular frequency of precession induced by the off-resonance MT pulse ($w_{CWPE}$) is a measure of the amplitude of the $B_1$ field, represented by the Equation [A1]. The $w_{CWPE}$ value was used in calculations performed in subsequent data processing after experimental MR data has been acquired from the target tissue (e.g., tendon).

For example, the acquired data with a variety of saturation powers and off-resonance frequencies $\Delta f$ were fitted based at least in part on Equation [A2] and/or Equation [A3]. Since the protons in the macromolecular pool do not experience the motional narrowing that the protons in the free pool experience, they cannot be characterized by the Lorentzian lineshape function that results from the Bloch formalism. Super-Lorentzian lineshapes can provide good representations for the macromolecular pool in Achilles tendon. The super-Lorentzian expression used was in accordance with Equation [A4].

The final parameters of f, $T_{2m}$ and $RM_{0w}$ are obtained in accordance with Equation [A5]. For example, since the quantitative MT experiments are largely insensitive to $R_{1m}$ (e.g., the relaxation rate of the macromolecular pool), $R_{1m}$ has been fixed arbitrarily to be 1 s$^{-1}$. Thus, for example, there are total five independent variables, which are $gM_{0w}$, $RM_{0w}$, $f/[R_{1w}(1-f)]$, $1/(R_1T_{2w})$, $T_{2m}$. These parameters can be obtained by fitting the acquired data to the Equation [A2].

In the study, for example, the analysis algorithm was written in Matlab (e.g., MathWorks Inc., Natick, Mass., USA) and was executed offline on the DICOM images obtained by the protocols described above. The program allowed placement of ROIs on the first UTE image of the series, which was then copied onto each of the subsequent images. The mean intensity within each of the ROIs was used for both two-pool modeling and multiple-TE mono-exponential fitting.

Some of the example results of the example study were previously shown in FIGS. 3, 4A-4E and 5A-5C. Table 4 shows the mean and standard variation (SD) values off, $T_{2m}$, $RM_{0w}$, residual and $T_2^*$ across five angle orientations (e.g., 0°, 30°, 55°, 70°, 90°) between fiber direction $\vec{F}$ and $\vec{B_0}$ of four cadaveric human Achilles tendon samples. Small SD values of all the four samples show magic angle effect independent results from MT modeling. In contrast, large SD values of $T_2^*$ demonstrated a large magic angle effect.

TABLE 4

| Sample | f (%) | $T_{2m}$ (us) | $RM_{0w}$ (s$^{-1}$) | Residual (%) | $T_2$*(ms) |
|---|---|---|---|---|---|
| 1 | 19.8 ± 0.6 | 7.5 ± 0.5 | 9.4 ± 0.6 | 1.7 ± 0.2 | 8.4 ± 4.6 |
| 2 | 19.9 ± 0.6 | 7.6 ± 0.6 | 16.7 ± 1.1 | 2.1 ± 0.2 | 5.9 ± 4.1 |
| 3 | 19.6 ± 0.6 | 7.2 ± 0.5 | 10.6 ± 0.8 | 1.6 ± 0.2 | 5.6 ± 3.7 |
| 4 | 20.0 ± 0.3 | 7.6 ± 0.7 | 9.2 ± 0.2 | 1.7 ± 0.1 | 6.1 ± 4.6 |

In the example study, the example results have shown that the example UTE-MT imaging and modeling techniques can be performed on data acquired on a clinical 3T scanner and provides parameters that are resistant to the magic angle effect, such as macromolecular proton fractions and exchange rates between water and macromolecular protons. This is a substantial improvement compared to conventional techniques, which have the exquisitely magic-angle sensitive mono-exponential UTE-$T_2$* relaxation times. The example results demonstrated up to a 10-fold increase from 0° to 55° in our tendon specimens, a finding similar to previously published results.

In recent years, a number of potential clinically compatible, magic angle resistant MR biomarkers have been proposed. This includes $T_{1rho}$ using an adiabatic spin-lock RF pulse, UTE-$T_2$* bi-component fractions, and diffusion weighted imaging. The example results confirm that UTE-MT also yields magic-angle independent measurements. Compared with the conventional techniques, an example unique advantage of the example UTE-MT sequence is that information on the macromolecular protons can be obtained. This proton pool typically demonstrates extremely rapid $T_2$ relaxation and cannot be directly obtained by other clinically compatible methods, including UTE or zero echo time (ZTE) techniques. UTE-MT modeling measurements with UTE-$T_2$* bi-component fractions would be of interest to provide information on all proton pools, including macromolecular protons, bound water, and free water.

The example UTE-MT modeling techniques utilized in the example study was shown to provide information on tissue properties, such as the macromolecular proton fraction and exchange rates between water and macromolecular protons, and is much less sensitive to the magic angle effect compared with mono-exponential $T_2$* values of the water protons. UTE-MT modeling can be applied to both short and long $T_2$ tissues such as the Achilles tendon, ligaments, menisci, bone, calcified cartilage and superficial layers of cartilage, and may be potentially be useful for disease identification, monitoring disease progression, and assessing response to therapy.

Example 8: Comparison of UTE 2-Pool and 3-Pool MT Modeling

In some implementations, a two-pool MT modeling and a three-pool MT modeling are compared in an example study of example embodiments of the disclosed UTE-MT Imaging and Modeling technology.

An example comparative study using the example UTE-MT technique with two-pool modeling and three-pool modeling was performed for bovine cortical bone samples using a clinical 3T scanner.

Magnetization transfer (MT) is a MR technique that generates contrast based on the exchange of magnetization between several groups of spins in different molecular environments. Both two-pool and three-pool models can characterize the different groups of spins. The three-pool MT model divides the spins within a biological tissue into three groups, e.g., (1) a free pool A, composed of mobile protons; (2) a bound water pool B, composed of water protons bound to macromolecules and (3) a semisolid pool C, which includes macromolecular protons. In the example study, the two-pool MT model is highly simplified and only considers a water pool A and a macromolecule pool B. Theoretically, a three-pool model should be more accurate than the two-pool model for describing biological tissues.

Conventional MT modeling can only be applied to long T2 tissues since short T2 tissues such as cortical bone show litter or no signal with clinical sequences. Ultrashort echo time magnetization transfer (UTE-MT) imaging is likely to help with this difficulty.

Both two-pool and three-pool MT models have been described in the literature. Pool B is generally considered MR "invisible". This is true with common clinical sequence but not correct with UTE sequences. With UTE-MT sequence, the signal equation is a combination of the steady-state longitudinal magnetization of pools A and B:

$$S = M_z^A e^{-TE/T2A} + M_z^B e^{-TE/T2B}$$ [B1]

where $T_2^A$ and $T_2^B$ are the $T_2$ value of pools A and B; and TE is the echo time.

Data with different TEs can be useful in separating pools A and B. In addition, the continuous wave power equivalent (CWPE) method for pulsed wave MT saturation used for the two-pool MT model can also be used for the three-pool modeling. Here, Gauss spectral absorption lineshape for the pool C was employed.

The example study, MR data were acquired from a sectioned bovine cortical bone specimen (e.g., thickness=2 cm) using a 2D non-slice selective UTE-MT sequence on a clinical 3T scanner (e.g., GE Healthcare Technologies). A home-built birdcage coil (e.g., ~2.5 cm in diameter) was used for signal excitation and reception. The UTE sequence employed a short rectangular pulse (e.g., duration=32 µs) excitation followed by 2D radial ramp sampling with a minimal nominal TE of 8 µs. The MT preparation utilized a Fermi shaped RF pulse (e.g., duration=8 ms) and a gradient crusher. The UTE-MT MR imaging protocol included the following parameters and/or settings: TR=100 ms, TE=8 µs, FOV=4 cm, matrix=128×128, five saturation powers (e.g., 300°, 600°, 900°, 1200° and 1500°) and five frequency offsets (e.g., 2, 5, 10, 20 and 50 kHz) with a total of 25 different MT dataset. In addition, UTE data with sixteen TEs (e.g., 0.01, 0.1, 0.2, 0.4, 0.6, 0.8, 1.0, 1.5, 2, 2.5, 3, 4, 5, 6, 7, 8 ms) were acquired for bi-component T2* analysis.

For data processing in this example study, two-pool MT modeling was employed first to provide useful information for further three-pool modeling, such as the T2 value and fraction of semisolid pool C. These two parameters are fixed in the three-pool modeling in order to reduce the sensitivity to fitting errors. The MT data and multiple TE data were combined together to fit Equation [B1]. The example results include the following.

Figure 10A:
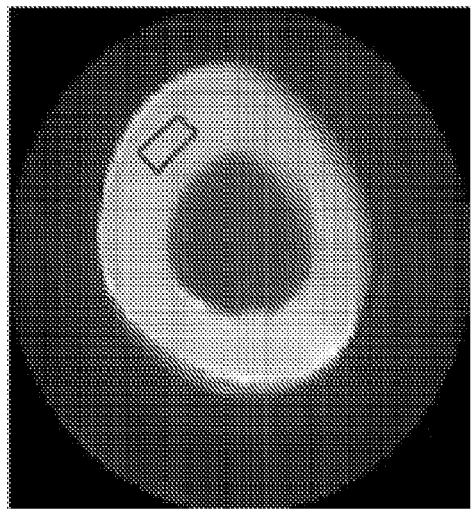
FIG. 10A shows an example representative UTE image of a section of bovine cortical bone used for an example two-pool and three-pool modeling analysis.
Figure 10B:
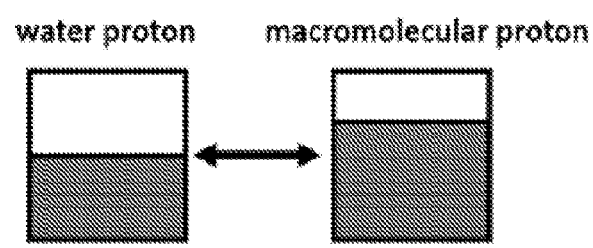
FIGS. 10B and 10C show a diagram of the example two-pool MT model and a graph depicting a fitting of UTE-MT data acquired, respectively.
Figure 10C:
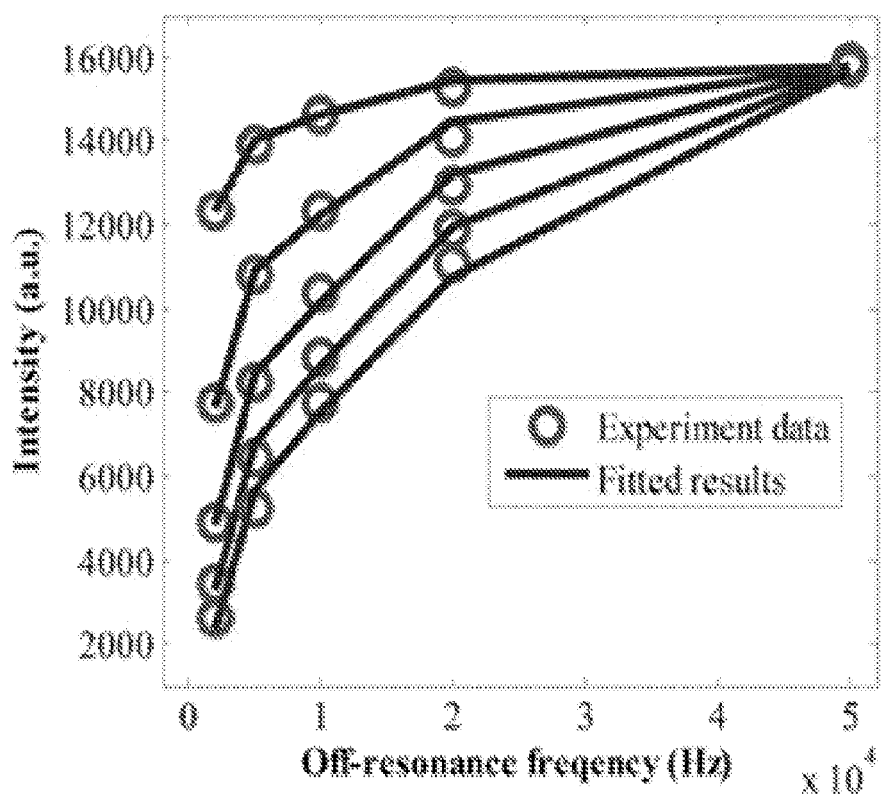

FIG. 10A shows an example representative UTE image of a section of bovine cortical bone and the region of interest (ROI) (shown in the box) used for subsequent two-pool and three-pool modeling analysis. FIG. 10B shows a diagram of the example two-pool MT model. FIG. 10C shows a graph depicting a fitting of UTE-MT data acquired with five saturation powers (e.g., θ=300°, 600°, 900°, 1200° and 1500°) and five frequency offset (e.g., Δf=2, 5, 10, 20 and 50 kHz). The theoretical two-pool model provides excellent fitting of the experimental data.

Table 5 shows example fitting results. $T_2$ of water ($T_{2w}$), $T_2$ of macromolecule protons ($T_{2m}$), fraction of macromolecule protons ($f_m$), exchange rate from macromolecule to water ($RM_{0w}$) and recover rate of longitudinal magnetization of water pool ($R_w$) derived from the two-pool modeling of UTE-MT data of a bovine cortical bone sample.

TABLE 5

| $T_{2w}$ (ms) | $T_{2m}$ (us) | $f_m$ (%) | $RM_{0w}$ (s$^{-1}$) | $R_w$ (s$^{-1}$) | Residual (%) |
|---|---|---|---|---|---|
| 0.35 | 14.5 | 42.6 | 11.5 | 4.9 | 0.17 |

Figure 11A:
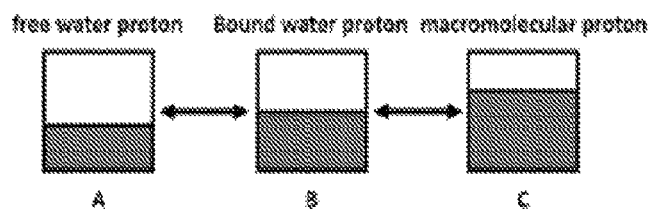
FIG. 11A shows a diagram of the example chain coupled three-pool model used for subsequent two-pool and three-pool modeling analysis.
Figure 11B:
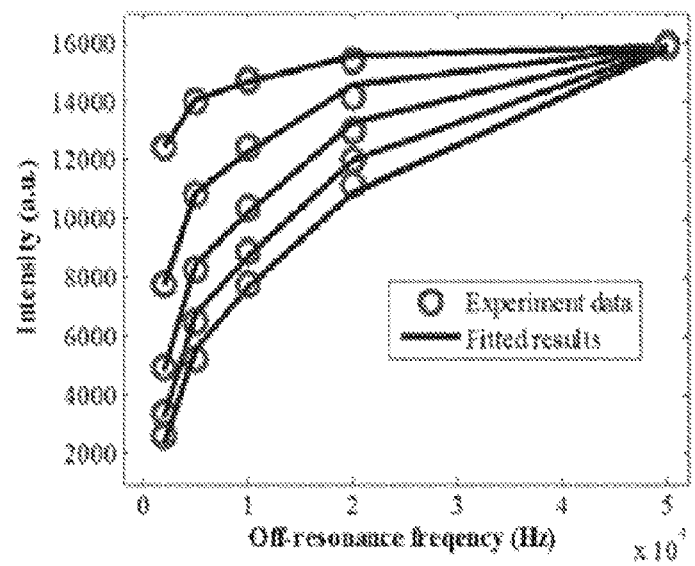
FIGS. 11B and 11C show graphs depicting a fitting of UTE-MT data acquired.
Figure 11C:
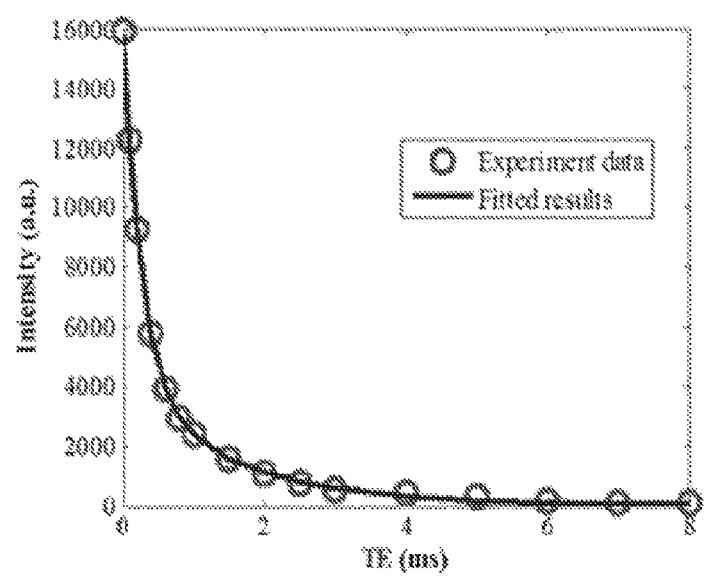

FIG. 11A shows a diagram of the example chain coupled three-pool model employed in this study. It is based on the assumption that the exchange rate between A and C is significantly less than the exchange rates between both A and B and B and C. The three-pool fitting curves are shown in the FIGS. 11B and 11C, and the corresponding fitting parameters are shown in Table 6. For example, the example fitting plot of FIGS. 11B and 11C include UTE-MT MR data acquired with five saturation powers (e.g., θ=300°, 600°, 900°, 1200° and 1500°) and five frequency offsets (e.g., Δf=2, 5, 10, 20 and 50 kHz) (FIG. 11B), and fitting of UTE data acquired with a series of TEs (FIG. 11C). For example, free water, bound water and macromolecule protons have T2s of 1.63 ms, 0.27 ms and 14.5 μs, with fractions of 13.2%, 44.2% and 42.6%. These values are largely consistent with the literature.

Table 6 shows example fitting results. $T_2$ of free water ($T_{2A}$), $T_2$ of bound water ($T_{2B}$), $T_2$ of macromolecule protons ($T_{2C}$), fraction of free water ($f_A$), fraction of bound water ($f_B$), fraction of macromolecule protons ($f_C$), exchange rate from free water to bound water ($R_{AB}$), exchange rate from bound water to macromolecule ($R_{BC}$), recovery rate of longitudinal magnetization of free water ($R_A$), bound water ($R_B$) and macromolecule protons ($R_C$) derived from the three-pool modeling of UTE-MT data of a bovine cortical bone sample.

TABLE 6

| $T_{2A}$ (ms) | $T_{2B}$ (ms) | $T_{2C}$ (us) | $f_A$ (%) | $f_B$ (%) | $f_C$ (%) |
|---|---|---|---|---|---|
| 1.63 | 0.27 | 14.5 | 13.2 | 44.2 | 42.6 |
| $R_{AB}$ (s$^{-1}$) | $R_{BC}$ (s$^{-1}$) | $R_A$ (s$^{-1}$) | $R_B$ (s$^{-1}$) | $R_C$ (s$^{-1}$) | Residual (%) |
| 44.4 | 7.2 | 15.2 | 0.33 | 2.0 | 0.15 |

The macromolecule pool has a short T2 of 14.5 μs and a fraction of 42.6%, consistent with results from NMR spectroscopy studies of cortical bone samples.

As shown in the example study, both two-pool and three-pool MT modeling can be accomplished in bovine cortical bone samples with the disclosed UTE-MT MR imaging and modeling technology. The two-pool modeling and UTE bi-component analysis provide prior information useful for the three-pool modeling and reduces fitting errors minimized. The two-pool and three-pool UTE-MT modeling approach can be applied to many other short T2 tissues such as menisci, ligaments, tendons, deep radial and calcified cartilage. It can provide a comprehensive evaluation of joint tissues degeneration in osteoarthritis (OA) and bone properties in osteoporosis (OP).

Example 9: UTE-MT Imaging and Modeling for Investigating Magic Angle-Independent Biomarkers of Tissue Properties Magnetic resonance imaging biomarkers such as T2 and $T1_{rho}$ have been used in the evaluation of osteoarthritis (OA). The principal confounding factor for T2 and $T1_{rho}$ measures is the magic angle effect, which may result in a several fold increase in T2 and $T1_{rho}$ values when the fibers are oriented near 55° (the magic angle) relative to the $B_0$ field. This often far exceeds the changes produced by OA, and may make definitive interpretation of elevated T1rho and T2 values difficult or impossible. Magic angle independent MR biomarkers are highly desirable for more accurate assessment of OA.

In some implementations, an example embodiment of a two-dimensional ultrashort echo time magnetization transfer (UTE-MT) MR imaging and modeling method for assessing magic angle independence of the tissue properties was performed.

A classic two-pool (e.g., water and macromolecular proton pools) MT model has been used for continuous wave MT. With such conventional models, a long continuous MT RF pulse is needed to drive the two-pool system to the steady state. This may not be possible with typical MRI hardware systems and may also cause a very large SAR. MT imaging on existing clinical scanners have been used, for example, in which a continuous wave power equivalent (CWPE) method for pulsed wave saturation can be applied.

In the example study, a variety of parameters such as the T2 values of both water (T2w) and macromolecular protons (T2m), macromolecular proton fractions (f), proton exchange rates from macromolecular to water ($RM_{0w}$) pools and recovery rate of longitudinal magnetization of water pool ($R_w$) can be obtained based on fitting in an MT model in accordance with the present technology.

The example study included dissecting human Achilles tendon samples from cadaveric human ankle specimens (n=3), which were harvested for this example study. Data were acquired with a 2D UTE-MT sequence on a clinical 3T scanner (e.g., GE Healthcare Technologies). A custom-built birdcage coil (e.g., ~2 cm in diameter) was used for signal excitation and reception. The UTE-MT sequence employed a short half pulse excitation followed by 2D radial ramp sampling with a minimal nominal TE of 8 μs. The MT preparation included a Fermi shaped RF pulse (duration=8 ms) followed by a gradient crusher. The UTE-MT imaging protocol included: TR=100 ms, TE=8 μs, FOV=4*4 cm$^2$, matrix=256*256, slice thickness=3 mm, five MT powers (e.g., 300°, 600°, 900°, 1200° and 1500°) and five MT frequency offsets (e.g., 2, 5, 10, 20 and 50 kHz), respectively, with a total of 25 different MT datasets. The same protocol was applied to each tendon sample twice, one with the fiber parallel to the $B_0$ field and the other with fibers oriented 55° relative to the $B_0$ field. Two-pool UTE-MT modeling was performed on both datasets to investigate the angular dependence of each of the MT modeling parameters.

Figure 12A:
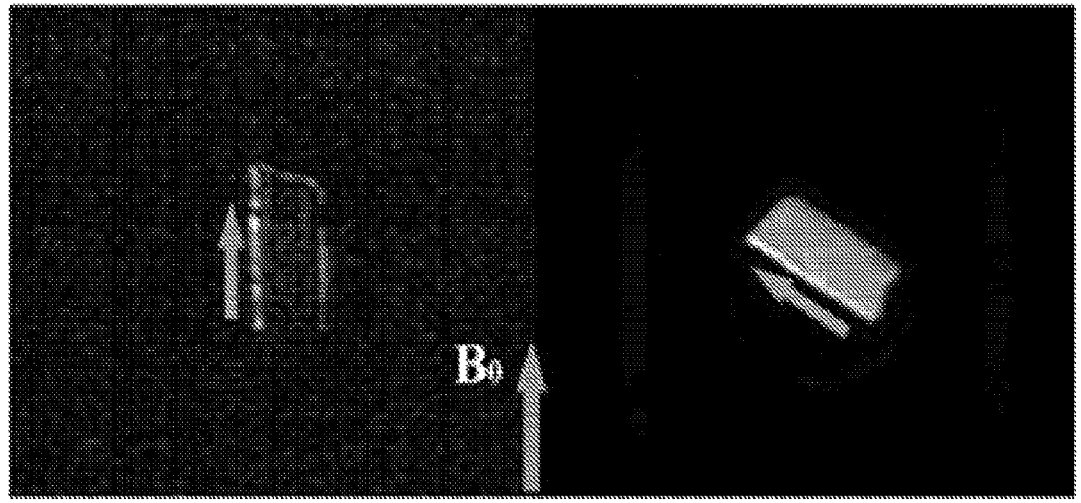
FIGS. 12A and 12B show images of example clinical gradient echo imaging and UTE-MT imaging of a cadaveric human Achilles tendon sample oriented parallel and 55° to the applied $B_0$ field.
Figure 12B:
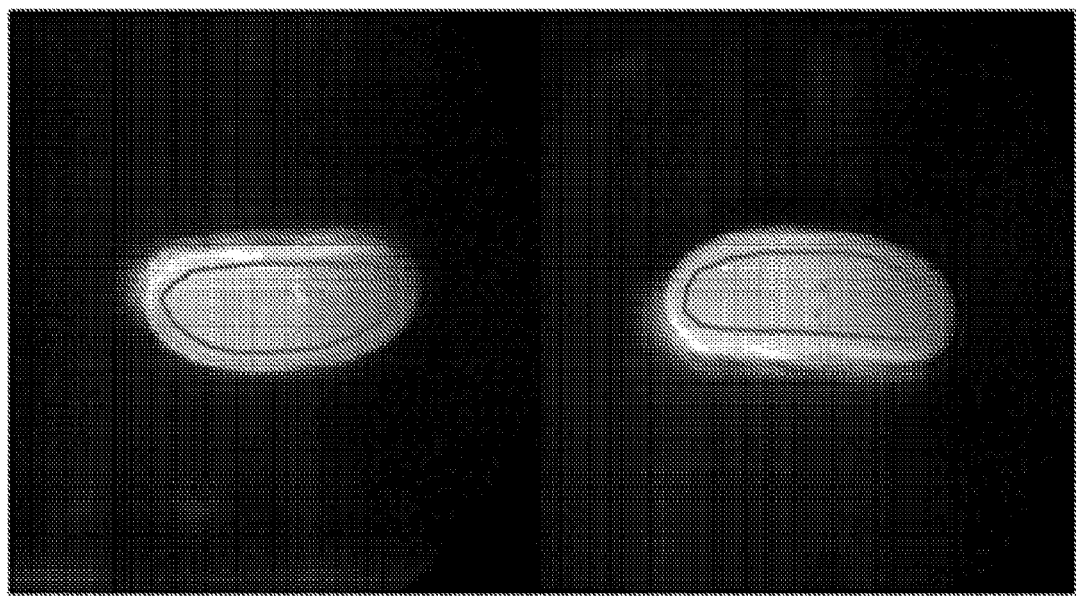

FIGS. 12A and 12B show clinical gradient echo imaging (FIG. 12A) and UTE-MT imaging (FIG. 12B) of a cadaveric human Achilles tendon sample which is oriented parallel (left) and 55° (right) to the $B_0$ field. FIG. 12A shows the sagittal views of the tendon images acquired with a clinical GRE sequence (TE/TR=4/16.7 ms) with the two angular orientations. The two arrows besides the specimens indicated the orientation of the fibers in the specimens. The SNR of the data with angle=55° was significantly higher than that of the data with angle=0° due to the magic angle effect. FIG. 12B shows the corresponding axial UTE-MT images of the same tendon, with the imaging plane perpendicular to the fiber orientation.

Figure 13:
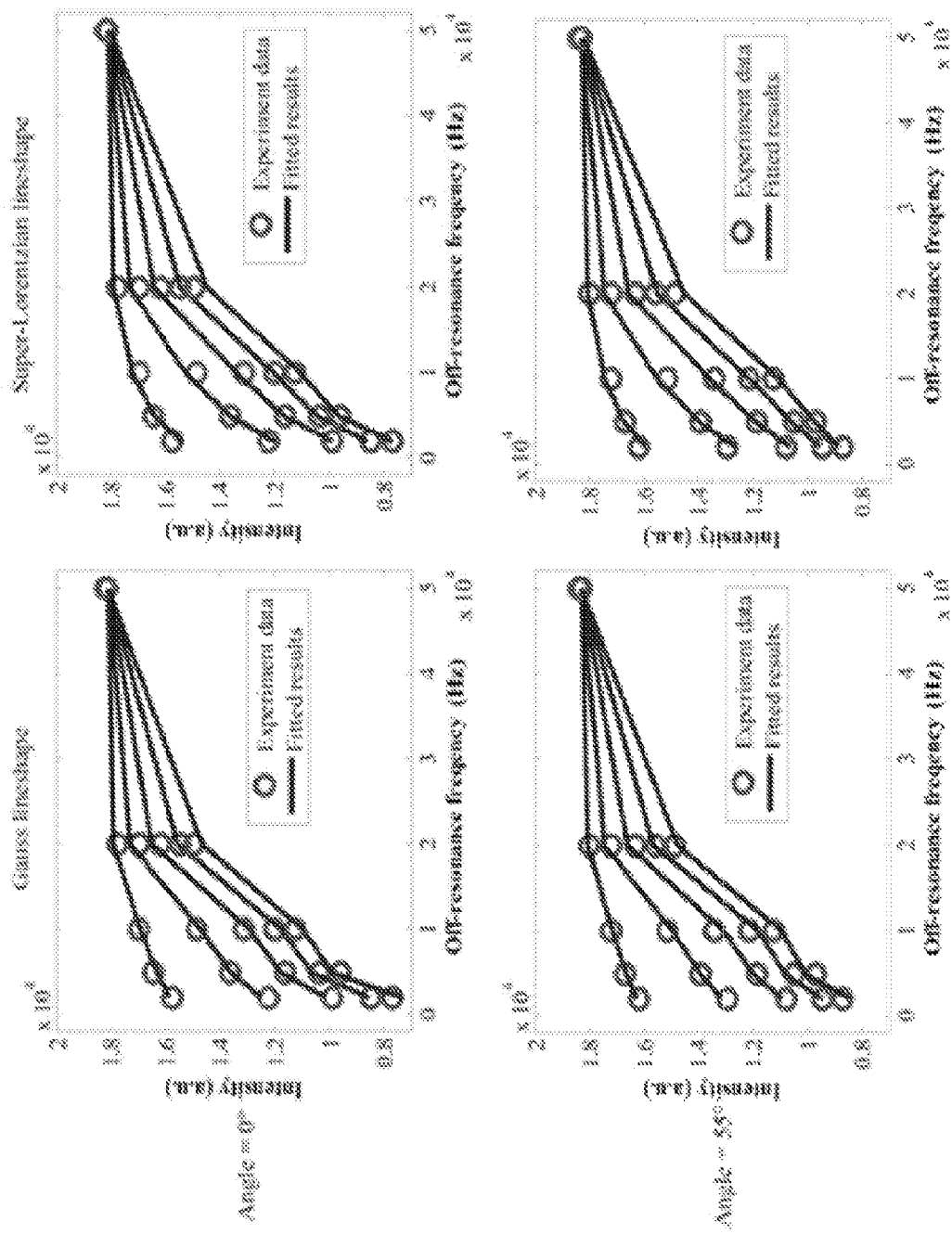
FIG. 13 shows the data plots from the example two-pool UTE-MT modeling technique including Gauss and Super-Lorentzian spectral absorption lineshapes for macromolecular protons investigated in the samples shown in FIGS. 12A-12B.

FIG. 13 shows the example results of two-pool UTE-MT modeling technique implementation. Both Gauss and Super-Lorentzian spectral absorption lineshapes for the macromolecular proton were investigated. For example, the plots on the left column depict the example UTE-MT modeling using Gauss; and the plots of the right column depict the example Super-Lorentzian spectral absorption lineshapes, in which the Achilles tendon sample was oriented parallel (shown in the upper row) and 55° (shown in the lower row) to the $B_0$ field. The fitting residuals of Super-Lorentzian lineshape were slightly less than Gauss lineshape, with both results consistent with the literature.

The physical parameters obtained from the two-pool MT modeling are shown in the Table 1. While T2 increased by 95% with the Gaussian lineshape and 500% with the Super-Lorentzian lineshape due to the magic angle effect, changes were less than 9% for macromolecular proton fraction and 20% for $RM_{0w}$, and no changes are observed in $R_w$. This suggests that UTE-MT modeling parameters such as f, $RM_{0w}$ and $R_w$ can be used as magic angle insensitive biomarkers of tissue properties.

Table 7 shows example two-pool MT modeling of the cadaveric Achilles tendon data.

TABLE 7

| $T_{2w}$ (ms) | | | $T_{2m}$ (us) | f (%) | $RM_{0w}$ ($s^{-1}$) | $R_w$ ($s^{-1}$) | Residual (%) |
|---|---|---|---|---|---|---|---|
| Gauss | angle = 0° | 8.1 | 17.6 | 17.2 | 5.9 | 1.3 | 0.14 |
|  | angle = 55° | 15.8 | 17.1 | 15.6 | 7.4 | 1.3 | 0.13 |
| Super-Loren-tzian | angle = 0° | 13.6 | 7.6 | 18.6 | 6.6 | 1.3 | 0.13 |
|  | angle = 55° | 83.5 | 7.2 | 16.6 | 8.6 | 1.3 | 0.12 |

The example study demonstrates that embodiments of the UTE-MT MR imaging and/or modeling methods and systems in accordance with the present technology can provide a variety information about tissue properties, e.g., the macromolecular proton fraction and exchange rate between water and macromolecular protons, which are much less sensitive to the magic angle effect compared with T2 values of the water protons. These magic angle effect immune parameters may be useful markers for disease identification. The disclosed UTE-MT modeling techniques can be applied to both short and long T2 tissues, including but not limited to, the Achilles tendon, ligaments, menisci, bone, calcified cartilage and superficial layers of cartilage, which may provide a comprehensive magic angle independent "whole-organ" approach for evaluation of joint degeneration. For example, this may have a major impact on early detection in OA, monitoring disease progression, and assessing response to therapy.

Example 10: 2D UTE-MT Imaging of Cortical Bone

In some implementations, an example embodiment of a two-dimensional ultrashort echo time magnetization transfer (UTE-MT) MR imaging and modeling method was employed for assessing ex vivo bovine cortical bone and in vivo human tibial cortical bone.

In the example study, data were acquired from 5 sectioned bovine cortical bone specimens and 5 healthy volunteer tibial cortical bones using a 2D UTE-MT sequence on a clinical 3T scanner. The 2D UTE-MT sequence employed four or five MT powers with five frequency offsets. Example results were analyzed with a two-pool quantitative MT model, providing measurements of macromolecular fraction (f), macromolecular proton transverse relaxation times ($T_{2m}$), proton exchange rates from water/macromolecular to the macromolecular/water pool ($RM_{0m}$/$RM_{0w}$) and spin-lattice relaxation rate of water pool ($R_{1w}$).

Example results included the following. Mean bovine cortical bone values for f, $T_{2m}$, $R_{1w}$, $RM_{0m}$, and $RM_{0w}$ were 59.9±7.3%, 14.6±0.3 µs, 9.9±2.4 $s^{-1}$, 17.9±3.6 $s^{-1}$ and 11.8±2.0 $s^{-1}$, respectively. Mean in vivo human cortical bone values for f, $T_{2m}$, $R_{1w}$, $RM_{0m}$ and $RM_{0w}$ were 54.5±4.9%, 15.4±0.6 µs, 8.9±1.1 $s^{-1}$, 11.5±3.5 $s^{-1}$ and 9.5±1.9 $s^{-1}$, respectively.

Osteoporotic fractures, such as of the hip and vertebra, have a very high morbidity and mortality. With a lifetime risk of approximately 40-50% for women and 13-22% for men, osteoporotic fractures are generally defined as occurring at sites of low bone mineral density (BMD). Although BMD is considered the standard measure for the diagnosis of osteoporosis and assessment of fracture risk, several studies have demonstrated that BMD cannot be used as the sole predictor of bone strength. In particular, changes in BMD have been shown to account for <50% of variation in whole bone strength, with the majority of fragility fractures occurring in patients with a T-score>−2.5. Identification of more sensitive determinants of bone strength using magnetic resonance imaging (MRI) has consequently been an active area of interest.

Due to the short $T_2$ components of bone matrix, conventional clinical MRI systems are generally limited to the imaging of the marrow space. While high resolution MRI has been shown to detect age and disease-induced changes in trabecular morphology, the use of ultrashort echo time (UTE) pulse sequences has allowed for the quantitative evaluation of cortical bone. Water content and $T_2$* measurements have been shown to correlate with cortical bone porosity and failure properties. Despite that, protons with extremely fast transverse relaxation, such as tightly bound water and collagen protons, remain undetectable even when UTE is employed. Magnetization transfer (MT) imaging has therefore been investigated as a potential method to indirectly assess these "invisible" proton pools.

The MT technique generates unique contrast and quantitative information in MRI by exploiting coupling processes between macromolecular and mobile protons. MT imaging uses an off-resonance radiofrequency pulse to preferentially saturate macromolecular protons. Since macromolecular protons can influence the spin state of mobile protons, this off-resonance saturation can be subsequently transferred to mobile protons and thereby be measured by MRI. The extent of magnetization transfer between these two pools of protons depends on their rate of exchange.

The example implementations using quantitative modeling of MT phenomena in combination with UTE described for this study demonstrate improvement of the sensitivity and reproducibility of MT metrics in cortical bone. The example results include optimized acquisition protocols and insight into MT behavior in ex vivo bovine and in vivo healthy human tibial cortical bone. For example, the example implementations demonstrate that UTE-MT imaging and modeling methods and systems in accordance with the present technology can enable measurements that might potentiate new surrogate markers for cortical bone strength.

The example study included the following. Two-pool MT modeling was performed to determine macromolecular fraction (f), water proton transverse relaxation time ($T_{2w}$), macromolecular proton transverse relaxation time ($T_{2m}$), proton exchange from water to macromolecular pool ($RM_{0m}$), and proton exchange from the macromolecular to water pools ($RM_{0w}$). For example, MT pulse was treated as a rectangular continuous wave (CW) signal with the same mean saturating power as the experimentally used shaped pulse, or the so-called continuous wave power equivalent (CWPE) approximation. The angular frequency of precession $w_{CWPE}$ induced by the off-resonance MT pulse was used to measure the amplitude of the $B_1$ field. The UTE-MT signal was modeled by Equation [C1]:

$$S = gM_{0w} \frac{R_{1m}\left[\frac{RM_{0w}f}{R_{1w}(1-f)}\right] + R_{RFm} + R_{1m} + RM_{0w}}{\left[\frac{RM_{0w}f}{R_{1w}(1-f)}\right](R_{1m} + R_{RFm}) + \left(1 + \left[\frac{w_{CWPE}}{2\pi\Delta f}\right]^2 \left[\frac{1}{R_{1w}T_{2w}}\right]\right)(R_{RFm} + R_{1m} + RM_{0w})} \quad [C1]$$

where $M_{0m}$ and $M_{0w}$ are the fully relaxed magnetizations of macromolecular and water pools, respectively. f is defined as $$\frac{M_{0m}}{M_{0m} + M_{0w}}.$$

$R_{1m}$ and $R_{1w}$ are the corresponding longitudinal rate constants. g is an amplitude scaling factor. R is the first-order magnetization exchange rate constant between the two pools. $R_{RFm}$ is the loss rate of longitudinal magnetization of the macromolecular pool due to the RF saturation of the MT pulse. A Gaussian lineshape was employed for the macromolecular proton pool in cortical bone due to its extremely short $T_2$ value.

The 2D UTE-MT sequence employed an MT preparation pulse followed by a basic 2D UTE data acquisition. The basic 2D UTE sequence used a hard pulse or a short half pulse excitation followed by 2D radial ramp sampling. Fast transmit/receive switching allows for a minimal nominal TE of around 10 μs. The MT preparation pulse is a Fermi pulse with a duration of 8 ms, a spectral bandwidth of 0.8 kHz, a maximal $B_1$ of 24 μT and a maximal saturation flip angle of 1740°. For example, the Fermi pulse was employed because it provided an improved spectral profile compared with a rectangular pulse and higher efficiency compared with conventional Gaussian or sinc pulses, facilitating MT imaging of cortical bone, which has an extremely short apparent transverse relaxation time or $T_2^*$. In the example study, 2D UTE-MT data were acquired with a series of MT pulse frequency offsets (Δf) and powers ($\omega_1$) for two-pool MT modeling.

Five mature bovine femoral and tibial midshafts from freshly slaughtered animals were obtained from a local slaughterhouse and cleaned of external muscle and soft tissue. A bovine cross-section with approximate thickness of 4 cm was cut from each specimen using a low-speed diamond saw (e.g., Isomet 1000, Buehler) with constant water irrigation, and stored in phosphate buffered saline (PBS) solution for 24 hours prior to use. A wrist coil (e.g., BC-10, Medspira) was used for both signal excitation and reception. The 2D non-selective UTE-MT imaging protocol included: TR=100 ms, TE=10 μs, FOV=8×8 cm², hard excitation pulse (e.g., 32 μs) with a flip angle=10°, acquisition matrix=128×128, five MT powers (e.g., 300°, 600°, 900°, 1200° and 1500°) and five MT frequency offsets (e.g., 2, 5, 10, 20 and 50 kHz), with a total of 25 different MT datasets. The total scan time was about 17.5 min. $T_1$ values were measured with the same UTE sequence except without MT preparation using a hard excitation pulse (e.g., 80 μs) with a flip angle=25° and multiple TRs (e.g., 24, 50, 100, 200, 400, 600, 800 ms). Then $T_1$ was calculated by fitting the following Equation [C2]:

$$S = S_0 e^{-\frac{TE}{T_2^*}} \frac{1 - e^{-\frac{TR}{T_1}}}{1 - \cos(\theta)e^{-\frac{TR}{T_1}}} \quad [C2]$$

where $S_0$ is the signal intensity in the equilibrium state and TE is a constant. Therefore, the first two elements in the above equation can be combined into a constant when fitting. Total scan time was about 15.2 min.

The example studying included investigating reproducibility for the example two-pool UTE-MT modeling of cortical bone with three measurements. The MRI system was reset before each measurement and the same slice location was used for all the measurements. Mean and standard deviation values of the three independent measurements were calculated.

The 2D UTE-MT sequence was also applied to the tibial midshaft of five healthy volunteers (e.g., all males, 28-43 years old, mean/standard deviation=32.6±6.4 y) for two-pool modeling. Written informed consent approved by an Institutional Review Board (IRB) obtained prior to their participation in this study. An 8-channel knee coil was used for signal excitation and reception. The protocol was similar to that for the bovine specimens, except for the use of a soft half pulse excitation with variable rate selective excitation (VERSE) (e.g., pulse duration=472 μs, pulse bandwidth=2.7 kHz), FOV=10×10 cm², slice thickness of 7 mm, acquisition matrix=192×192, and four MT powers (e.g., 600°, 900°, 1200° and 1500°) for a total scan time of 14 min. $T_1$ value was measured with a similar 2D selective UTE sequence (e.g., flip angle=25°) and TRs=10, 40, 70, 100, and 150 ms for a scan time of 2.6 min.

In the example study, an analysis algorithm was written in MATLAB 2012a (MathWorks Inc., Natick) and was executed offline on the DICOM images obtained by the 2D UTE-MT protocols described above. Two-pool UTE-MT modeling was performed on the bovine femoral midshaft and human tibial midshaft cortical bones and was performed pixel-wise (e.g., quantitative mapping) and by using the mean values of regions of interest (ROIs) placed in each image separately. Mean and standard deviation of macromolecular proton fractions, relaxation times, exchange rates and water longitudinal relaxation rates were calculated and summarized. Example results included the following.

Figure 14A:
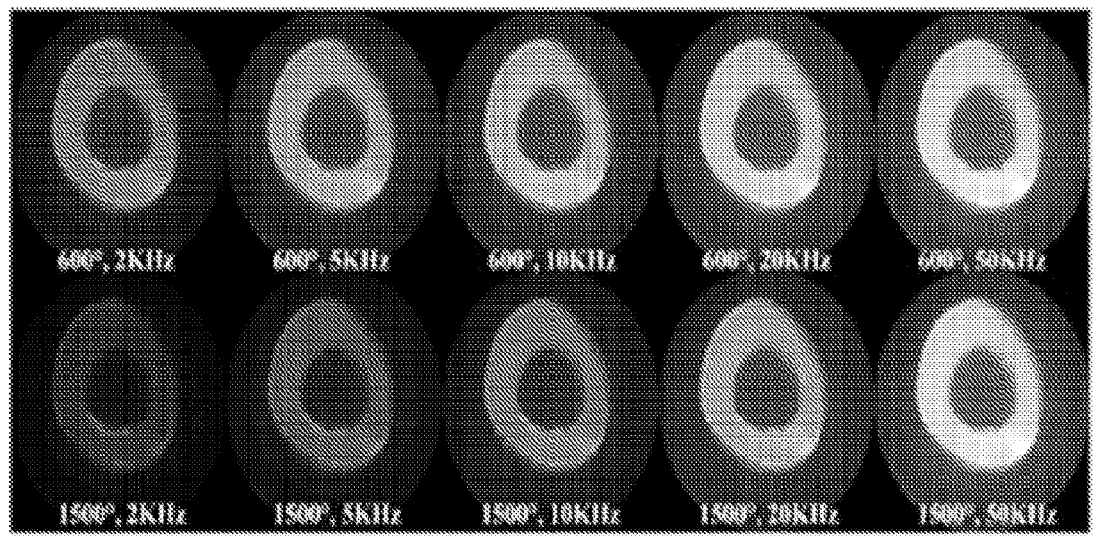
FIGS. 14A and 14B show example 2D UTE-MT images and fitting curve from an ex vivo bovine cortical bone sample with different MT flip angles and off-resonance frequencies.

FIG. 14A shows 2D UTE-MT images from an ex vivo bovine cortical bone sample with different MT flip angles and off-resonance frequencies. Increased cortical bone signal intensity was observed at low MT flip angles and high off-resonance frequencies. The excellent fitting curves demonstrate the validity of using the 2D UTE-MT sequence to model MT effect in cortical bone which has extremely short T2 and shows as signal void when imaged with conventional clinical sequences.

Figure 14B:
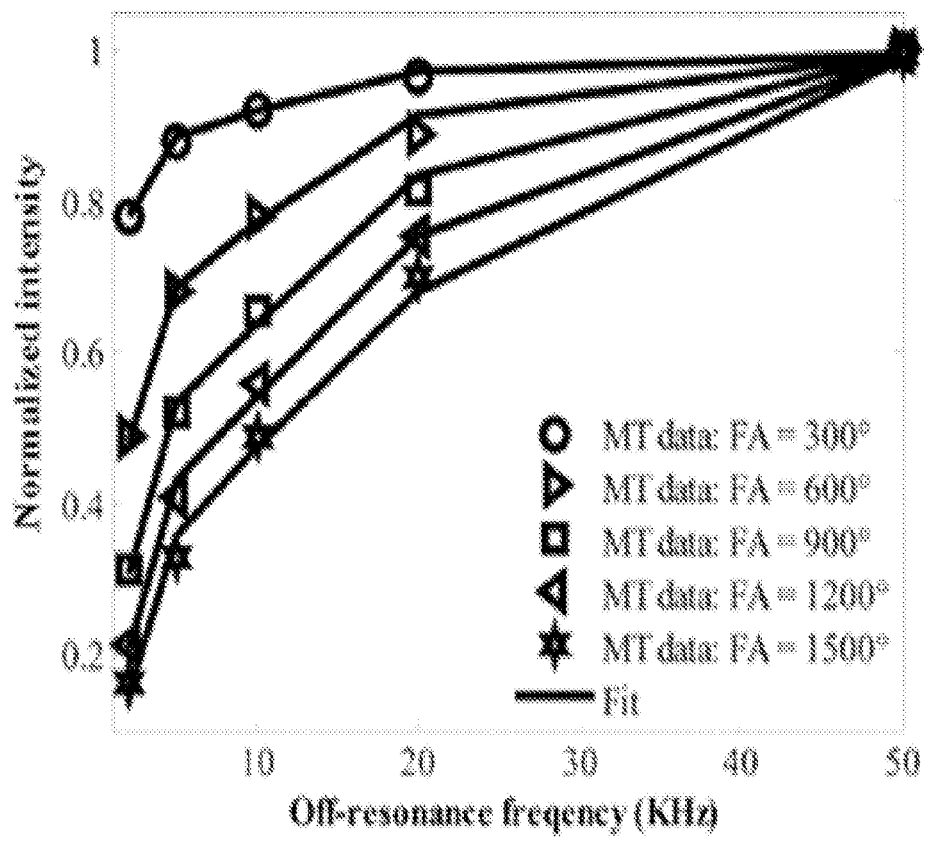

Representative MT images shown in FIG. 14A are from an ex vivo bovine cortical bone specimen obtained with MT flip angles of 600° and 900° at increasing off-resonance frequencies of 2, 5, 10, 20, and 50 kHz. Fitting curves for cortical bone signal intensity versus off-resonance frequency for multiple MT flip angles are shown in FIG. 14B. Increased cortical bone signal intensity is observed at low MT flip angles and high off-resonance frequencies. A circle in top left MT image (e.g., 600°, 2 kHz) of FIG. 14A shows region of interest used for signal intensity measurement.

Figure 15:
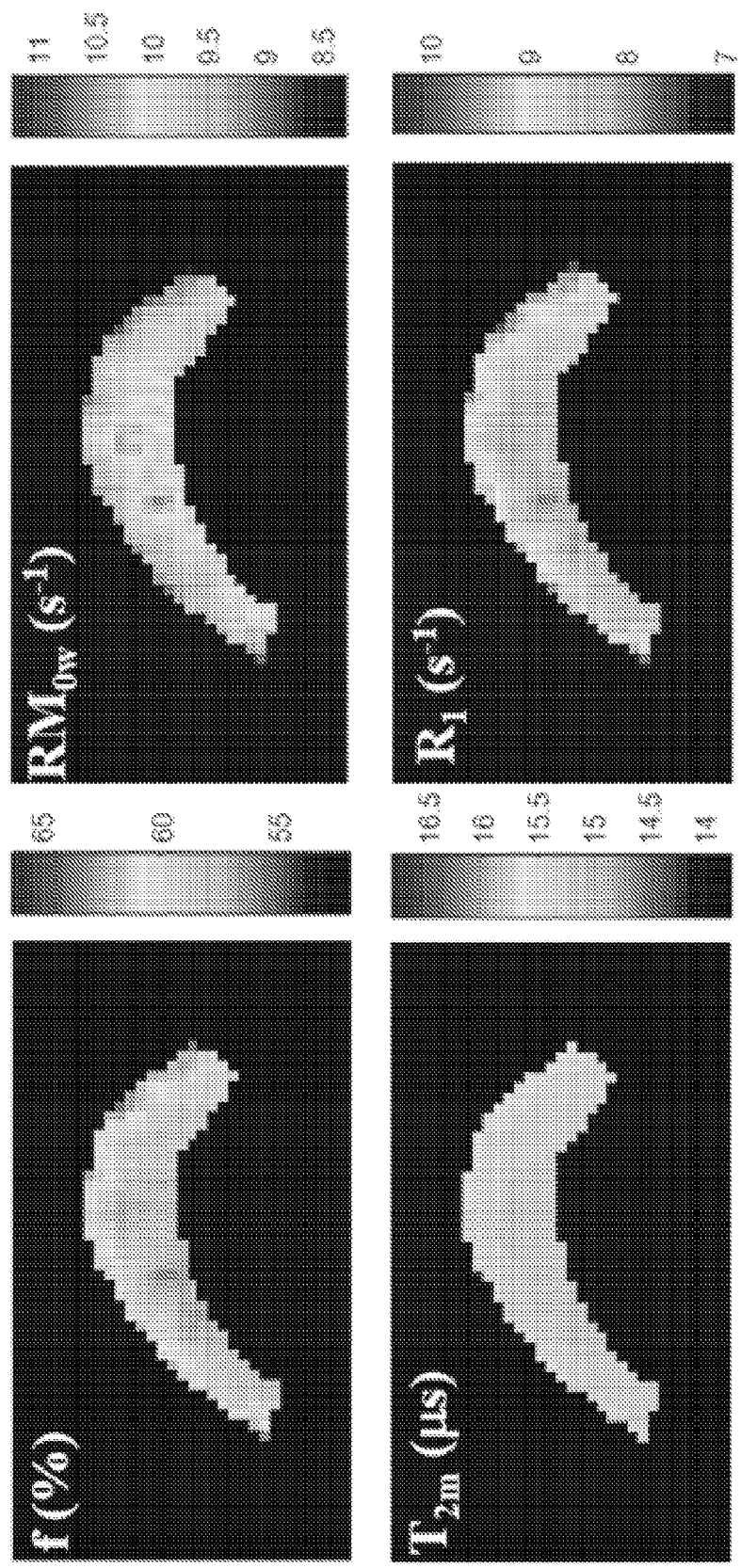
FIG. 15 shows color maps of select MT modeling parameters from another bovine cortical bone specimen.

FIG. 15 shows color maps of select MT modeling parameters from another bovine cortical bone specimen. The parameter distributions of MT modeling can be seen in the analyzed region. The color mapping of MT modeling parameters from an ex vivo bovine cortical bone specimen include macromolecular fraction (f) (top left), proton exchange rate from the macromolecular to water pools ($RM_{0w}$) (top right), $T_2$ relaxation time of the macromolecular pool ($T_{2m}$) (bottom left), and spin-lattice relaxation rate of the water pool ($R_{1w}$) (bottom right). Color maps demonstrate good homogeneity of MT modeling values within cortical bone. Color bar indicates the gradation of MT modeling measures.

Mean and stand deviation values of three independent measurements for f, $T_{2m}$, $R_{1w}$, $RM_{0m}$, and $RM_{0w}$ were 56.1±1.0%, 14.2±0.02 $s^{-1}$, 16.9±0.8 $s^{-1}$, 13.2±0.1 $s^{-1}$ and 8.9±0.4 $s^{-1}$, respectively, demonstrating excellent reproducibility of the 2D UTE-MT modeling technique.

FIG. 16A shows example UTE-MT images from in vivo human cortical bone. Representative MT images shown in FIG. 16A are from in vivo human tibial cortical bone obtained with MT flip angles of 600° and 1500° at increasing off-resonance frequencies of 2, 5, 10, 20, and 50 kHz. The MT flips angles of 600° and 1500° show increased cortical bone signal intensity with lower MT power and higher off-resonance frequencies. Again, excellent curve fitting was achieved for all 2D UTE-MT data acquired with different MT flip angles and off-resonance frequencies, suggesting the feasibility for fast MT modeling of cortical bone in vivo.

FIG. 16B shows fitting curves for cortical bone signal intensity versus off-resonance frequency for multiple MT flip angles. Similar to bovine cortical bone, increased signal intensity is evident at low MT flip angles and high off-resonance frequencies. The dashed box in far-left image of FIG. 16A shows the field of view selection for MT analysis. The circle in top left MT image (e.g., 600°, 2 kHz) of FIG. 16A shows region of interest used for signal intensity measurement.

Quantitative MT modeling measurements of ex vivo and in vivo cortical bone are presented in Tables 8 and 9, respectively. Mean bovine cortical bone values for f, $T_{2m}$, $R_{1w}$, $RM_{0m}$, $RM_{0w}$, and residual of fitting were 59.9±7.3%, 14.6±0.3 μs, 9.9±2.4 $s^{-1}$, 17.9±3.6 $s^{-1}$, 11.8±2.0 $s^{-1}$, and 1.8±0.1%, respectively. Mean human cortical bone values for f, $T_{2m}$, $R_{1w}$, $RM_{0m}$, $RM_{0w}$, and residual of fitting were 54.5±4.9%, 15.4±0.6 μs, 8.9±1.1 $s^{-1}$, 11.5±3.5 $s^{-1}$, 9.5±1.9 $s^{-1}$, and 2.7±0.3%, respectively.

Table 8 shows quantitative MT modeling measurements* for ex vivo bovine cortical bone (N=5). In this table, *f=macromolecular fraction; $T_{2m}=T_2$ relaxation time of macromolecular pool; $R_{1w}$=spin-lattice relaxation rate of water pool; $RM_{0m}$=proton exchange rate from water to macromolecular pool; $RM_{0w}$=proton exchange rate from macromolecular to water pool.

TABLE 8

| | f (%) | $T_{2m}$ (μs) | $R_{1w}$ ($s^{-1}$) | $RM_{0m}$ ($s^{-1}$) | $RM_{0w}$ ($s^{-1}$) | Residual of Fitting (%) |
|---|---|---|---|---|---|---|
| 1 | 57.4 | 14.5 | 8.9 | 15.5 | 11.5 | 1.7 |
| 2 | 59.6 | 14.7 | 9.5 | 16.2 | 11 | 1.7 |
| 3 | 71.4 | 14.8 | 13.9 | 24.3 | 9.7 | 1.9 |
| 4 | 59.6 | 14.7 | 9.4 | 17.2 | 11.7 | 1.8 |
| 5 | 51.5 | 14.1 | 7.6 | 16.1 | 15.2 | 1.9 |

Table 9 shows quantitative MT modeling measurements* for in vivo human tibial cortical bone (N=5). In this table, *f=macromolecular fraction, $T_{2m}=T_2$ relaxation time of macromolecular pool; $R_{1w}$=spin-lattice relaxation rate of water pool; $RM_{0m}$=proton exchange rate from water to macromolecular pool; $RM_{0w}$=proton exchange rate from macromolecular to water pool.

TABLE 9

| | f (%) | $T_{2m}$ (μs) | $R_{1w}$ ($s^{-1}$) | $RM_{0m}$ ($s^{-1}$) | $RM_{0w}$ ($s^{-1}$) | Residual of Fitting (%) |
|---|---|---|---|---|---|---|
| 1 | 61.3 | 15.5 | 10.6 | 13.6 | 8.6 | 2.9 |
| 2 | 54.2 | 16.0 | 9.4 | 8.6 | 7.3 | 2.3 |
| 3 | 51.1 | 15.6 | 8.1 | 10.1 | 9.7 | 2.8 |
| 4 | 48.8 | 15.5 | 7.8 | 8.8 | 9.3 | 2.5 |
| 5 | 56.9 | 14.4 | 8.7 | 16.6 | 12.5 | 2.9 |

In this example study, it was demonstrated that a quantitative model of MT can be performed in ex vivo bovine and in vivo human cortical bone with suitable estimates of model parameters. It was found that the two-pool model to appropriately describe the acquired signal as a function of off-resonance RF power and frequency with good fit.

Several pools of proton signal in cortical bone have been identified, which differ considerably in their transverse relaxation times. For example, six biophysical origins of NMR signal in cortical bone include collagen methylene, collagen amides/hydroxides, mineral hydroxides/water, collagen-bound water, pore space water, and lipid methylene. Since most conventional MRI techniques of cortical bone are dominated by signal from collagen-bound water and to a lesser extent pore water, most prior studies have focused on these proton pools. Cortical porosity, such as from increased bone turnover or age-related bone loss, is a major determinant of bone mechanical strength, and thus identifying potential surrogate measures of cortical porosity is of considerable interest.

In this study, quantitative UTE-MT parameters obtained were f, $T_{2m}$, $R_{1w}$, $RM_{0m}$, and $RM_{0w}$. These parameters can provide information on various tissue properties. Higher MT powers can saturate macromolecular protons more effectively, allowing more accurate MT modeling. However, proper consideration should be given to the MT powers that are used because higher MT power will generate higher specific absorption ratio (SAR), which can be problematic, especially for in vivo studies. Therefore, powers up to 1500° with a TR of 100 ms represents a good balance between high saturation efficiency and SAR limitation for in vivo imaging of the tibial midshaft. For MT modeling, the acquired data with a wide range of saturation including high saturation to non-saturation conditions are needed for accurate model fitting since there are a total of five fitting parameters. The macromolecular components have a broad lineshape with a $T_2$ around a few microseconds. Thus, a wide range of off-resonance frequencies from 2 KHz to 50 KHz and MT powers from 300° to 1500° can generate a broad range of signal saturation. To achieve relatively accurate MT modeling, the lowest off-resonance frequency is chosen in order to avoid directly saturating the water pool. Therefore, the lowest off-resonance frequency for MT modeling of short $T_2$ tissues such as cortical bone (e.g., minimal off-resonance frequency offset of 2 KHz) is higher than that of long $T_2$ tissues such as white matter and optic nerve (e.g., 1 KHz).

The bound or macromolecular fraction is a measure particularly unique to quantitative MT modeling. For example, it was observed that mean macromolecular fractions of 59.9±7.3% and 54.5±4.9% in ex vivo bovine and in vivo human tibial cortical bone, respectively. The corollary of these example results is in keeping with previous measures of total water content (17.4-24.8%) among in vivo human tibial cortical bone studies. Based on NMR experiments in human cortical bone, greater than 80% of signal contributions from this observed proton fraction would be expected to correspond with collagen methylene. Since serum and urine collagen degradation products seen with increased bone resorption may be confounded by various factors such as circadian rhythm, fracture healing and others, cortical bone bound fraction might be complementary to existing methods used for treatment monitoring and fracture risk prediction. The disease specificity of such a measure however must be determined in patient studies prior to forming a conclusion on the clinical use of quantitative UTE-MT in cortical bone.

In this study, the five MT modeling parameters include f, $T_{2m}$, $R_{1w}$, $RM_{0m}$, and $RM_{0w}$, which can be potentially useful biomarkers, especially considering that those biomarkers are insensitive to the magic angle effect. Conventional $T_2$ and $T_{1rho}$ may increase by several fold when the collagen fibers are reoriented from 0° to 55° (the magic angle) relative to the $B_0$ field, while the MT modeling parameters are relatively constant with less than 10% increase near the magic angle. The UTE-MT modeling parameters may be useful in the diagnosis and treatment monitoring of osteoporosis, where the macromolecular proton fraction was expected to inversely correlate with cortical porosity. Other MT modeling parameters such as relaxation times and exchange rates may also be correlated with bone properties.

Example 11: Quantitative UTE-MT Imaging Using a Time-Efficient 3D Multi-Spoke Cones Sequence In some implementations, an example embodiment of a three-dimensional ultrashort echo time magnetization transfer (UTE-MT) MR imaging and modeling method was employed, The example implementations demonstrated accelerating quantitative ultrashort echo time imaging using a time-efficient three-dimensional multi-spoke cones sequence with magnetization transfer (3D UTE-Cones-MT) and signal modeling.

The example study included a 3D UTE-Cones-MT acquisition scheme with multi-spoke per MT preparation and a modified rectangular pulse (RP) approximation for two-pool MT modeling of macromolecular and water components including their relative fractions, relaxation times and exchange rates. Numerical simulation and cadaveric specimens, including human Achilles tendon and bovine cortical bone, were investigated using a clinical 3T scanner.

The example results included numerical simulation that showed that the modified RP model provided accurate estimation of MT parameters when multi-spokes were acquired per MT preparation. Also for example, the example results showed, for the Achilles tendon and cortical bone samples, macromolecular fractions were 20.4±2.0% and 59.4±5.3%, respectively. The example 3D multi-spoke UTE-Cones-MT sequence can be used for fast volumetric assessment of macromolecular and water components in short T2 tissues.

Conventional clinical MRI sequences can only assess tissues with relatively long transverse relaxation times (T2s). Many joint tissues or tissue components, such as the deep radial and calcified cartilage, menisci, ligaments, tendons and bone have short transverse relaxation times and show little or no signal with clinical sequences. Ultrashort echo time (UTE) sequences, with echo times (TEs) less than 0.1 ms, have been been used on clinical MR scanners to directly image collagen-rich short T2 tissues or tissue components. However, these tissues contain not only water, but macromolecule components such as collagen and proteoglycans (PGs). These macromolecules have extremely fast signal decay and remain "invisible" with all conventional clinical sequences as well as UTE sequences. Quantifying both water and macromolecule components in both short and long T2 tissues, rather than just focusing on water in the longer T2 components in one specific tissue (e.g., articular cartilage), is likely to improve the sensitivity of MRI for the early diagnosis of osteoarthritis (OA).

Conventional MT sequences employ off-resonance saturation pulses to selectively saturate the proton magnetization of immobile macromolecules and indirectly saturate the magnetization of water protons. The simplest approach is to measure magnetization transfer ratio (MTR) which provides a measure of the magnetization change before and after the MT pulse. Reduction of MTR has been shown to be associated with collagen degradation and PG depletion. However, the measured MTR depends on many factors such as the specific details of the pulse sequence (e.g., MT power and frequency offset) and hardware, and does not provide quantitative information on macromolecular and water components in tissues.

The example MT modeling techniques in accordance with the present technology can provide lots of quantitative information, such as the fractions, relaxation times and exchange rates of different proton pools, which can be more promising than MTR in clinical use. For example, the MT modeling parameters are magic angle insensitive, as shown in earlier examples in this disclosure, e.g., with respect to Achilles tendon samples using a 2D UTE-MT sequence, where tendon T2* varied by more than 7-fold while fractions and exchange rates varied by less than 10% when the sample orientation was changed from 0° to 55° relative to the $B_0$ field.

Conventional quantitative MT techniques are not applicable to short T2 tissues such as tendons and cortical bone. Furthermore, multiple series of MT datasets with different MT powers and frequency offsets need to be acquired for MT modeling. This can be very time consuming, especially when volumetric imaging is used. An extension of the original Sled and Pike RP model, which accounts for multi-spoke acquisition may be appropriate for modeling. In this example study, a three-dimensional multi-spoke UTE Cones MT sequence (3D UTE-Cones-MT) and a modified RP model to accelerate quantitative MT imaging is implemented for Achilles tendon and cortical bone using a clinical 3T whole-body scanner.

Two-pool MT model divides the spins within a biological tissue into two pools: (1) a water pool composed of water protons and (2) a macromolecular pool that includes macromolecular protons. Each pool has its own set of intrinsic relaxation times. Magnetization exchange between the pools is modeled by a first-order rate constant (R). Equations [D1]-[D4], based on Henkelman's equations, describe modified Bloch equations into the mathematical description of the MT phenomenon by utilization of non-Lorentzian lineshapes for the macromolecular pool, which are shown as follows:

$$\frac{dM_z^w}{dt} = R_{1w}(M_0^w - M_z^w) - RM_0^m M_z^w + RM_0^w M_z^m + w_1 M_y^w \quad [D1]$$

-continued $$\frac{dM_z^m}{dt} = R_{1m}(M_0^m - M_z^m) - RM_0^w M_z^m + RM_0^m M_z^w - R_{RFm}(w_1, \Delta f)M_z^m \quad [D2]$$

$$\frac{dM_x^w}{dt} = -\frac{M_x^w}{T_{2w}} - 2\pi \Delta f M_y^w \quad [D3]$$

$$\frac{dM_y^w}{dt} = -\frac{M_y^w}{T_{2w}} + 2\pi \Delta f M_x^w - w_1 M_z^w \quad [D4]$$

where $M_0^{w,m}$ are the fully relaxed magnetization of water and macromolecular pools, respectively; $M_{x,y,z}^{w,m}$ are the x, y and z components of the magnetization of water and macromolecular pools, respectively; $w_1$ is the angular frequency of precession induced by the off-resonance MT pulse; $\Delta f$ is the frequency offset of the MT pulse in $H_z$; $R_{1w,1m}$ are the longitudinal rate constants and $T_{2w,2m}$ are the transverse relaxation times; and $R_{RFm}$ is the rate of longitudinal magnetization loss of the macromolecular proton pool due to the direct saturation of the MT pulse, which is related to the absorption lineshape $G(2\pi\Delta f)$ of the spins in the macromolecular pool. $R_{RFm}$ is given by Equation [D5]:

$$R_{RFm} = \pi w_1^2 G(2\pi\Delta f) \quad [D5]$$

For example, since the protons in the macromolecular pool do not experience the motional narrowing which those in the free pool do, their spectrum cannot be characterized by a Lorentzian lineshape function. Gaussian and super-Lorentzian lineshapes can provide good representations for the macromolecular pool. The Gaussian and super-Lorentzian lineshapes are expressed in Equations [D6] and [D7] as $G_G(2\pi\Delta f)$ and $G_{sL}(2\pi\Delta f)$, respectively:

$$G_G(2\pi\Delta f) = \frac{T_{2m}}{\sqrt{2\pi}} \exp\left(-\frac{[2\pi\Delta f T_{2m}]^2}{2}\right), \quad [D6]$$

$$G_{sL}(2\pi\Delta f) = \int_0^{\pi/2} d\theta \sin\theta \sqrt{\frac{2}{\pi}} \frac{T_{2m}}{|3\cos^2\theta - 1|} \exp\left(-2\left[\frac{2\pi\Delta f T_{2m}}{|3\cos^2\theta - 1|}\right]^2\right), \quad [D7]$$

where $\theta$ is the angle between the $B_0$ and the axis of molecular orientation.

A two-pool MT model was proposed by Sled and Pike for pulsed imaging to simplify Equations [D1]-[D7]. In this example study, their model for multi-spoke pulsed imaging (e.g., one MT pulse preparation followed by multiple acquisitions) is modified to reduce the data acquisition time. For example, the effect of an MT pulse on the macromolecular pool is modeled as a rectangular pulse (RP) approximation whose width is equal to the full width at half maximum of the curve obtained by squaring the MT pulse throughout its duration. The rectangular pulse has equivalent average power to that of the original MT pulse. On the other hand, the effect of the MT pulse on the water pool is modeled as an instantaneous fractional saturation of the longitudinal magnetization. Such instantaneous saturation ($S_{1w}$) is estimated by numerically solving Eqs. [D1], [D3] and [D4] when R and $R_{1w}$ are set to 0. For the excitation pulses, the instantaneous saturation of water component is $\cos^{N_{sp}}(\alpha)$, where $\alpha$ is the excitation flip angle and $N_{sp}$ is the number of spokes or excitations after each MT pulse preparation. This implies that the saturation effects of all the excitation pulses occurred precisely at the middle of the RP pulse. The original Sled and Pike RP model is a specific case of the modified model with $N_{sp}=1$.

Equations [D1] and [D2] can be written in matrix form, as shown in Equation [D8]:

$$\frac{dM_z(t)}{dt} = AM_z(t) + BM_0 \quad [D8]$$

where, $$M_z(t) = \begin{bmatrix} M_z^w(t) \\ M_z^m(t) \end{bmatrix} \text{ and } M_0 = \begin{bmatrix} M_0^w \\ M_0^m \end{bmatrix}.$$

A and B are the matrices corresponding to the coefficients in Equations [D1] and [D2]. For example, here, only the longitudinal components are considered for computation, and the transverse components are assumed to be negligible due to relaxation and spoiling.

Thus, instantaneous saturation of water pool, caused by both MT and excitation pulses, is described by multiplying $M_z$ by the saturation matrix S:

$$S = \begin{bmatrix} S_{1w}\cos^{N_{sp}}(\alpha) & 0 \\ 0 & 1 \end{bmatrix}. \quad [D9]$$

After instantaneous saturation, the longitudinal magnetization becomes (for example, assuming starting time $t_0$):

$$M_z(t_0) = SM_z(t_0). \quad [D10]$$

The longitudinal magnetization after a period $t_1$ is given by the matrix form solution of equations associated with Equation [D8] for either continuous wave (CW) or free precession (FP):

$$M_z(t_0 + t_1) = \exp(A_{CW}t_1)M_z(t_0) + [\exp(A_{CW}t_1) - I]A_{CW}^{-1}BM_0 \quad [D11]$$

$$M_z(t_0 + t_1) = \exp(A_{FP}t_1)M_z(t_0) + [\exp(A_{FP}t_1) - I]A_{FP}^{-1}BM_0 \text{ with:} \quad [D12]$$

$$A_{CW} = \begin{bmatrix} -R_{1w} - RM_0^m & RM_0^w \\ RM_{0m} & -R_{1m} - RM_0^w - R_{RFm} \end{bmatrix},$$

$$A_{FP} = \begin{bmatrix} -R_{1w} - RM_0^m & RM_0^w \\ RM_0^m & -R_{1m} - RM_0^w \end{bmatrix}$$

$$B = \begin{bmatrix} R_{1w} & 0 \\ 0 & R_{1m} \end{bmatrix}$$

According to the RP approximation, for example, during the time interval (e.g., one TR) between adjacent MT pulses, $M_z$ successively undergoes instantaneous saturation, CW irradiation for a period $\tau_{RP}/2$, FP for a period $(TR-\tau_{RP})$ and CW for another $\tau_{RP}/2$. Within a steady state, the equality is generated, expressed in Equation [D13]:

$$M_z(TR+t_0) = M_z(t_0). \quad [D13]$$

$M_z$ can be obtained by solving this equation in matrix form. Finally, the observed signal $SI(w_1, \Delta f)$ is given as follows:

$$SI(w_1, \Delta f, \alpha) = M_z^w(t_0)S_{1w}\sin(\alpha). \quad [D14]$$

In this example, there are in total seven parameters (e.g., $M_0^w$, $R_{1w}$, $R_{1m}$, $RM_0^m$, f, $T_{2w}$, $T_{2m}$) in the final expression. f is the macromolecular proton fraction defined as $$\frac{M_0^m}{M_0^m + M_0^w}.$$

$R_{1m}$ is fixed to 1 s$^{-1}$ without affecting fitting results of other parameters. In addition, if $R_{1obs}(=1/T_1)$ is known, $R_{1w}$ can be obtained from other parameters, e.g., in Equation [D15]:

$$R_{1w} = R_{1obs} - \frac{RM_0^m(R_{1m} - R_{1obs})}{R_{1m} - R_{1obs} + \frac{RM_0^m(1-f)}{f}} \quad [D15]$$

The final number of independent parameters can be, therefore, reduced to five, which can be estimated by fitting Equation [D13] using five or more measurements with different combinations of $w_1$ and $\Delta f$.

In this example, according to the RP approximation, $M_z$ successively undergoes instantaneous saturation (e.g., S), CW irradiation for a period of half RP duration $\tau_{RP}/2$, FP for a period (TR−$\tau_{RP}$) and CW for another half RP duration $\tau_{RP}/2$ in a TR. The following is the magnetization precession in a TR (assuming $t_0=0$ for simplification):

$$M_z(0) = SM_z(0) \quad [D16]$$

$$M_z\left(\frac{\tau_{RP}}{2}\right) = \exp\left(\frac{A_{CW}\tau_{RP}}{2}\right)M_z(0) + \left[\exp\left(\frac{A_{CW}\tau_{RP}}{2}\right) - I\right]A_{CW}^{-1}BM_0 \quad [D17]$$

$$M_z\left(TR - \frac{\tau_{RP}}{2}\right) = \quad [D18]$$
$$\exp[A_{FP}(TR - \tau_{RP})]M_z\left(\frac{\tau_{RP}}{2}\right) + \{\exp[A_{FP}(TR - \tau_{RP})] - I\}A_{FP}^{-1}BM_0$$

$$M_z(TR) = \quad [D19]$$
$$\exp\left(\frac{A_{CW}\tau_{RP}}{2}\right)M_z\left(TR - \frac{\tau_{RP}}{2}\right) + \left[\exp\left(\frac{A_{CW}\tau_{RP}}{2}\right) - I\right]A_{CW}^{-1}BM_0.$$

Within a steady state, the equality is generated:

$$M_z(TR) = M_z(0). \quad [D20]$$

After solving for Equations [D16]-[D20], the signal of $M_z$(TR) is shown as follows:

$$M_z(TR) = \frac{[E_{CW}E_{FP}(E_{CW} - I)A_{CW}^{-1} + E_{CW}(E_{FP} - I)A_{FP}^{-1} + (E_{CW} - I)A_{CW}^{-1}]BM_0}{I - E_{CW}E_{FP}E_{CW}S} \quad [D21]$$

$$E_{CW} = \exp\left(\frac{A_{CW}\tau_{RP}}{2}\right)$$

$$E_{FP} = \exp[A_{FP}(TR - t_{RP})].$$

Then the final signal equation is expressed as follows in Equation [D22]:

$$SI(w_1, \Delta f, \alpha) = M_z(TR)_1 S_{1w} \sin(\alpha) \quad [D22]$$

where $M_z(TR)_1$ is the first matrix element (e.g., longitudinal relaxation of water component) of $M_z$(TR).

Figure 17A:
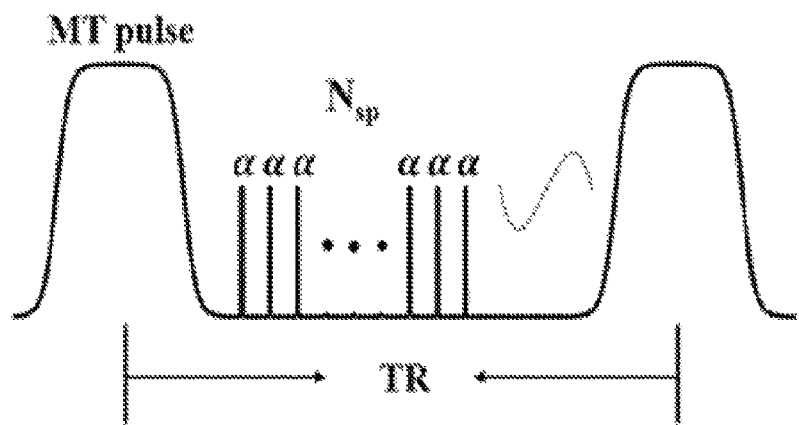
FIGS. 17A-17C show diagrams depicting an example 3D UTE-Cones-MT sequence implemented on an MRI scanner.
Figure 17B:
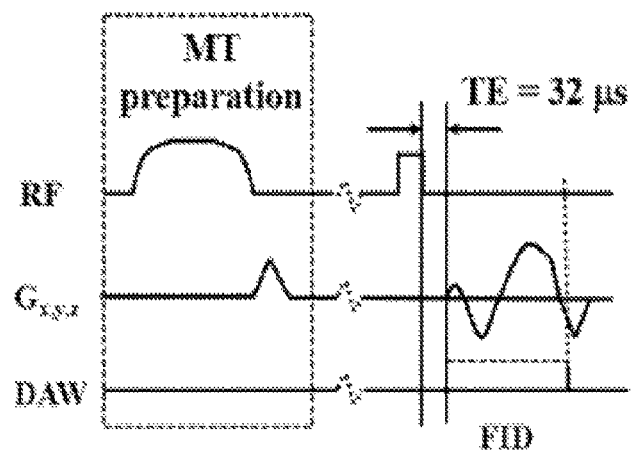
Figure 17C:
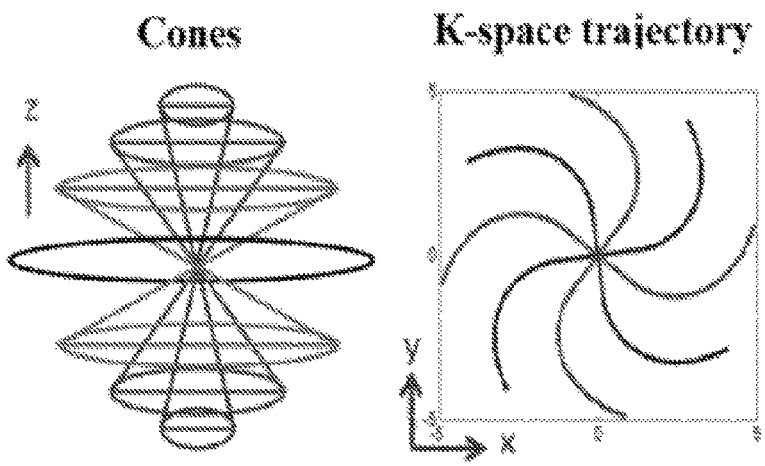

FIGS. 17A-17C show diagrams depicting an example 3D UTE-Cones-MT sequence implemented on an MRI scanner, e.g., 3T Signa TwinSpeed scanner (GE Healthcare Technologies). The diagram of FIG. 17A depicts a Fermi pulse was used for MT preparation followed by multiple spokes ($N_{sp}$) excitation. For example, each excitation employs a short rectangular pulse (e.g., duration=26 μs) for signal excitation, depicted in FIG. 17B. This was followed by a 3D Cones trajectory, shown in FIG. 17C, to allow time-efficient sampling with a minimal TE of 32 μs. Data acquisition window (DAW) starts at the beginning of the readout gradient. The example 3D UTE-Cones sequence allows for anisotropic resolution (e.g., high in-plane resolution and thicker slices) for much improved signal-to-noise ratio (SNR) and reduced scan time relative to isotropic imaging. The MT preparation pulse was a Fermi pulse of 8 ms duration (spectral bandwidth=0.8 kHz), maximal $B_1$ of 24 μT and 1740° maximal saturation flip angle, which provided an improved spectral profile compared with a rectangular pulse and higher efficiency (e.g., larger duty cycle) compared with Gaussian pulse. The 3D Cones images acquired with a series of MT pulse powers and off-resonance frequencies were used for two-pool MT modeling.

Generally, MT modeling requires repeated data acquisition with a series of MT powers and frequency offsets, the associated long scan time is a big challenge. To reduce total scan time, for example, the example 3D UTE-MT method several spiral spokes ($N_{sp}$) can be acquired after each MT preparation pulse (total scan time being reduced by a factor of $N_{sp}$). This time efficiency greatly benefits clinical applications. The accuracy of this approach was evaluated via simulation (details below).

The following example MT parameters were used to compare the example modified RP model with both the original Sled and Pike RP model and conventional CWPE mode with Bloch simulations from Equations [D1]-[D4]. The following parameters were used in the simulation: $M_0^w=1$, $R_{1w}=1.4$ s$^{-1}$, $R_{1m}=1$ s$^{-1}$, $RM_0^m=5$ s$^{-1}$, f=0.2, $T_{2w}=6$ ms, $T_{2m}=10.4$ μs. Both Gaussian and Super-Lorentzian lineshapes for the macromolecular pool were tested. The sequence parameters were as follows: TR=100 ms, Flip angle=7°, MT powers=500 and 1500°, 30 MT frequency offsets from 2 KHz to 50 KHz, and $N_{sp}$ from 1 to 11. A Fermi pulse (duration=8 ms, bandwidth=160 Hz) was used for MT saturation. The duration between MT and the first excitation pulse was 5 ms. The duration between two adjacent excitation pulses was also 5 ms.

Three human Achilles tendon specimens and three mature bovine cortical bone samples were used for evaluation of the 3D UTE-Cones-MT modeling with different excitation spokes. A custom-built 1-inch solenoid coil was used for the Achilles tendon samples. A wrist coil (BC-10, Medspira) was used for cortical bone samples. The Cones-MT imaging protocol included: TR=100 ms, TE=32 μs, flip angle=7°, FOV=10×10×5 cm$^3$ for cortical bone (e.g., 5 mm slice thickness) and 8×8×2 cm$^3$ for tendon (2 mm slice thickness), acquisition matrix=128×128×10; $N_{sp}$ from 1 to 11 to test the modified RP model, the duration of each spoke is 4.8 ms and readout bandwidth is 125 KHz; three MT powers (300°, 700° and 1100°) and five MT frequency offsets (2, 5, 10, 20 and 50 kHz), with a total of 15 different MT datasets. The total scan time was 59.5, 19.8, 12, 8.5, 6.8 and 5.5 min corresponding to $N_{sp}$=1, 3, 5, 7, 9 and 11, respectively. $T_1$ was measured using a 3D UTE-Cones acquisition with the same spatial resolution and a series of TRs (6, 15, 30, 50, 80 ms) with a fixed flip angle of 25° in a total scan time of 7.2 min.

The analysis algorithm was written in Matlab (The MathWorks Inc.) and was executed offline on the DICOM images obtained by the 3D UTE-Cones-MT protocols described above. Two-pool UTE-Cones-MT modeling and parameter mapping were performed on the tendon and bone samples. Mean and standard deviation of macromolecular proton fraction, relaxation time, exchange rates and water longitudinal relaxation were calculated. The example results included the following.

Figure 18:
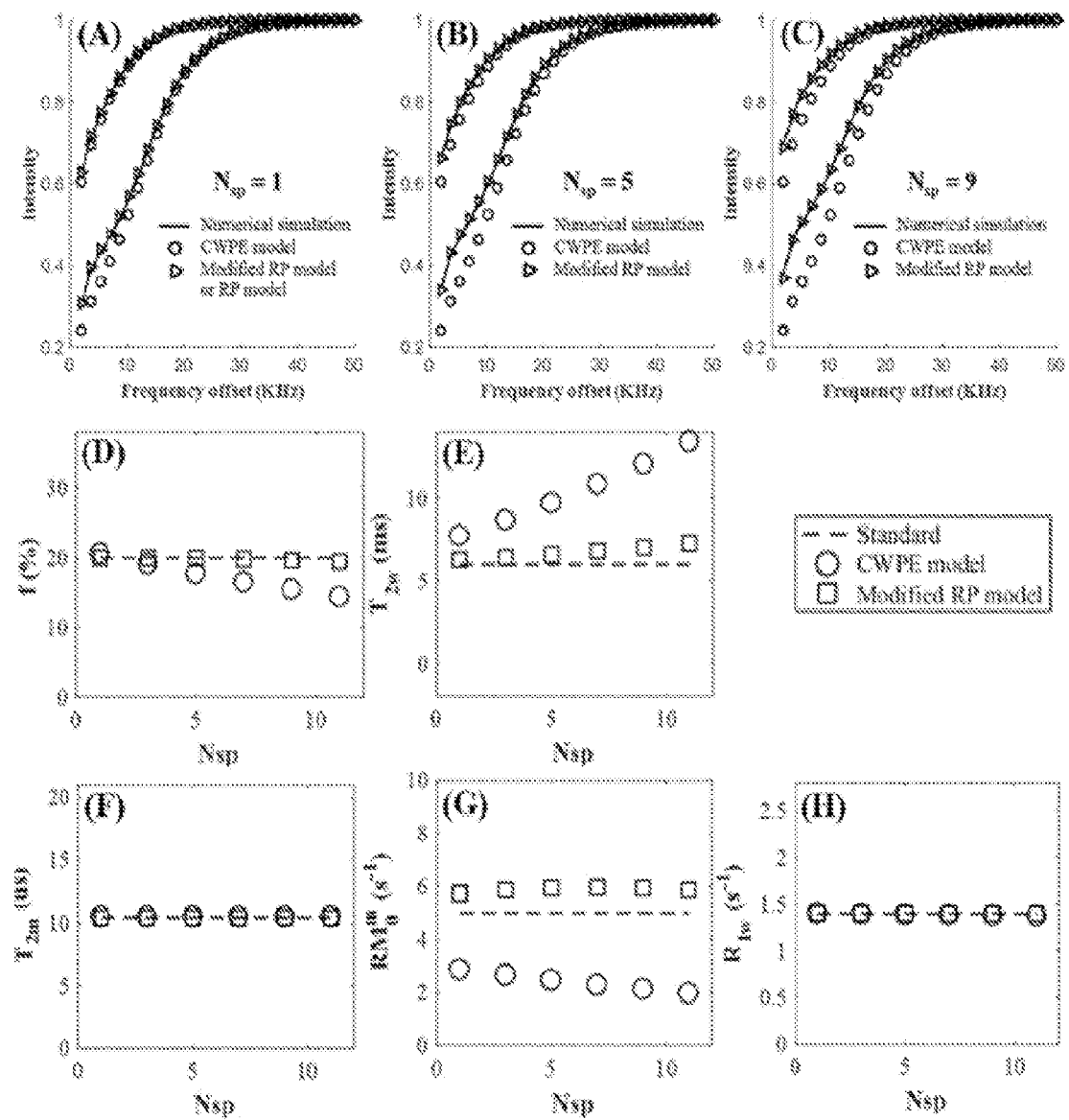
FIG. 18 shows simulations of an example two-pool MT model with a Super-Lorentzian lineshape.

FIG. 18 shows simulations of an example two-pool MT model with a Super-Lorentzian lineshape, and a series of $N_{sp}$ ranging from 1 to 11. The MT parameters were obtained from both RP and CWPE models by fitting the numerical simulated data. For the simulations shown in FIG. 18, simulation on two-pool modeling of MT data acquired with two MT powers (e.g., 500° and 1500°) and a series of frequency offsets ranging from 2 to 50 kHz for a $N_{sp}$ of 1 (A), 5 (B), and 9 (C) using a Super-Lorentzian lineshape. The modified RP model fits much better than the CWPE model. MT parameters including f (D), $T_{2w}$ (E), $T_{2m}$ (F), $RM_{0w}$ (G) and $R_{1w}$ (H) are plotted against $N_{sp}$ ranging from 1 to 11. MT parameters derived from the modified RP model show little variability with $N_{sp}$, while those from the CWPE model show significant variation with $N_{sp}$.

The example modified RP model outperformed the CWPE model especially when more spokes were acquired per MT preparation. For a representative $N_{sp}$ of 9, the CWPE model underestimated macromolecule fraction by more than 25% and $RM_0^m$ by 60%, and overestimated $T_{2w}$ by more than 50%. In comparison, for example, the modified RP model can accurately estimate all these parameters, with less than 3% error for f, $T_{2m}$ and $R_{1w}$. Slightly increased errors were observed for $T_{2w}$ and $RM_0^m$, but still less than 10% for a $N_{sp}$ of 9. Very similar results were observed for the Gaussian lineshape, as shown in FIG. 19.

Figure 19:
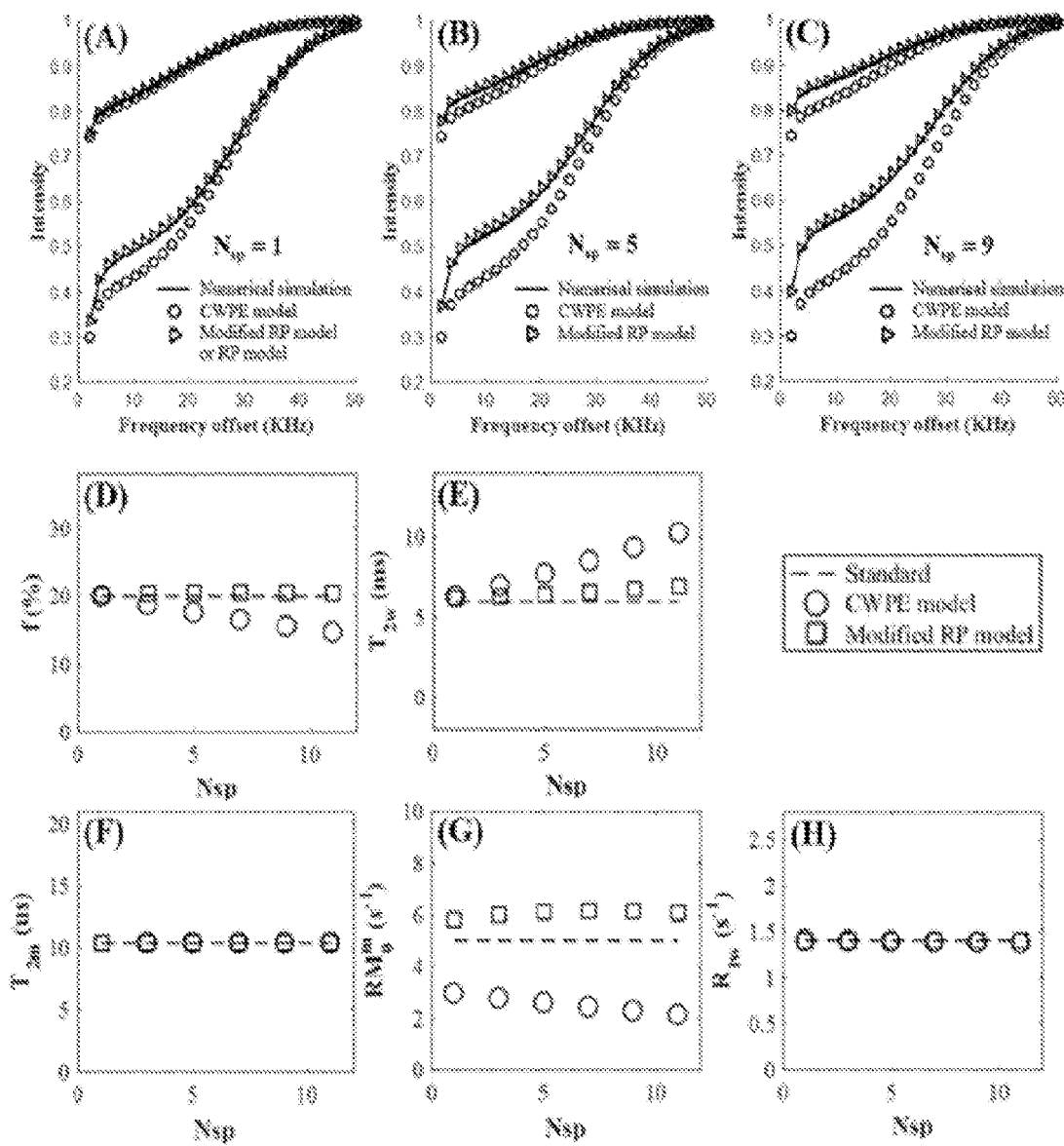
FIG. 19 shows simulations of an example two-pool MT model with a Gaussian lineshape.

FIG. 19 shows simulations of an example two-pool MT model with a Gaussian lineshape, and a series of $N_{sp}$ ranging from 1 to 11. The MT parameters were obtained from both RP and CWPE models by fitting the numerical simulated data. For the simulations shown in FIG. 19, simulation on two-pool modeling of MT data acquired with two MT powers (e.g., 500° and 1500°) and a series of frequency offsets ranging from 2 to 50 kHz for a $N_{sp}$ of 1 (A), 5 (B), and 9 (C) using a Gaussian lineshape. The modified RP model fits much better than the CWPE model. MT parameters including f (D), $T_{2w}$ (E), $T_{2m}$ (F), $RM_{0w}$ (G) and $R_{1w}$ (H) are plotted against $N_{sp}$ ranging from 1 to 11. MT parameters derived from the modified RP model show little variability with $N_{sp}$, while those from the CWPE model show significant variation with $N_{sp}$.

Figure 20:
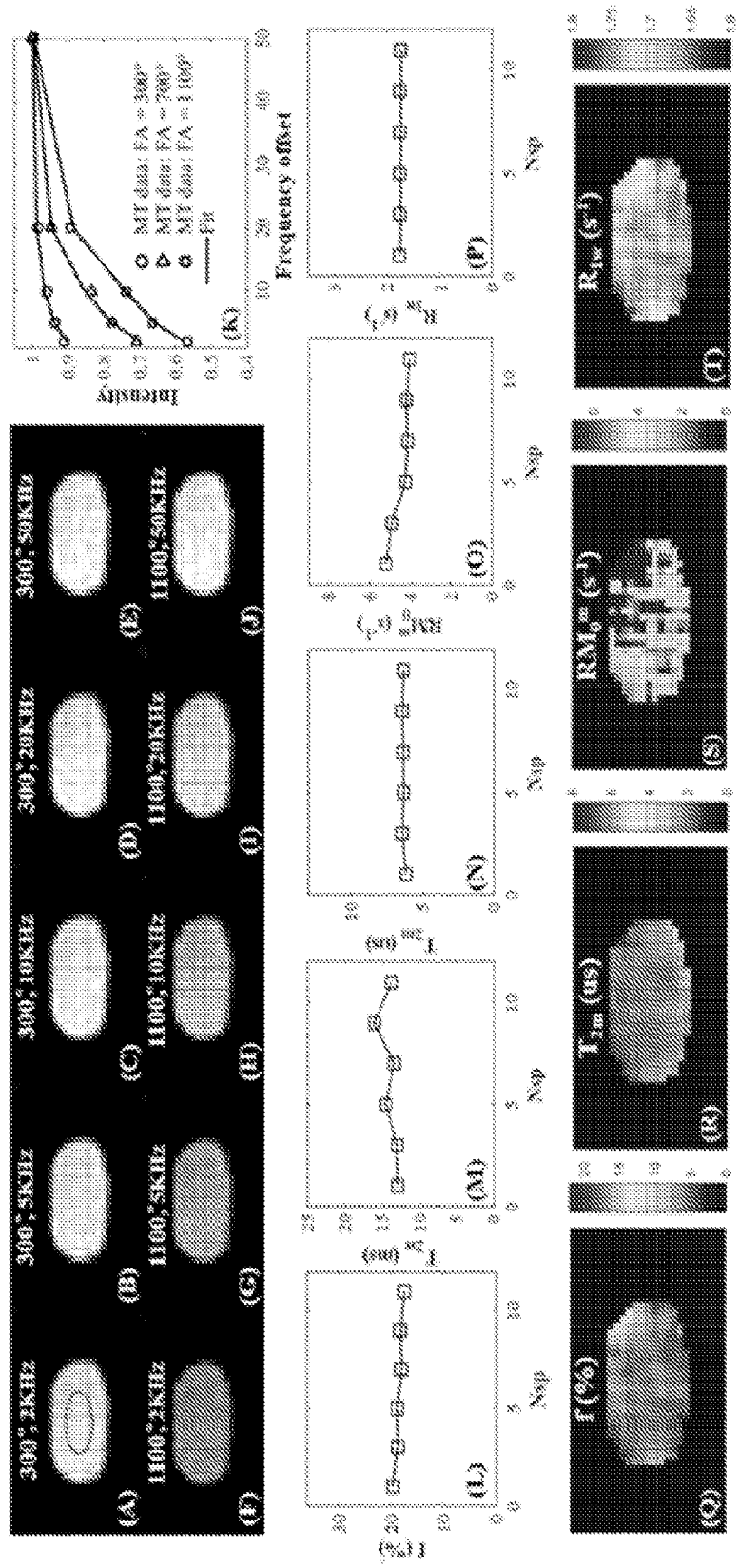
FIG. 20 shows example 3D UTE-Cones-MT images of a human Achilles tendon sample with two different MT powers and five off-resonance frequencies.

FIG. 20 shows selected 3D UTE-Cones-MT images of a human Achilles tendon sample with two different MT powers (e.g., 300° and 1100°) and five off-resonance frequencies (e.g., 2, 5, 10, 20, 50 kHz). Specifically, the example 3D Cones-MT images of a cadaveric human Achilles tendon sample were acquired with an MT power of 300° and frequency offsets of 2 kHz (A), 5 kHz (B), 10 kHz (C), 20 kHz (D), 50 kHz (E), as well as an MT power of 1100° and five frequency offsets of 2 kHz (F), 5 kHz (G), 10 kHz (H), 20 kHz (I), 50 kHz (J) with $N_{sp}$=9. The clinically MR "invisible" Achilles tendon showed high signal on all Cones-MT images, allowing accurate two-pool MT modeling as shown in FIG. 20, panel (K), e.g., excellent two-pool fitting was achieved with the modified RP model. A Super-Lorentzian lineshape was used for MT modeling. The MT parameters were relatively constant with different $N_{sp}$, further demonstrating the robustness of our new, modified RP model. MT parameters including f (L), $T_{2w}$ (M), $T_{2m}$ (N), $RM_{0w}$ (O), $R_{1w}$ (P) are displayed as a function of $N_{sp}$. Selected mapping of f (Q), $T_{2m}$ (R), $RM_{0m}$ (S) and $R_{1w}$ (T) are also displayed. $RM_{0m}$ showed increased variation likely due to the greater uncertainty in estimating this parameter using the modified RP model. The high quality UTE-Cones-MT images also allowed for mapping of two-pool MT parameters. $RM_{0m}$ showed increased variation suggesting that this parameter was subject to greater uncertainty. The MT modeling results ($N_{sp}$=9) of the three Achilles tendon samples were as follows: f=20.4±2.0%, $T_{2m}$=7.1±0.9 µs, $RM_0^m$=2.9±1.2 s$^{-1}$ and $R_{1w}$=1.7±0.1 s$^{-1}$ with $T_1$=639.7±49.9 ms. The example results were similar to previous reported results especially for the macromolecular fractions.

Figure 21:
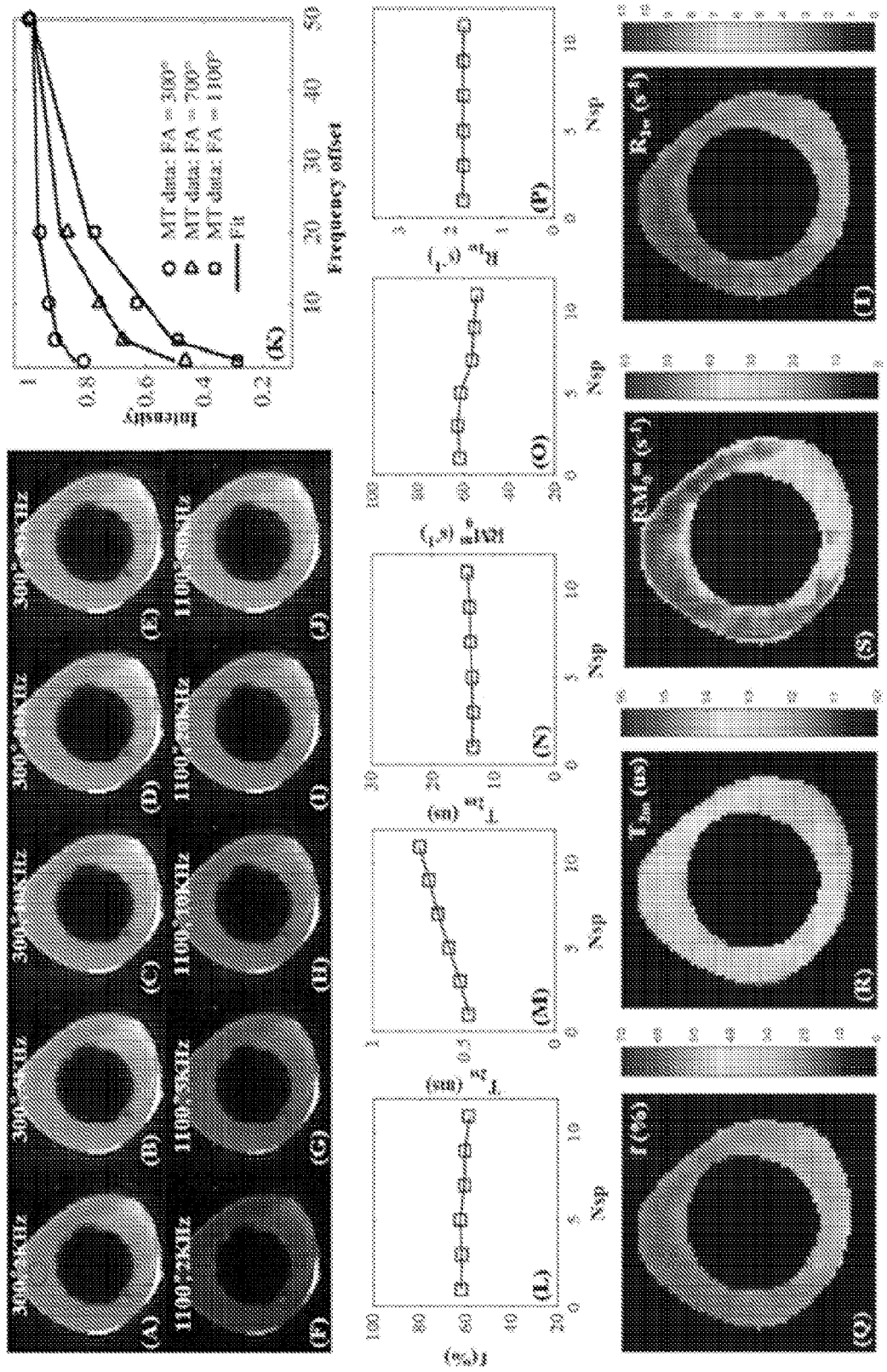
FIG. 21 shows selected 3D UTE-Cones-MT images of a cortical bone sample with two different MT powers and five off-resonance frequencies.

FIG. 21 shows selected 3D UTE-Cones-MT images of a cortical bone sample with two different MT powers (e.g., 300° and 1100°) and five off-resonance frequencies (e.g., 2, 5, 10, 20, 50 kHz). The example 3D Cones-MT images of a cadaveric bovine cortical bone sample were acquired with an MT power of 300° and five frequency offsets of 2 kHz (A), 5 kHz (B), 10 kHz (C), 20 kHz (D), 50 kHz (E), as well as an MT power of 1100° and five frequency offsets of 2 kHz (F), 5 kHz (G), 10 kHz (H), 20 kHz (I), 50 kHz (J) with $N_{sp}$=9. Cortical bone was depicted with high signal and spatial resolution on all UTE-Cones-MT images. The collagen in cortical bone is more solid-like in comparison to typical soft tissues such as tendon, therefore we employed the Gaussian lineshape in cortical bone for two-pool MT modeling. The MT parameters for bovine cortical bone were relatively constant with different $N_{sp}$, except for one parameter, $T_{2w}$, which showed increased error with increase of $N_{sp}$ (~40% overestimation for a $N_{sp}$ of 9) e.g., excellent two-pool fitting was achieved with the modified RP model, FIG. 21, panel (K). The lower half of this bovine cortical bone sample showed increased signal intensity, which was in consistent with the reduced collagen proton fraction, $RM_0^m$ and $R_{1w}$. The MT modeling results ($N_{sp}$=9) of the three cortical bones samples were as follows: f=59.4±5.3%, $T_{2m}$=13.9±0.6 µs, $RM_0^m$=34.2±15.0 s$^{-1}$ and $R_{1w}$=9.9±0.6 s$^{-1}$ with $T_1$=237.7±16.7 ms. The MT parameters including f (L), $T_{2w}$ (M), $T_{2m}$ (N), $RM_{0w}$ (O), $R_{1w}$ (P) are displayed as a function of $N_{sp}$. Selected mapping of f (Q), $T_{2m}$ (R), $RM_{0m}$ (S) and $R_{1w}$ (T) are also displayed. The lower half of this bone sample showed greater variation in Cones image signal intensity and MT parameters which may need further investigation.

Generally, MT modeling requires data acquisitions with several saturation pulse powers and frequency offsets. It may lead to excessively long scan time, making it difficult for clinical translation. For example, if one scan were to last 1 minute, then conventional MT modeling procedures can lead total scan times take or even exceed an hour, which is clinically impractical in implementation. Moreover, typical, 3D UTE-Cones-MT imaging is even more time-consuming because of the high MT power (e.g., >1000°) which requires a relatively long TR to reduce SAR and a large number of volumetric encoding steps.

The methods and systems in accordance with the present technology include a fast multi-spoke acquisition scheme for 3D UTE-Cones-MT imaging and modified the RP model to fit the multi-spoke pulsed MT sequence. For example, more than 59.5 minutes would be needed for the acquisition of 15 MT datasets if only one spoke was acquired per MT preparation. With the introduction of the multi-spoke approach (e.g., 9) per MT preparation, the total scan time for UTE-Cones-MT modeling can be reduced to less than 6.8 minutes, which is clinically feasible.

To reduce errors associated with the example multi-spoke approach, the modified RP model was developed and validated in the example study, which was shown to perform much better than the widely used CWPE model. For example, the modified RP model resulted in nearly constant macromolecular fraction f, $T_{2m}$, $R_{1w}$ and $RM_{0m}$, although $T_{2w}$ showed greater errors with increasing $N_{sp}$. The example 3D multi spoke UTE-Cones-MT sequence together with the modified two-pool RP modeling largely preserved accuracy in estimating macromolecular and water fractions, relaxation times and exchange rates. Further, the example model might be more broadly applicable in that it may be applied to other segmented gradient echo sequences (e.g., such as FLASH), in addition to the UTE-Cones sequence.

The example study produced results that were largely consistent with the results from the literature. For example, in some implementations, two MT powers for MT modeling may be needed, e.g., which can reduce scan time by using only two MT powers. Higher MT powers can saturate macromolecular protons more effectively, allowing more accurate MT modeling. However, proper consideration should be given to the MT powers that are used because higher MT power will generate higher SAR, which can be problematic, especially for in vivo studies. The example study focused on the MT effect in short T2 tissues such as cortical bone and the Achilles tendons, which are "invisible" with conventional clinical MRI sequences. The example results showed that Fermi-shaped pulse with high duty cycle used in the example study is more efficient than Gaussian shaped pulses in saturating signal from short T2 tissues, facilitating MT modeling of water and macromolecular components in those tissues. Furthermore, for example, the Fermi shaped RF pulse is more similar to rectangular pulse than Gaussian shaped pulses, and is useful for the RP model. The macromolecular components have a broad lineshape with a T2 around a few microseconds. As such, for example, a wide range of off-resonance frequencies and MT powers can generate a broad range of signal saturation. For MT modeling, the acquired data with a wide range of saturation including high saturation to non-saturation conditions are needed for accurate model fitting since there are a total of five fitting parameters. In the example study, a Super-Lorentzian lineshape was used for the Achilles tendon, while a Gaussian lineshape was used for cortical bone which has a much shorter T2.

The example study demonstrated a reliable method including the combination of the 3D multi-spoke UTE-Cones-MT sequence and modified RP model for fast volumetric quantification of macromolecular and water components in short T2 tissues. By using a multi-spoke acquisition after each MT pulse, the example method was shown to be more time efficient than the original RP model, and showed higher accuracy compared with the CWPE model. The 3D UTE-Cones-MT sequence opens the door to systematic evaluation of short T2 tissues such as the deep radial and calcified cartilage, menisci, ligaments, tendons and cortical bone, including their macromolecular and water components. Importantly, these MT biomarkers are magic angle insensitive. The example technique is envisioned to provide considerable value for the early detection of diseases such as OA and for monitoring the effects of therapy.

Example 12: Quantitative UTE-MT Imaging and Modeling of Myotendinous Junction The myotendinous junction is an anatomic region in the muscle-tendon unit where tension generated by muscle fibers is transmitted from intracellular contractile proteins to extracellular connective tissue proteins (collagen fibrils) of the tendon. This highly specialized region has a distinct structure where muscle cells form deep recesses into which collagen fibrils attach, thereby increasing contact area between by 10 to 20-fold. This region is abundant in proteoglycans and glycosaminoglycans, including within the membranous ends of the myocte and on the tendinous site of the junction. The unique structure and composition increases the adhesive forces between the two structures and improves the elastic buffer capacity against loading. However, despite these adaptations, the myotendinous junction remains the weakest point in the muscle-tendon unit and is particularly susceptible to injury during powerful eccentric muscle contractions, where muscle activation occurs as muscle fibers lengthen. Myotendinous injuries are therefore most common in muscles that have a high percentage of fast-twitch fibers and also cross more than one joint, such as the hamstrings, quadriceps, and gastrocnemius muscles. The hamstrings are the most frequently injured. They function primarily by eccentric contraction, and a particularly common mechanism of injury involves ballistic hip flexion occurring during eccentric knee extension.

Myotendinous injuries are common in sports, particularly those that involve running. They represent about 48% of all injuries in track and field and more than 30% of injuries in soccer. For example, in basketball, players over a 17-year period were studied and it was found that lower extremity strains accounted for over 9% of injures (e.g., hamstring 3.3%, adductor 3.1%, triceps surae 2.1%, and quadriceps 0.8%). Other studies have also confirmed that the thigh and in particular the hamstring muscle groups were the most common regions to be strained in basketball players.

History, physical exam, and imaging all play important roles in contemporary evaluation of myotendinous injures. Traditional clinical classification is based on presentation, e.g., ranging from mild grade 1 injuries with minimal loss of structural integrity to severe grade 3 with complete ruptures. Imaging grading systems follow a similar scheme, whether using ultrasound or MRI. In more recent years, more detailed classification systems have been proposed, specifically for hamstring injuries. However, while MRI has been quite helpful for diagnosis of most myotendinous injuries, the prognostic capabilities have been less impressive. In fact, neither traditional clinical nor general MRI classification systems have been precisely correlated with RTP after a hamstring injury or with myotendinous injuries at other sites.

The existing challenges and troubles in effectively evaluating such musculoskeletal tissue like that involved in the myotendinous junction can include, among others, a number of important unresolved issues in the application of MRI to the diagnosis and management of myotendinous injuries. For example, (Challenge 1) the concept of grade 0 muscle injuries, where a clinical syndrome of muscle abnormality shows no imaging evidence of pathology. This likely represents a structural pathology that is below the sensitivity of current imaging modalities. Fortunately, these are associated with earlier RTP, but the imaging confirmation of this clinical diagnosis remains elusive. For example, (Challenge 2) conventional MRI techniques only provide information on long T2 components and thus current clinical interpretation focuses on the evaluation of edema, fluid, and hemorrhage rather than assessment of the injured/healing components of the myotendinous junction. While useful for diagnosis, this is particularly problematic for the management of myotendinous injuries when determining the time required to RTP. Studies have shown only a weak correlation between size of edema as seen on conventional MRI with time to RTP (r2=6-12%). For example, it was found that 89% of athletes with hamstring injuries still had increased intramuscular signal on fluid-sensitive sequences despite clinical recovery and successful return to play. In general, we know that resolution of edema is slower than functional recovery. For example, (Challenge 3) after injury, the majority of tendon and some of muscle healing is characterized by fibrovascular scarring. Fibrous tissue generally forms and matures much more rapidly for muscle compared with tendon. This partially explains why thigh injuries (either hamstrings or quadriceps) that extend to the tendinous portion of the myotendinous junction demonstrate prolonged rehabilitation time, increased time to return to full training, and are associated with a substantial increased risk of recurrence. Unfortunately, immature, collagen type III dominant fibrous tissue appears similar to mature, collagen type I dominant fibrous tissue on conventional MRI—both are characteristically hypointense on all sequences. This lack of signal precludes the opportunity for quantification with conventional MRI approaches. As such, those are unable to distinguish immature fibrous tissue, with its inferior biomechanical properties, from mature fibrous tissue or even normal tendon, all of which show little or no signal.

Example embodiments of the 3D UTE-MT Cones sequence-based MRI systems and methods in accordance with the present technology are envisioned to improve the characterization of tissues associated with the myotendinous junction. For example, example 3D UTE-Cones sequence techniques described herein have demonstrated TEs of 8 μs that are 100~1000 times shorter than the TEs of clinical sequences, which have allowed imaging the clinically MR "invisible" tissues (such as fibrous tissue and tendon) and tissue components (such as collagen). Using magnetization transfer (MT) imaging, water bound to macromolecules and protons in collagen with extremely short T2/T2* values (on the order of several μs) can be distinctly quantified. This information may allow for diagnosis of grade 0 muscle injuries, addressing Challenge (1), for example. In addition, by evaluating the conventionally MR "invisible" tissue components such as collagen and decoupling this information from fluid and edema, it may be possible to better discern the period of the regeneration process that is associated with functional recovery, thus addressing Challenge (2), for example. UTE-Cones-MT imaging may provide biomechanically-relevant information on shot T2/T2* tissues and tissue components. The application of this technique to distinguish the maturity of fibrovascular scar and visualize the muscle regeneration, ultimately with the goal of providing a non-invasive surrogate of biomechanical properties to guide RTP decisions is significant, and can address Challenge (3), for example.

Figure 22:
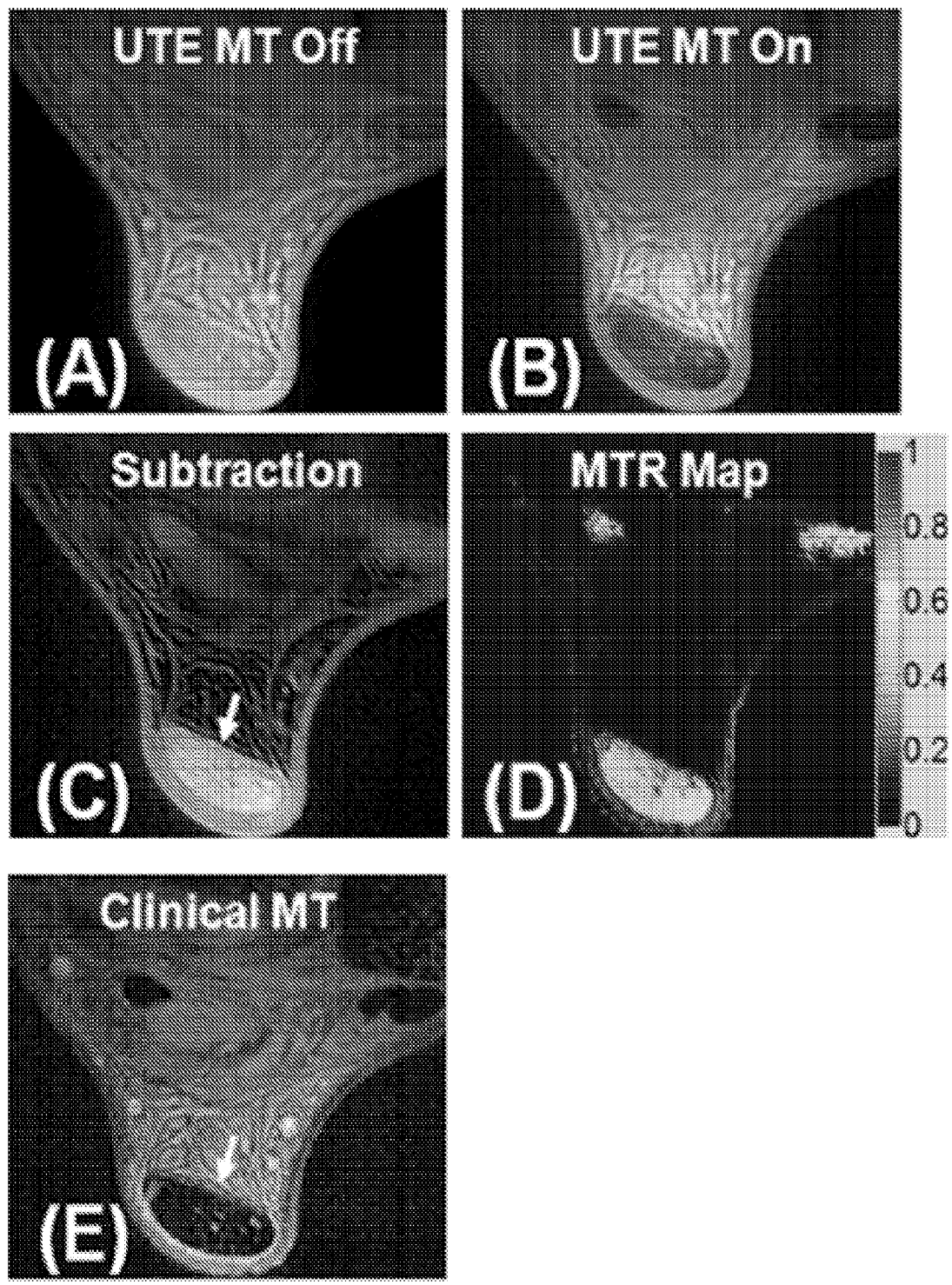
FIG. 22 shows example UTE and clinical MT imaging of an Achilles tendon.

FIG. 22 shows example UTE and clinical MT imaging of the Achilles tendon of a 54-year-old healthy volunteer. It demonstrates the feasibility of MT imaging of short T2 tissues. High resolution images were generated with an acquired voxel size of 0.2×0.2×2.0 mm$^3$ in under three minutes. The subtraction of UTE images without and with the MT pulse provides excellent depiction of tensile tendon. High quality MTR maps can be generated from UTE-MT imaging, while clinical GRE MT sequences provide only a signal void. The images of FIG. 22 show the example UTE-MT imaging of the Achilles tendon of a volunteer with the MT pulse off (panel A) and on (panel B), their subtraction (panel C), a MTR map (panel D) and clinical MT imaging (panel E). A MTR of ~40% was shown with UTE-MT, but was not assessable with clinical GRE MT sequences. UTE-MT sequences can quantify short T2 tissues in vivo.

UTE-MT imaging can be accelerated with multi-spoke acquisition per MT preparation. As previously shown in FIG. 20, example selected 3D UTE-Cones-MT images of a human Achilles tendon sample with two different MT powers (300° and 1100°) and five off-resonance frequencies (2, 5, 10, 20, 50 kHz) are shown. In the images of FIG. 20, the clinically MR "invisible" Achilles tendon showed high signal on all Cones-MT images, allowing accurate two-pool MT modeling as shown in panel K of FIG. 20. A Super-Lorentzian lineshape was used for MT modeling, and the MT parameters were relatively constant with different Nsp, further demonstrating the robustness of the new rectangular pulse (RP) model. The high quality UTE-Cones-MT images allow for volumetric mapping of two-pool MT parameters. For example, the RM0m showed increased variation suggesting that this parameter is subject to greater uncertainty, and the MT modeling results (Nsp=9) of the three Achilles tendon samples are as follows: f=20.4±2.0%, T2m=7.1±0.9 us, RM0m=2.9±1.2 s-1 and R1w=1.7±0.1 s-1 with T1=639.7±49.9 ms.

UTE-MT imaging can be accelerated with compressed sensing (CS) reconstruction. 3D UTE sequences typically require undersampling to reduce scan time, but this produces streak artifacts. Recent advances in compressed sensing (CS) reconstruction permit data recovery from extremely undersampled data. We have implemented 3D CS reconstruction from highly undersampled data, and have shown considerably reduced streaks compared with standard reconstruction.

Figure 23:
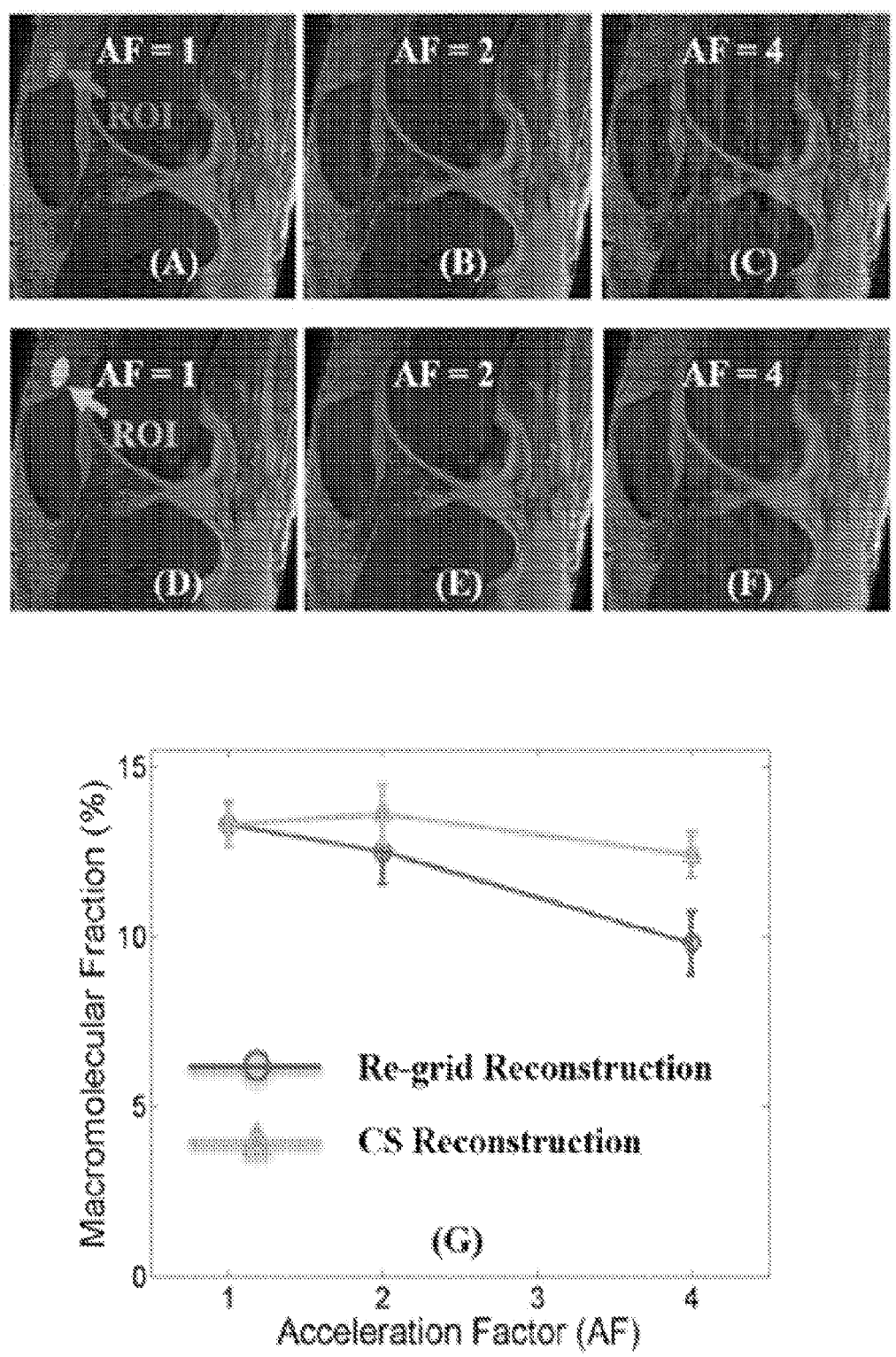
FIG. 23 shows example images and a graph depicting the results of compressed sensing (CS) reconstruction.

FIG. 23 shows example images and a graph depicting the benefits of compressed sensing (CS) reconstruction. 3D UTE images can be obtained with an acceleration factor of up to 4 with macromolecular fraction underestimated by 26.3% with re-gridding reconstruction to 6.7% with CS reconstruction. As shown in FIG. 23, the example Cones-MT imaging of a knee joint with conventional re-gridding and acceleration factor of 1 (panel A), 2 (panel B), 4 (panel C), CS reconstruction with acceleration factor of 1 (panel D), 2 (panel E), 4 (panel F), and macromolecular fraction in patella tendon derived from Cones-MT modeling (graph G). CS reconstruction shows drastically reduced artifacts (panels A-F) and quantification errors (graph G).

UTE-MT sequences can provide angle insensitive biomarkers of tissue properties. As previously shown in FIG. 5, the relationship of UTE-MT modeling parameters and T2* relaxation time was shown with respect to angular orientation in a representative cadaveric human Achilles tendon sample. T2* showed a strong magic angle behavior, with ~6 times increase from 2.5 ms when the sample was oriented parallel to the B0 field, to 14.8 ms when the sample was oriented 55° relative to the B0 field. Meanwhile, the UTE-MT modeling parameters, including macromolecular proton fractions (f), T2 value of macromolecular proton (T2m), exchange rate from macromolecular proton to water proton (RM0w) and fitting residuals derived from MT modeling, which showed minimal angular dependence with less than 10% variation. The example results suggested that the f, T2m and RM0w can be used as magic angle insensitive biomarkers of tissue properties.

Figure 24:
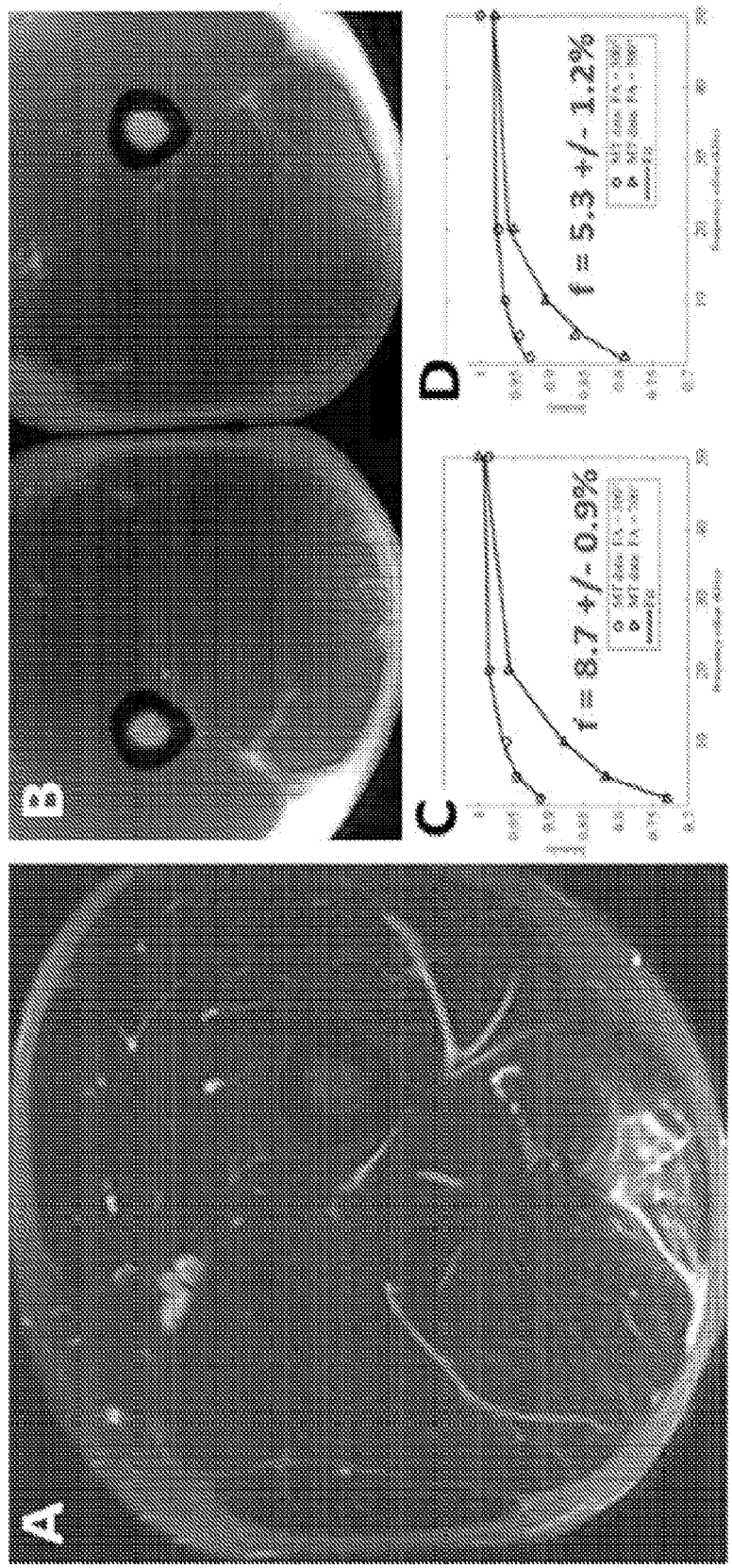
FIGS. 24 and 25 show example images and data plots from baseball player subjects with a injuries.

FIG. 24 shows example images and plots from a professional baseball player with a grade 2 hamstring injury 2 weeks prior. The macromolecular fraction of the injured left biceps femoris muscle measured 5.3%, which was 61% of the value compared to the uninjured side (measuring 8.7%). The patient was able to return to play three weeks after the MRI. As shown in FIG. 24, (A) conventional MR image shows low grade injury to the MTJ of the long head of the biceps femoris, predominantly involving muscle; (panels B-D) 3D UTE-Cones-MT modeling was performed on both biceps femoris muscles showing macromolecular fraction of 5.3% on the injured left side and 8.7% on the uninjured.

Figure 25:
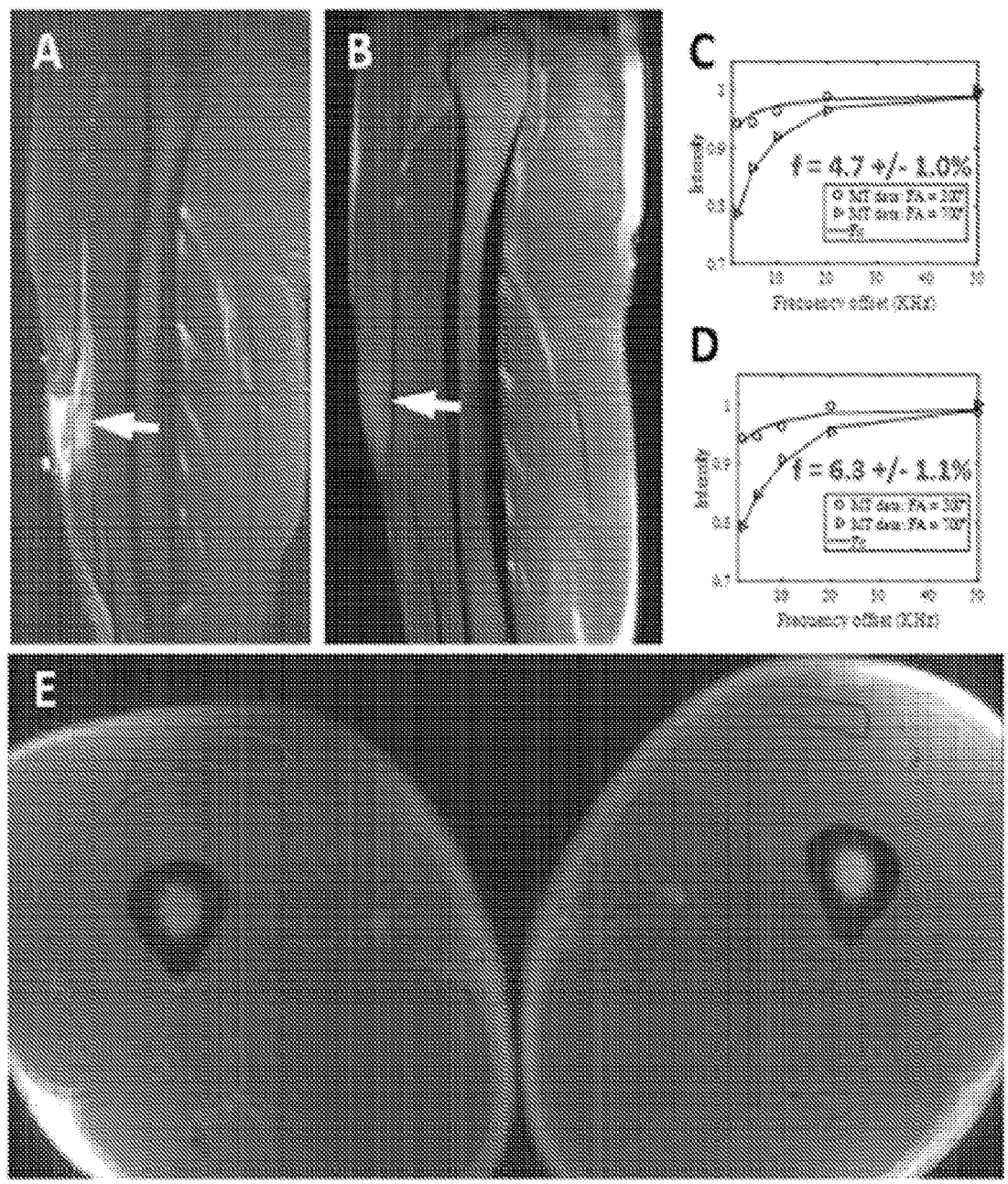

FIG. 25 shows example images and plots from another professional baseball player with a grade 3 quadriceps injury 4 months prior. The macromolecular fraction of the injured left rectus femoris muscle measured 4.7%, which was 75% of the value compared to the uninjured side (measuring 6.3%). The patient was able to return to play one week after the MM. As shown in FIG. 25, (panel A) conventional fluid-sensitive MR image shows acute grade 3 injury to the MTJ of the left distal rectus femoris (arrows); (panel B) MRI 4 months later shows regeneration of muscle; and (panels C-E) UTE-MT modeling with source image showing ROIs demonstrates macromolecular fraction of 4.7% on the injured left side versus 6.3% on the uninjured right side. Clinically, the patient was improving and returned to play one week after the MRI.

An example 3D UTE-Cones sequence, e.g., such as that shown in FIG. 17A, can be configured to include a short rectangular pulse (e.g., 26-52 μs) for signal excitation. The 3D k-space can be divided into multiple cones with twisted radial trajectories along each cone. The Cones trajectories, demonstrated in an example shown in FIG. 17B, are more time-efficient than radial trajectories in covering 3D k-space, and resolve the limitations associated with 2D UTE sequences which are sensitive to eddy currents because of half-pulse excitation. Furthermore, the 3D-UTE-Cones sequence can allow anisotropic fields of view (FOVs) and spatial resolution (higher in-plane resolution, thicker slice), e.g., resulting in vastly reduced scan times. In this manner, for example, volumetric imaging can be achieved in two to five minutes. This time efficiency greatly benefits clinical applications.

Figure 26:
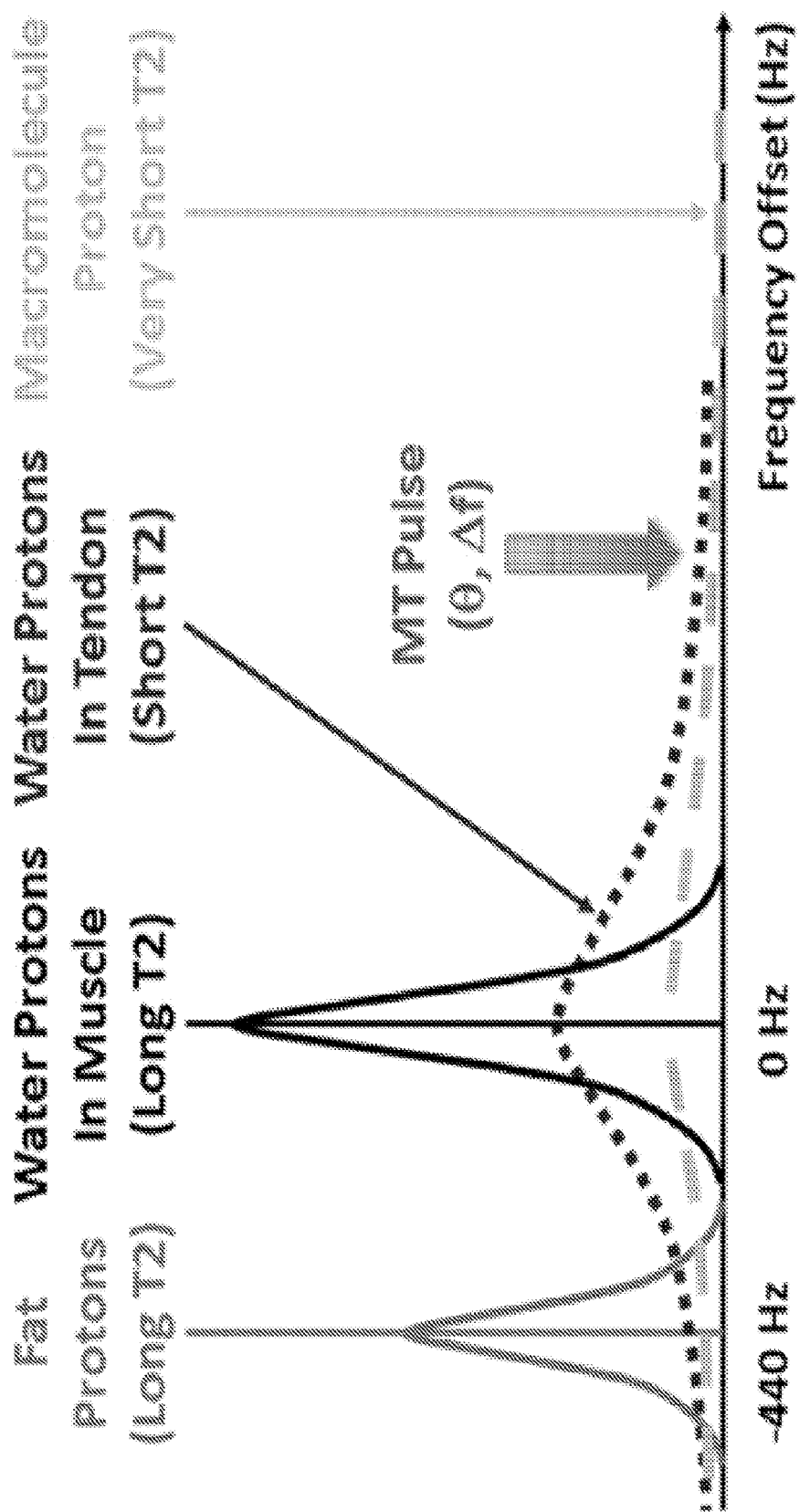
FIG. 26 shows a plot depicting exchangeable proton pools in the myotendinous junction.

Clinical MT sequences employ off-resonance saturation pulses followed by conventional data acquisitions. The MT pulse can be placed at a frequency Δf that is far from the narrow line of water. FIG. 26 shows an example. The MT pulse typically results in selective saturation of macromolecular protons which exchange with water, leading to a reduction in detectable signal. MT is ideal for probing interactions between macromolecular protons and water protons of the tissue being investigated. The MT effect is typically assessed with MTR, such as from MTR=1−$M_{sat}$/$M_0$, where $M_0$ and $M_{sat}$ are the magnetization before and after the MT pulse.

FIG. 26 shows a plot depicting exchangeable proton pools in the myotendinous junction, e.g., water protons in muscle with a long $T_2$, water protons in tendon with a short $T_2$ and macromolecular protons with extremely short $T_2$. At lower Δf, signals from water and macromolecular protons are suppressed. At high Δf, only signals from macromolecular protons are suppressed. MTR is related to θ and Δf. MT modeling can quantify water and macromolecular protons.

Figure 27B:
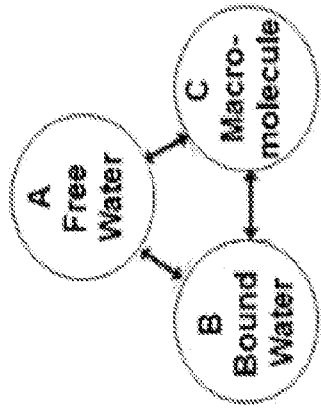
FIGS. 27A-27D show diagrams of example multi-pool models.
Figure 27D:
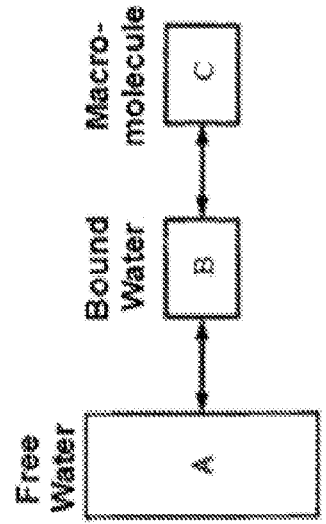
Figure 27A:
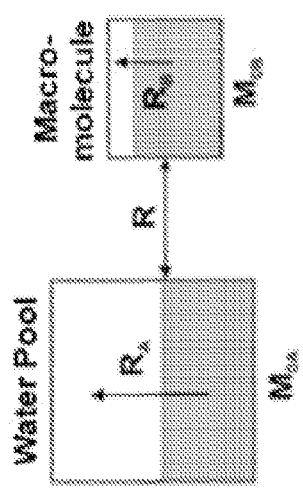
Figure 27C:
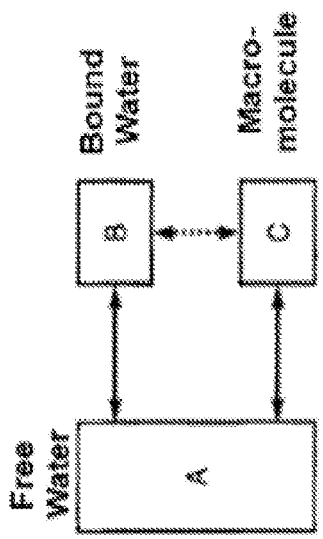

FIGS. 27A-27D show diagrams of example multi-pool models, including a two-pool model in which water and macromolecule protons are exchangeable (FIG. 27A); a three-pool model in which free water, bound water and collagen protons are freely exchangeable, e.g., three-way exchangeable (FIG. 27B); a three-pool model in which bound water and macromolecule protons are exchangeable only with free water, e.g., two-way exchangeable (FIG. 27C); and a three-pool model in which free water and macromolecule protons can only be exchanged via bound water protons, e.g., one-way exchangeable (FIG. 27D).

Since MT modeling requires repeated data acquisition with a series of MT powers and frequency offsets, the associated long scan time is a big challenge for clinical implementation. To reduce scan time, several spiral spokes (Nsp) can be acquired after each MT preparation pulse (e.g., scan time being reduced by a factor of Nsp). To reduce errors associated with this multi-spoke approach, an example modified rectangular pulse (RP) was used. The example simulation results showed that the RP model performed much better than the widely used continuous wave power equivalent model. The example RP model results in nearly constant macromolecular fraction, T2 and R1 relaxation times while significant changes were observed for these parameters in the CWPE model when more spokes were acquired per MT preparation. The example RP model outperforms the CWPE model especially when more spokes are acquired per MT preparation. For a representative $N_{sp}$ of 9, the CWPE model underestimates macromolecule fraction by more than 25% and $RM_{0m}$ by 60%, and overestimates $T_{2w}$ by more than 50%. In comparison, for example, the example RP model can accurately estimate all these parameters, with less than 3% error for f, $T_{2m}$ and $R_{1w}$. Slightly increased errors were observed for $T_{2w}$ and $RM_{0m}$, but still less than 10% for a $N_{sp}$ of 9.

Example Applications: Osteoporosis Evaluations

In some example applications of the disclosed technology, systems and methods can be used for evaluations of osteoporosis (OP) in patient subjects.

Routine clinical evaluation of OP has been focused on dual energy X-ray absorptiometry (DEXA) and/or computed tomography (CT), which provides qualitative analysis of bone mineral (e.g., ~45% of bone by volume). The majority of bone which is the organic matrix and water (e.g., ~55% of bone by volume) plays an important role in bone viscosity and strength.

Bone is a composite material consisting of mineral (~45% by volume), organic matrix (~30%) and water (~25%). The World Health Organization (WHO) Task Force on OP recommended using bone mineral density (BMD) for determining fracture risk although briefly mentioning the importance of microstructure. BMD has been used in the diagnosis of OP (e.g., T-score<−2.5), assessing fracture risk and monitoring response to drug intervention. However, numerous recent clinical studies have demonstrated the limitations of BMD measurements. For example, BMD by itself only predicts fractures with an accuracy of 30-50%. The overall fracture risk increases 13-fold from ages 60 to 80, but BMD alone only predicts a doubling of the fracture risk. A recent study of over 7806 patients found that only 44% of all non-vertebral fractures occurred in women with a T-score below −2.5 (WHO definition of OP). This percentage dropped to 21% in men. As such there is a clear need for more sensitive risk assessment tools which not only use BMD, but other determinants of risk such as bone microstructure, porosity, organic matrix, bone water. The organic matrix and water are undetectable with any of the current non-invasive imaging and/or quantification techniques.

Moreover, bone loss involves thinning of the cortex as well as an increase in cortical porosity ranging from about 3-40%. A large number of studies have confirmed that porosity has a dramatic impact on the mechanical properties of bone. Age related increase in porosity explains 76% of the loss of cortical bone strength with age. A 4% rise in porosity enhances crack propagation through cortical bone by 84%. An increase in porosity from 4-10% more than halves the peak stress that can be tolerated by bone before fracture. The elastic modulus of bone decreases as a power of increasing porosity. Furthermore, fracture toughness is affected by changes in porosity but independent of BMD.

There is also mounting evidence showing age and disease related changes in organic matrix and structure. While bone mineral provides stiffness and strength, collagen provides ductibility and the ability to absorb energy before fracturing. The nature and role of water in bone has been studied. Bone water occurs at various locations and in different states. It is associated with the mineral phase, bound to the organic matrix, and in 'free' form in the microscopic pores of the Haversian and lacunar-canalicular systems. Change in the mineral fraction will typically result in a compensatory change in water fraction. The bound water concentration in bone reflects organic matrix density, while the free water concentration in bone can potentially provide a surrogate measure of bone porosity.

DEXA is the current standard technique for assessing bone. However, it can only provide information on BMD, but not on bone porosity, organic matrix and water. Computed tomography (CT) scans, e.g., $\mu$CT, has emerged as a reference tool for assessing bone porosity, but only in vitro applications, and therefore not useful for clinical use. The recent development of high resolution peripheral quantitative CT (voxels down to 82 $\mu$m isotropic) has allowed in-vivo assessment of bone porosity, and preliminary results have shown a high correlation between cortical porosity and biomechanical assessment. Limitations of this technique include the use of ionizing radiation, as well as the inability to detect small pores (e.g., small pores<82 $\mu$m) or assess organic matrix and bone water.

Magnetic resonance imaging (MRI) detects signals from water in tissues, thus potential for detecting the collagen matrix (bound water) and bone porosity (bulk water). However, bone water has very short transverse relaxation time ($T_2^*$) and is undetectable using conventional MR sequences on clinical MR systems.

The systems and methods in accordance with embodiments of the disclosed technology allow quantification of T1s, T2s, fractions and exchange rates of bound water, free water and collagen protons in cortical bone. Free water fraction can be used to evaluate cortical porosity, while bound water fraction and especially collagen proton fraction can be used to evaluate organic matrix density. Maps of T1s, T2s, exchange rates and fractions are likely to provide much more comprehensive assessment of bone quality and quantity than current gold standard technique, DEXA as well as CT techniques.

For example, the disclosed UTE-MT imaging and modeling techniques can provide a reliable assessment of T1s, T2s, exchange rates and proton fractions of bound/free water and macromolecules in short T2 tissues such as cortical bone. As such, the disclosed UTE-MT imaging and modeling techniques can be used to accurately evaluate changes in organic matrix in cortical bone, which is inaccessible with conventional techniques such as DEXA and CT. In implementations, for example, free water (a biomarker of cortical porosity) and bound water (a biomarker of organic matrix) are measured, in which the biomarkers associated with OP are likely to increase the accuracy in predicting bone properties, and thereby improve treatment monitoring.

Example Applications: Osteoarthritis Evaluations

In some example applications of the disclosed technology, systems and methods can be used for evaluations of osteoarthritis (OA) in patient subjects.

Current, conventional MR techniques to evaluating OA suffer from at least the following problems. (1) OA is a systematic disease involving all the major joint tissues but clinical sequences can only detect long T2 signals from articular cartilage, with little or no signal from many of the joint tissues with short mean T2s. (2) Over the past two decades extensive research in OA has focused on two particular biomarkers: $T_{1\rho}$ and $T_2$. $T_{1\rho}$ has been shown to be sensitive to PG depletion, while T2 is sensitive to collagen degradation. The principal confounding factor for $T_2$ and $T_{1rho}$ ($T_{1\rho}$) measures is the magic angle effect, which may result in a several fold increase in $T_2$ and $T_{1\rho}$ depending on fiber type and orientation to $B_0$. This often far exceeds the changes produced by disease, and may make definitive interpretation of elevated $T_{1\rho}$s and $T_2$s difficult or impossible. This is a major limitation in employing clinical $T_2$ and $T_{1\rho}$ measurements to detect early OA.

The most important early biochemical and microscopic signs of OA include loss of proteoglycans (PGs), changes in collagen microstructure and water content. A large number of recent studies have focused on establishing correlations between quantitative MR parameters ($T_1$, $T_2$, $T_2^*$, $T_{1\rho}$) and the biochemical, structural and biomechanical properties of articular cartilage. For example, two major barriers to progress include the following. (1) OA is a "whole joint organ" disease involving many joint tissues, although emphasis is usually placed on the changes seen in articular cartilage. When one tissue begins to deteriorate, it is very likely to affect others and contribute to failure of the joint as a whole. Unfortunately, many knee joint tissues or tissue components such as menisci, anterior cruciate ligaments (ACL) and posterior cruciate ligaments (PCL), tendons, subchondral bone and the deep layers of articular cartilage, have short $T_2$s of a few milliseconds or less. They show very little or no signal with conventional clinical MR pulse sequences with typical TEs of several milliseconds or longer. The lack of signal means that conventional clinical MR pulse sequences are often of limited value for detecting evidence of early biochemical changes such as PG depletion and collagen degradation in these tissues. (2) Distinct water compartments are present in joint tissues including articular cartilage, menisci, ligaments, tendons and subchondral bone. For example, three distinct water components were investigated, namely water bound to PGs ($T_2$~1 ms), water bound to collagen (T2~4 ms) and free water (T2~20 ms), in bovine knee cartilage using a magnetization transfer model. Also, three components in bovine cartilage were studied using multi-component analysis of CPMG spin echo data (e.g., SNR>8000). These studies were performed on small cadaveric samples using small bore spectrometers, which are not suitable for clinical examinations.

However, due to these limitations, conventional clinical MR imaging typically employs single component analysis to quantify relaxation times of only the longer T2 tissue components, such as the longer T2 components of the more superficial layers of articular cartilage.

Two particular biomarkers have been focused on in conventional evaluation techniques of OA: T1$\rho$ and T2. T1$\rho$ is sensitive to PG depletion. T2 is sensitive to collagen matrix degradation. Yet, the main confounding factor for T2 and T1$\rho$ measurements is the magic angle effect, e.g., the dipolar interactions between protons within the bound water become zero when the fibers are oriented 55° to $B_0$, often resulting in up to several fold increase in T2 and T1$\rho$. This may exceed the change produced by degeneration. Conventional T2 and T1$\rho$ sequences cannot assess a majority of the joint tissues, and cannot evaluate bound water in both short and long T2 tissues. This is probably one of the main reasons that conventional clinical MR sequences still have very limited clinical utility in early OA diagnosis and therapeutic monitoring, while radiography still remains the current standard.

The systems and methods in accordance with embodiments of the disclosed technology allow OA evaluation in a more systematic way, e.g., by focusing not only on the long T2 component of articular cartilage but the short T2 component of this tissue and other short T2 tissues including their bound and free water components as well as macromolecule protons. Furthermore, biomarkers such as fractions and exchange rates of bound water, free water and macromolecule protons are magic angle insensitive. Therefore, the disclosed techniques are envisioned to provide new biomarkers more sensitive to early stages of joint degeneration characterized by disruption of collagen, loss of proteoglycans (PG) and increase in water content.

For example, the disclosed UTE-MT imaging and modeling techniques can provide quantitative information on macromolecule protons, thus can access proteoglycan and collagen changes in deep layers of articular cartilage, meniscus, ligaments, tendons and bone. These biomarkers are likely going to allow early diagnosis of OA, and help treatment monitoring.

Moreover, in some example applications of the disclosed technology, systems and methods can be used for evaluations of tendon disease in patient subjects. For example, the disclosed UTE-MT imaging and modeling techniques can provides quantitative information on water and macromolecule protons, and thus provide access to quantifying and imaging a patient's tendon, which typically shows little or no signal with conventional clinical MR sequences. These biomarkers are likely going to allow early diagnosis of tendon diseases, and help treatment monitoring.

EXAMPLES

In some embodiments in accordance with the present technology (example A1), a magnetic resonance imaging (MRI) method for characterizing a tissue includes generating a set of magnetization transfer (MT) parameters associated with one or more substances of the tissue having different proton groups using an MT model to produce an ultrashort echo time (UTE) MR imaging procedure of the tissue; acquiring magnetic resonance (MR) data from the tissue using an MRI acquisition system by applying the UTE MR data acquisition procedure based on the generated MT parameters, in which the UTE MR data acquisition procedure includes: applying a first series of off-resonance radio frequency (RF) pulses at a first power setting at two or more frequencies, detecting signal data from the tissue based on the applied first series of off-resonance RF pulses, applying a second series of off-resonance RF pulses at a second power setting different than that of the first series and at the two or more frequencies that are the same as the first series, and detecting signal data from the tissue based on the applied second series of off-resonance RF pulses; and producing a data set including one or both of quantitative values and MR images indicative of at least one biomarker of the tissue.

Example A2 includes the method of example A1, in which the MT model is a two-pool MT model, and in which the generated MT parameters include at least some parameters from a group consisting of a fraction of water (f); transverse relaxation time of macromolecule protons ($T2_m$); an exchange rate parameter ($RM_{0m}$), where R is a first-order magnetization exchange rate constant, and $M_{0w}$ is the fully relaxed magnetization of water; a recovery rate of longitudinal magnetization of water ($R_w$); and a residual value.

Example A3 includes the method of example A1, in which the MT model is a three-pool MT model including a free water pool composed of protons in water that freely move, a bound water pool composed of protons in water bound to macromolecules having reduced mobility, and a semisolid pool that includes macromolecular protons, in which the generated MT parameters include at least some parameters from a group consisting of transverse relaxation time of free water ($T2_A$), transverse relaxation time of bound water ($T2_B$), transverse relaxation time of macromolecule protons ($T2_C$); fraction of free water ($f_A$), fraction of bound water ($f_B$), fraction of macromolecule protons ($f_C$), exchange rate from free water to bound water ($R_{AB}$), exchange rate from bound water to macromolecule ($R_{BC}$), recovery rate of longitudinal magnetization of free water ($R_A$), recovery rate of longitudinal magnetization of bound water ($R_B$), recovery rate of longitudinal magnetization of macromolecule protons ($R_C$), and residual value.

Example A4 includes the method of example A1, in which the acquiring MR data from the tissue using the MRI acquisition system includes at least four scans at two or more power settings.

Example A5 includes the method of example A4, in which the off-resonance RF pulses include two saturation powers in a range of 300° and 1100°.

Example A6 includes the method of example A4, in which the two or more frequencies of the off-resonance RF pulses are in a range 2 kHz to 50 kHz.

Example A7 includes the method of example A1, in which the acquiring MR data from the tissue using the MRI acquisition system includes at least six scans at three or more power settings.

Example A8 includes the method of example A1, in which the acquiring the MR data is at multiple orientations of the tissue relative to an applied magnetic field.

Example A9 includes the method of example A1, in which the producing the data set indicative of the at least one biomarker of the tissue includes: fitting the acquired MR data to a steady-state magnetization equation for the groups of different protons, in which the acquired MR data includes measured values from the detected signals associated with the applied first and second series of off-resonance RF pulses applied at the first and second power settings and at the two or more frequencies, and applying at least one of Super-Lorentzian lineshapes or Gaussian lineshapes to the fitted MR data to produce the quantitative values indicative of protons of the different proton groups including macromolecular protons associated with the one or more substances of the tissue, in which the produced data set includes a plurality of final parameters that provide information about the one or more biomarkers of the tissue.

Example A10 includes the method of example A9, in which the final parameters include a macromolecular proton fraction, a relaxation time parameter, and an exchange rate parameters ($RM_{0m}$), where R is a first-order magnetization exchange rate constant between at least two pools, and $M_{0m}$ and $M_{0w}$ are fully relaxed magnetization of a macromolecular pool and a water pool, respectively.

Example A11 includes the method of example A1, in which the produced UTE MR data acquisition procedure includes a three dimensional (3D) multi-spoke UTE-Cones sequence including (i) a MT preparation pulse followed by (ii) a series of multi-spoke excitation signals including plurality of short RF pulse followed by a plurality of 3D spiral trajectories having a conical view ordering.

Example A12 includes the method of example A11, in which the short RF pulses includes rectangular pulses having a duration of 30 μs or less.

Example A13 includes the method of example A11, in which the MT preparation pulse includes a Fermi pulse having a duration of approximately 10 ms or less.

Example A14 includes the method of example A1, in which the proton groups include one or more of a free water, bound water or macromolecule protons.

Example A15 includes the method of example A1, in which the tissue includes musculoskeletal tissue including at least one of cortical bone, ligaments, tendons, or menisci.

Example A16 includes the method of example A1, in which the tissue is from a living subject or tissue specimen.

Example A17 includes the method of example A1, in which the MRI acquisition system includes: a magnet to generate a principal magnetic field ($B_0$); a radio frequency (RF) subsystem to apply a plurality of radio frequency pulses to the tissue and to detect an echo signal; and a gradient subsystem to apply a plurality of gradient fields to the tissue in accordance with the UTE MR data acquisition procedure based on the generated MT parameters.

In some embodiments in accordance with the present technology (example A1), a magnetic resonance imaging (MRI) system for characterizing a tissue includes an MRI acquisition system including a magnet to generate a principal magnetic field ($B_0$), a radio frequency (RF) subsystem to apply a plurality of radio frequency pulses to the tissue and to detect an echo signal, and a gradient subsystem to apply a plurality of gradient fields to the tissue; and a data processing device in communication with the MRI acquisition system and including a processor and memory, the data processing device configured to produce an ultrashort echo time (UTE) MR imaging procedure of the tissue based on a set of magnetization transfer (MT) parameters to control the MRI acquisition system in acquiring magnetic resonance (MR) data from the tissue, and to process acquired MR data to produce a data set including one or both of quantitative values and MR images indicative of at least one biomarker of the tissue, in which the UTE MR imaging procedure produced by the data processing device includes instructions to: apply a first series of off-resonance radio frequency (RF) pulses at a first power setting at two or more frequencies, detect signal data from the tissue based on the applied first series of off-resonance RF pulses, apply a second series of off-resonance RF pulses at a second power setting different than that of the first series and at the two or more frequencies that are the same as the first series, and detect signal data from the tissue based on the applied second series of off-resonance RF pulses, in which the MT parameters are associated with one or more substances of the tissue having different proton groups.

Example A19 includes the system of example A18, in which the data processing device is further configured to generate the set of MT from an MT model.

Example A20 includes the system of example A19, in which the MT model is a two-pool MT model, and in which the generated MT parameters include at least some parameters from a group consisting of a fraction of water (f); transverse relaxation time of macromolecule protons ($T2_m$); an exchange rate parameter ($RM_{0m}$), where R is a first-order magnetization exchange rate constant, and $M_{0w}$ is the fully relaxed magnetization of water; a recovery rate of longitudinal magnetization of water ($R_w$); and a residual value.

Example A21 includes the system of example A19, in which the MT model is a three-pool MT model including a free water pool composed of protons in water that freely move, a bound water pool composed of protons in water bound to macromolecules having reduced mobility, and a semisolid pool that includes macromolecular protons, in which the generated MT parameters include at least some parameters from a group consisting of transverse relaxation time of free water ($T2_A$), transverse relaxation time of bound water ($T2_B$), transverse relaxation time of macromolecule protons ($T2_C$); fraction of free water ($f_A$), fraction of bound water ($f_B$), fraction of macromolecule protons ($f_C$), exchange rate from free water to bound water ($R_{AB}$), exchange rate from bound water to macromolecule ($R_{BC}$), recovery rate of longitudinal magnetization of free water ($R_A$), recovery rate of longitudinal magnetization of bound water ($R_B$), recovery rate of longitudinal magnetization of macromolecule protons ($R_C$), and residual value.

Example A22 includes the system of example A18, in which the UTE MR imaging procedure includes at least four MRI scans at two or more power settings by the MRI acquisition system.

Example A23 includes the system of example A18, in which the UTE MR imaging procedure includes MRI scans at multiple orientations of the tissue relative to the principal magnetic field ($B_0$).

Example A24 includes the system of example A18, in which the data processing device is configured to produce the data set indicative of the at least one biomarker of the tissue by: fitting the acquired MR data to a steady-state magnetization equation for the groups of different protons, in which the acquired MR data includes measured values from the detected signals associated with the applied first and second series of off-resonance RF pulses applied at the first and second power settings and at the two or more frequencies, and applying at least one of Super-Lorentzian lineshapes or Gaussian lineshapes to the fitted MR data to produce the quantitative values indicative of protons of the different proton groups including macromolecular protons associated with the one or more substances of the tissue, in which the produced data set includes a plurality of final parameters that provide information about the one or more biomarkers of the tissue.

Example A25 includes the system of example A24, in which the final parameters include a macromolecular proton fraction, a relaxation time parameter, and an exchange rate parameters ($RM_{0m}$), where R is a first-order magnetization exchange rate constant between at least two pools, and $M_{0m}$ and $M_{0w}$ are fully relaxed magnetization of a macromolecular pool and a water pool, respectively.

Example A26 includes the system of example A18, in which the produced UTE MR data acquisition procedure includes a three dimensional (3D) multi-spoke UTE-Cones sequence including (i) a MT preparation pulse followed by (ii) a series of multi-spoke excitation signals including plurality of short RF pulse followed by a plurality of 3D spiral trajectories having a conical view ordering.

Example A27 includes the system of example A26, in which the short RF pulses includes rectangular pulses having a duration of 30 μs or less.

Example A28 includes the system of example A26, in which the MT preparation pulse includes a Fermi pulse having a duration of approximately 10 ms or less.

Example A29 includes the system of example A18, in which the proton groups include one or more of a free water, bound water or macromolecule protons.

Example A30 includes the system of example A18, in which the tissue includes musculoskeletal tissue including at least one of cortical bone, ligaments, tendons, or menisci.

Example A31 includes the system of example A18, in which the tissue is from a living subject or tissue specimen.

In some embodiments in accordance with the present technology (example B1), a method includes using ultra-short echo time magnetization transfer (UTE-MT) imaging and signal modeling to quantify different proton groups in a short transverse relaxation time (T2) tissue including: evaluating longitudinal relaxation times (T1s), transverse relaxation times (T2s), fractions and exchange rates of the different proton groups by subjecting UTE-MT images with a series of MT frequency offsets and MT power to MT modeling; and using magic angle insensitive biomarkers to detect early structural and biochemical alterations in a tissue.

Example B2 includes the method of example B1, in which the different proton groups includes one or more of a free water, bound water or macromolecule protons.

Example B3 includes the method of example B1, in which short T2 tissue includes a tissue associated with a meniscus, a ligament, a tendon or a cortical bone.

Example B4 includes the method of example B1, in which the magic angle insensitive biomarkers include one or more of a fractions and/or exchange rates of bound water, free water or macromolecule protons.

Example B5 includes the method of example B1, in which the tissue includes a musculoskeletal tissue and the method is implemented for diagnosis and/or monitoring of osteoarthritis (OA), osteoporosis (OP), tendon disease or muscle disease.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document and contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Various embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

For example, one aspect of the disclosed embodiments relates to a computer program product that is embodied on a non-transitory computer readable medium. The computer program product includes program code for carrying out any one or and/or all of the operations of the disclosed embodiments.

In some embodiments, the disclosed techniques can be implemented by a device that includes a processor (e.g., a microprocessor) and a memory that includes processor executable instructions. The processor executable instructions, when executed by the processor, configure the device to carry out the various disclosed techniques, including processing digital data that represents underlying physical entities, such a magnetic resonance images, X-ray images of body organs, body tissues or other physical entities.

Only a few implementations and examples are described and other implementations, enhancements and variations can be made based on what is described and illustrated in this patent document.

What is claimed is:

1. A magnetic resonance imaging (MRI) method for characterizing a tissue, comprising:
generating a set of magnetization transfer (MT) parameters associated with one or more substances of the tissue having different proton groups using an MT model to produce an ultrashort echo time (UTE) MR imaging procedure of the tissue;
acquiring magnetic resonance (MR) data from the tissue using an MRI acquisition system by applying the UTE MR data acquisition procedure based on the generated MT parameters, wherein the UTE MR data acquisition procedure includes:
applying a first series of off-resonance radio frequency (RF) pulses at a first power setting at two or more frequencies,
detecting signal data from the tissue based on the applied first series of off-resonance RF pulses,
applying a second series of off-resonance RF pulses at a second power setting different than that of the first series and at the two or more frequencies that are the same as the first series, and
detecting signal data from the tissue based on the applied second series of off-resonance RF pulses; and
producing a data set including one or both of quantitative values and MR images indicative of at least one biomarker of the tissue.

2. The method of claim 1, wherein the MT model is a two-pool MT model, and wherein the generated MT parameters include at least some parameters from a group consisting of a fraction of water (f); transverse relaxation time of macromolecule protons ($T2_m$); an exchange rate parameter ($RM_{0m}$), where R is a first-order magnetization exchange rate constant, and $M_{0w}$ is the fully relaxed magnetization of water; a recovery rate of longitudinal magnetization of water ($R_w$); and a residual value.

3. The method of claim 1, wherein the MT model is a three-pool MT model including a free water pool composed of protons in water that freely move, a bound water pool composed of protons in water bound to macromolecules having reduced mobility, and a semisolid pool that includes macromolecular protons, wherein the generated MT parameters include at least some parameters from a group consisting of transverse relaxation time of free water ($T2_A$), transverse relaxation time of bound water ($T2_B$), transverse relaxation time of macromolecule protons ($T2_C$); fraction of free water ($f_A$), fraction of bound water ($f_B$), fraction of macromolecule protons ($f_C$), exchange rate from free water to bound water ($R_{AB}$), exchange rate from bound water to macromolecule ($R_{BC}$), recovery rate of longitudinal magnetization of free water ($R_A$), recovery rate of longitudinal magnetization of bound water ($R_B$), recovery rate of longitudinal magnetization of macromolecule protons ($R_C$), and residual value.

4. The method of claim 1, wherein the acquiring MR data from the tissue using the MRI acquisition system includes at least four scans at two or more power settings.

5. The method of claim 1, wherein the acquiring MR data from the tissue using the MRI acquisition system includes at least six scans at three or more power settings.

6. The method of claim 1, wherein the acquiring the MR data is at multiple orientations of the tissue relative to an applied magnetic field.

7. The method of claim 1, wherein the producing the data set indicative of the at least one biomarker of the tissue includes:
fitting the acquired MR data to a steady-state magnetization equation for the groups of different protons, wherein the acquired MR data includes measured values from the detected signals associated with the applied first and second series of off-resonance RF pulses applied at the first and second power settings and at the two or more frequencies, and
applying at least one of Super-Lorentzian lineshapes or Gaussian lineshapes to the fitted MR data to produce the quantitative values indicative of protons of the different proton groups including macromolecular protons associated with the one or more substances of the tissue,
wherein the produced data set includes a plurality of final parameters that provide information about the one or more biomarkers of the tissue.

8. The method of claim 7, wherein the final parameters include a macromolecular proton fraction, a relaxation time parameter, and an exchange rate parameters ($RM_{0m}$), where R is a first-order magnetization exchange rate constant between at least two pools, $M_{0m}$ and $M_{0w}$ are fully relaxed magnetization of a macromolecular pool and a water pool, respectively.

9. The method of claim 1, wherein the produced UTE MR data acquisition procedure includes a three dimensional (3D) multi-spoke UTE-Cones sequence including (i) a MT preparation pulse followed by (ii) a series of multi-spoke excitation signals including plurality of short RF pulse followed by a plurality of 3D spiral trajectories having a conical view ordering.

10. The method of claim 1, wherein the proton groups include one or more of a free water, bound water or macromolecule protons.

11. The method of claim 1, wherein the tissue includes musculoskeletal tissue including at least one of cortical bone, ligaments, tendons, or menisci.

12. The method of claim 1, wherein the MRI acquisition system includes:
a magnet to generate a principal magnetic field ($B_0$);
a radio frequency (RF) subsystem to apply a plurality of radio frequency pulses to the tissue and to detect an echo signal; and
a gradient subsystem to apply a plurality of gradient fields to the tissue in accordance with the UTE MR data acquisition procedure based on the generated MT parameters.

13. A magnetic resonance imaging (MRI) system for characterizing a tissue, comprising:
an MRI acquisition system including a magnet to generate a principal magnetic field ($B_0$), a radio frequency (RF) subsystem to apply a plurality of radio frequency pulses to the tissue and to detect an echo signal, and a gradient subsystem to apply a plurality of gradient fields to the tissue; and
a data processing device in communication with the MRI acquisition system and including a processor and memory, the data processing device configured to produce an ultrashort echo time (UTE) MR imaging procedure of the tissue based on a set of magnetization transfer (MT) parameters to control the MRI acquisition system in acquiring magnetic resonance (MR) data from the tissue, and to process acquired MR data to produce a data set including one or both of quantitative values and MR images indicative of at least one biomarker of the tissue, wherein the UTE MR imaging procedure produced by the data processing device includes instructions to:
apply a first series of off-resonance radio frequency (RF) pulses at a first power setting at two or more frequencies,
detect signal data from the tissue based on the applied first series of off-resonance RF pulses,
apply a second series of off-resonance RF pulses at a second power setting different than that of the first series and at the two or more frequencies that are the same as the first series, and
detect signal data from the tissue based on the applied second series of off-resonance RF pulses,
wherein the MT parameters are associated with one or more substances of the tissue having different proton groups.

14. The system of claim 13, wherein the data processing device is further configured to generate the set of MT from an MT model.

15. The system of claim 14, wherein the MT model is a two-pool MT model, and wherein the generated MT parameters include at least some parameters from a group consisting of a fraction of water (f); transverse relaxation time of macromolecule protons ($T2_m$); an exchange rate parameter ($RM_{0m}$), where R is a first-order magnetization exchange rate constant, and $M_{0w}$ is the fully relaxed magnetization of water; a recovery rate of longitudinal magnetization of water ($R_w$); and a residual value.

16. The system of claim 14, wherein the MT model is a three-pool MT model including a free water pool composed of protons in water that freely move, a bound water pool composed of protons in water bound to macromolecules having reduced mobility, and a semisolid pool that includes macromolecular protons, wherein the generated MT parameters include at least some parameters from a group consisting of transverse relaxation time of free water ($T2_A$), transverse relaxation time of bound water ($T2_B$), transverse relaxation time of macromolecule protons ($T2_C$); fraction of free water ($f_A$), fraction of bound water ($f_B$), fraction of macromolecule protons ($f_C$), exchange rate from free water to bound water ($R_{AB}$), exchange rate from bound water to macromolecule ($R_{BC}$), recovery rate of longitudinal magnetization of free water ($R_A$), recovery rate of longitudinal magnetization of bound water ($R_B$), recovery rate of longitudinal magnetization of macromolecule protons ($R_C$), and residual value.

17. The system of claim 13, wherein the UTE MR imaging procedure includes at least four MRI scans at two or more power settings by the MRI acquisition system.

18. The system of claim 13, wherein the UTE MR imaging procedure includes MRI scans at multiple orientations of the tissue relative to the principal magnetic field ($B_0$).

19. The system of claim 13, wherein the data processing device is configured to produce the data set indicative of the at least one biomarker of the tissue by:
fitting the acquired MR data to a steady-state magnetization equation for the groups of different protons, wherein the acquired MR data includes measured values from the detected signals associated with the applied first and second series of off-resonance RF pulses applied at the first and second power settings and at the two or more frequencies, and
applying at least one of Super-Lorentzian lineshapes or Gaussian lineshapes to the fitted MR data to produce the quantitative values indicative of protons of the different proton groups including macromolecular protons associated with the one or more substances of the tissue,
wherein the produced data set includes a plurality of final parameters that provide information about the one or more biomarkers of the tissue.

20. The system of claim 19, wherein the final parameters include a macromolecular proton fraction, a relaxation time parameter, and an exchange rate parameters ($RM_{0m}$), where R is a first-order magnetization exchange rate constant between at least two pools, and $M_{0m}$ and $M_{0w}$ are fully relaxed magnetization of a macromolecular pool and a water pool, respectively.

21. The system of claim 13, wherein the produced UTE MR data acquisition procedure includes a three dimensional (3D) multi-spoke UTE-Cones sequence including (i) a MT preparation pulse followed by (ii) a series of multi-spoke excitation signals including plurality of short RF pulse followed by a plurality of 3D spiral trajectories having a conical view ordering.

22. The system of claim 13, wherein the proton groups include one or more of a free water, bound water or macromolecule protons.

23. The system of claim 13, wherein the tissue includes musculoskeletal tissue including at least one of cortical bone, ligaments, tendons, or menisci.

* * * * *